(12) United States Patent
Roy et al.

(10) Patent No.: US 11,666,691 B2
(45) Date of Patent: Jun. 6, 2023

(54) BIOARTIFICIAL ULTRAFILTRATION DEVICE AND METHODS RELATED THERETO

(71) Applicant: The Regents of the University of California, Oakland, CA (US)

(72) Inventors: Shuvo Roy, San Ramon, CA (US);
Rishi Kant, Foster City, CA (US);
Andrew Posselt, Mill Valley, CA (US);
Shang Song, Redwood City, CA (US);
Willieford Moses, Oakland, CA (US);
Charles Blaha, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 160 days.

(21) Appl. No.: 17/343,361

(22) Filed: Jun. 9, 2021

(65) Prior Publication Data
US 2022/0016324 A1     Jan. 20, 2022

Related U.S. Application Data

(63) Continuation of application No. 16/082,501, filed as application No. PCT/US2017/021196 on Mar. 7, 2017, now Pat. No. 11,033,668.
(Continued)

(51) Int. Cl.
*A61M 1/16*     (2006.01)
*B01D 63/08*     (2006.01)
(Continued)

(52) U.S. Cl.
CPC ..... *A61M 1/1678* (2013.01); *A61B 5/150992* (2013.01); *A61M 1/3689* (2014.02);
(Continued)

(58) Field of Classification Search
CPC .......... A61M 2202/09; A61M 2205/04; A61B 5/150992; B01D 61/145; B01D 63/08;
(Continued)

(56) References Cited

U.S. PATENT DOCUMENTS 6,197,575 B1 *   3/2001   Griffith .............. G01N 33/5008
                                                   435/395
6,472,200 B1    10/2002   Mitrani
(Continued)

FOREIGN PATENT DOCUMENTS

| JP | 2014008585 | 1/2014 |
| WO | 2004024300 | 3/2004 |
| WO | WO2011040889 | 4/2011 |

OTHER PUBLICATIONS

Papra, et al. (2001) "Characterization of Ultrathin Poly(Ethylene Glycol) Monolayers on Silicon Substrates. Langmuir", 17(5):1457-1460.

*Primary Examiner* — Michael L Hobbs
(74) *Attorney, Agent, or Firm* — Edward J. Baba; Shweta Chandra; Bozicevic, Field & Francis LLP

(57) ABSTRACT

Bioartificial ultrafiltration devices comprising a scaffold comprising a population of cells enclosed in a matrix and disposed adjacent a plurality of channels are provided. The population of cells provides molecules such as therapeutic molecules to a subject in need thereof and is supported by the nutrients filtered in an ultrafiltrate from the blood of the subject. The plurality of channels in the scaffold facilitate the transportation of the ultrafiltrate and exchange of molecules between the ultrafiltrate and the population of cells.

20 Claims, 50 Drawing Sheets

Related U.S. Application Data

(60) Provisional application No. 62/328,298, filed on Apr. 27, 2016, provisional application No. 62/304,758, filed on Mar. 7, 2016.

(51) Int. Cl.

| | | |
|---|---|---|
| *B01D 67/00* | (2006.01) | |
| *B01D 69/02* | (2006.01) | |
| *B01D 69/12* | (2006.01) | |
| *B01D 71/02* | (2006.01) | |
| *A61M 1/36* | (2006.01) | |
| *B01D 69/08* | (2006.01) | |
| *A61B 5/15* | (2006.01) | |
| *B01D 61/14* | (2006.01) | |
| *B01D 71/70* | (2006.01) | |
| *B01D 69/14* | (2006.01) | |

(52) U.S. Cl.
CPC ........... *B01D 61/145* (2013.01); *B01D 63/08* (2013.01); *B01D 67/0037* (2013.01); *B01D 67/0072* (2013.01); *B01D 69/02* (2013.01); *B01D 69/08* (2013.01); *B01D 69/12* (2013.01); *B01D 71/027* (2013.01); *A61M 2202/09* (2013.01); *A61M 2205/04* (2013.01); *B01D 69/145* (2013.01); *B01D 71/024* (2013.01); *B01D 71/70* (2013.01); *B01D 2325/021* (2013.01)

(58) Field of Classification Search
CPC ............ B01D 67/0037; B01D 67/0072; B01D 69/02; B01D 69/08; B01D 69/12; B01D 71/027; B01D 71/024; B01D 71/70; B01D 2325/021
See application file for complete search history.

(56) References Cited

U.S. PATENT DOCUMENTS

| | | | |
|---|---|---|---|
| 6,759,245 B1 * | 7/2004 | Toner | .................... C12M 41/32 |
| | | | 435/395 |
| 8,647,861 B2 | 2/2014 | Ingber et al. | |
| 2009/0131858 A1 | 5/2009 | Fissell et al. | |
| 2014/0370094 A1 | 12/2014 | Wray et al. | |
| 2015/0090661 A1 | 4/2015 | Kant et al. | |

* cited by examiner

FIG. 2A
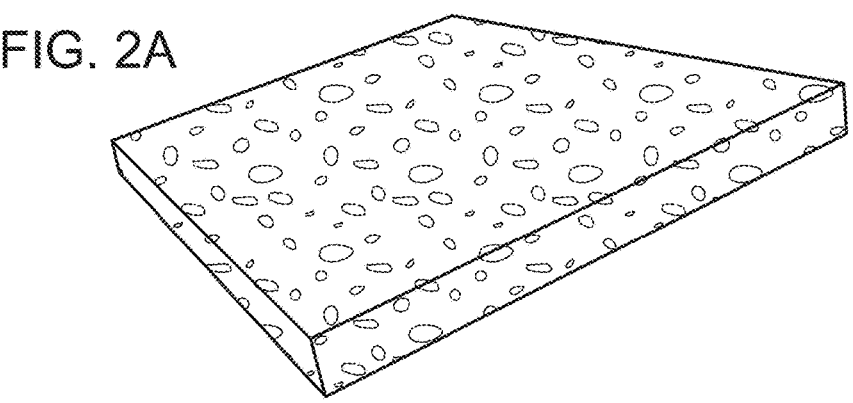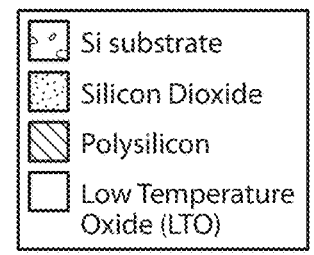
FIG. 2B
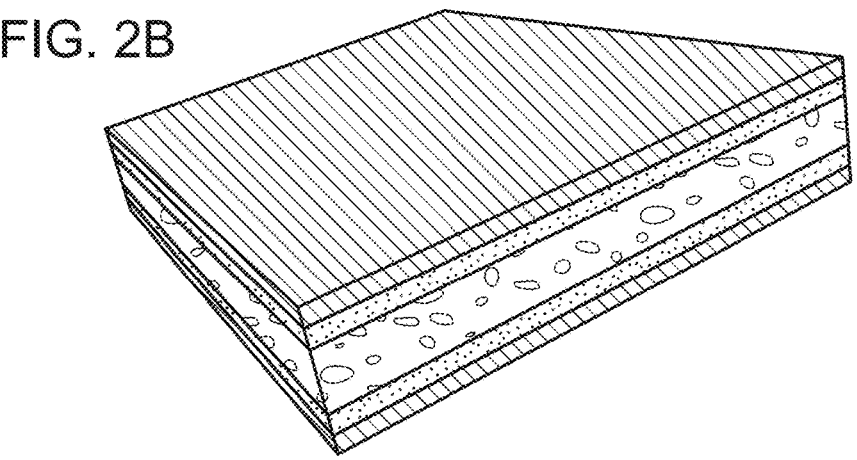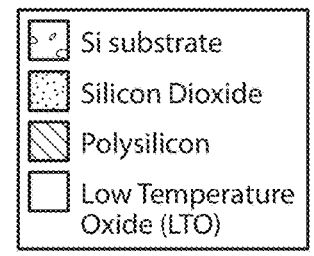
FIG. 2C
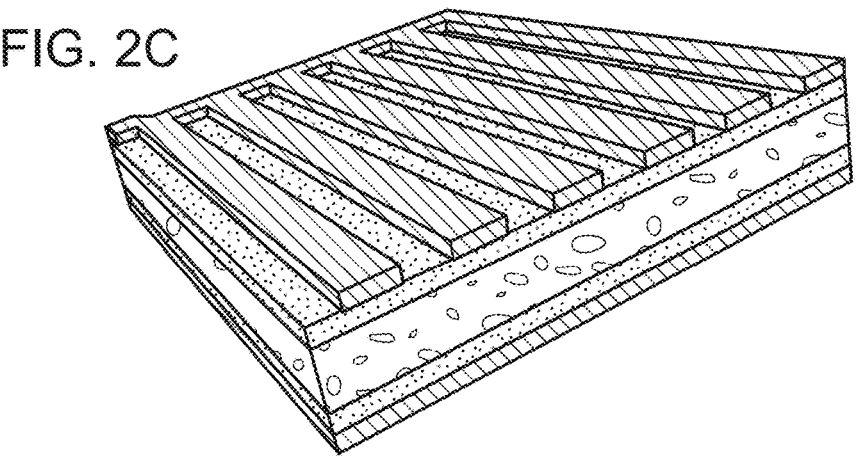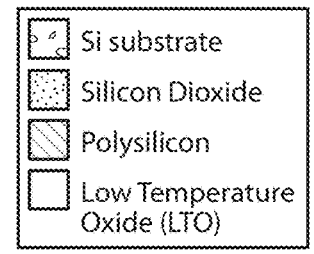

FIG. 2G
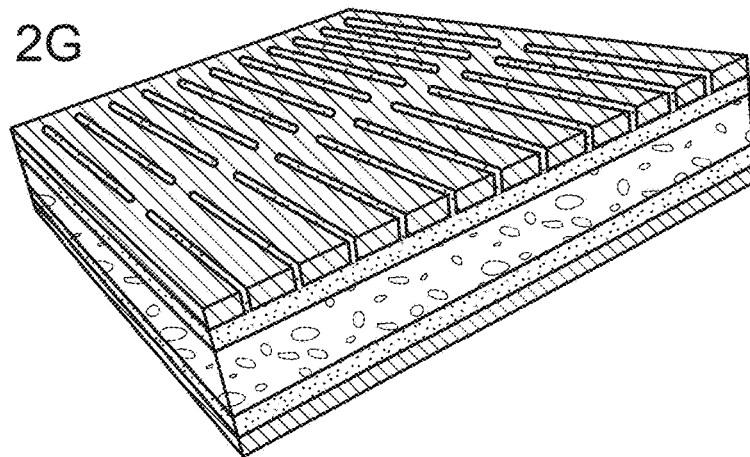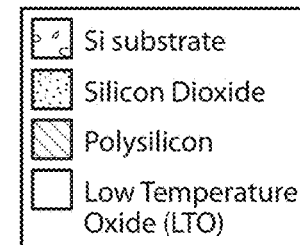
FIG. 2H
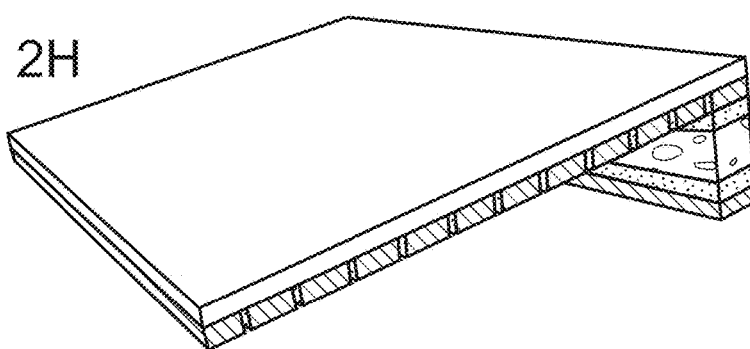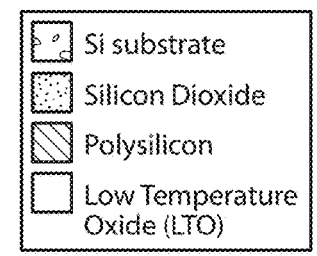
FIG. 2I
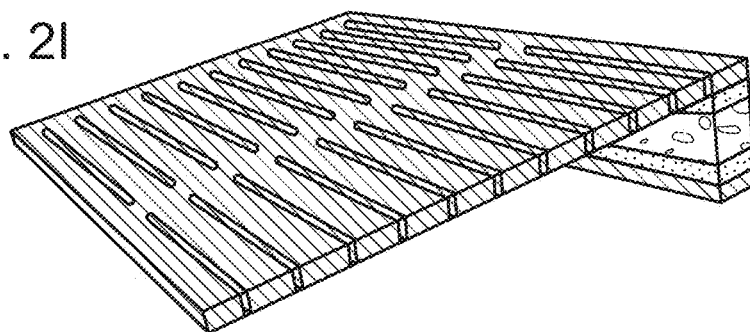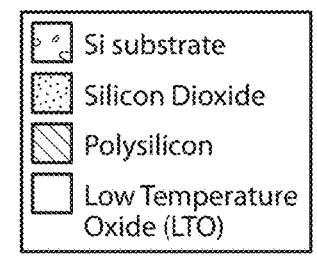

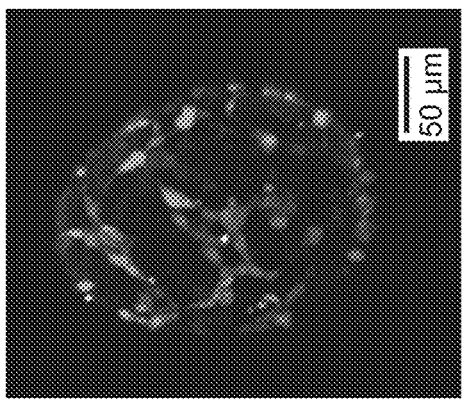
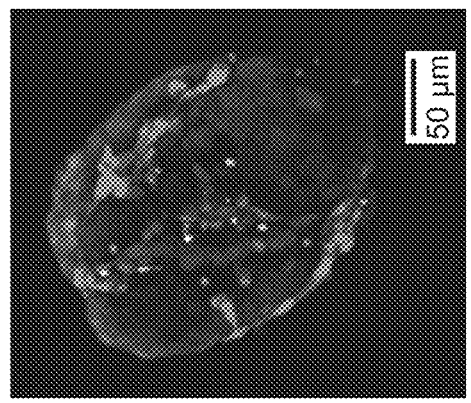
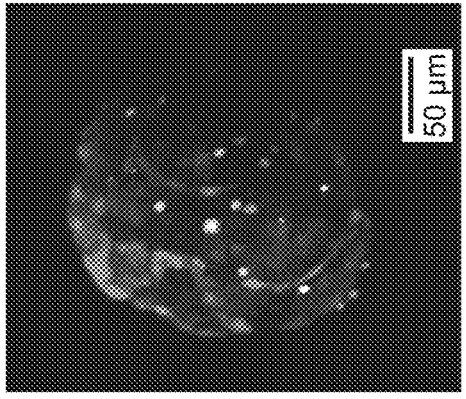
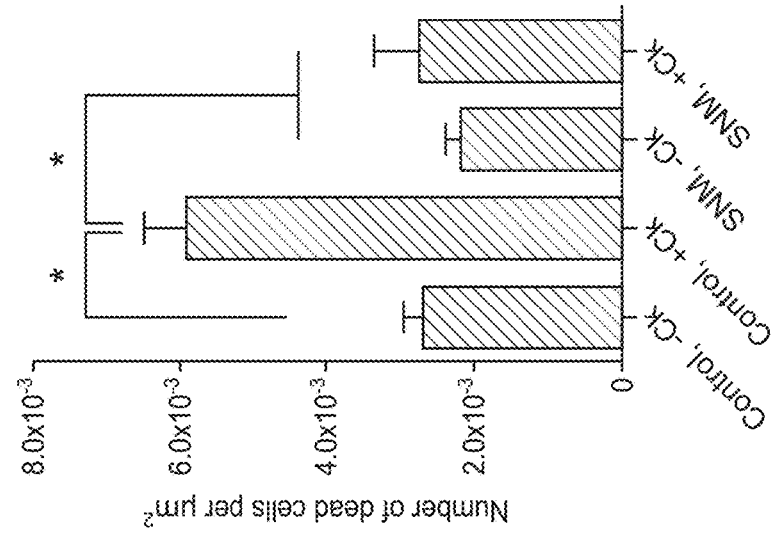

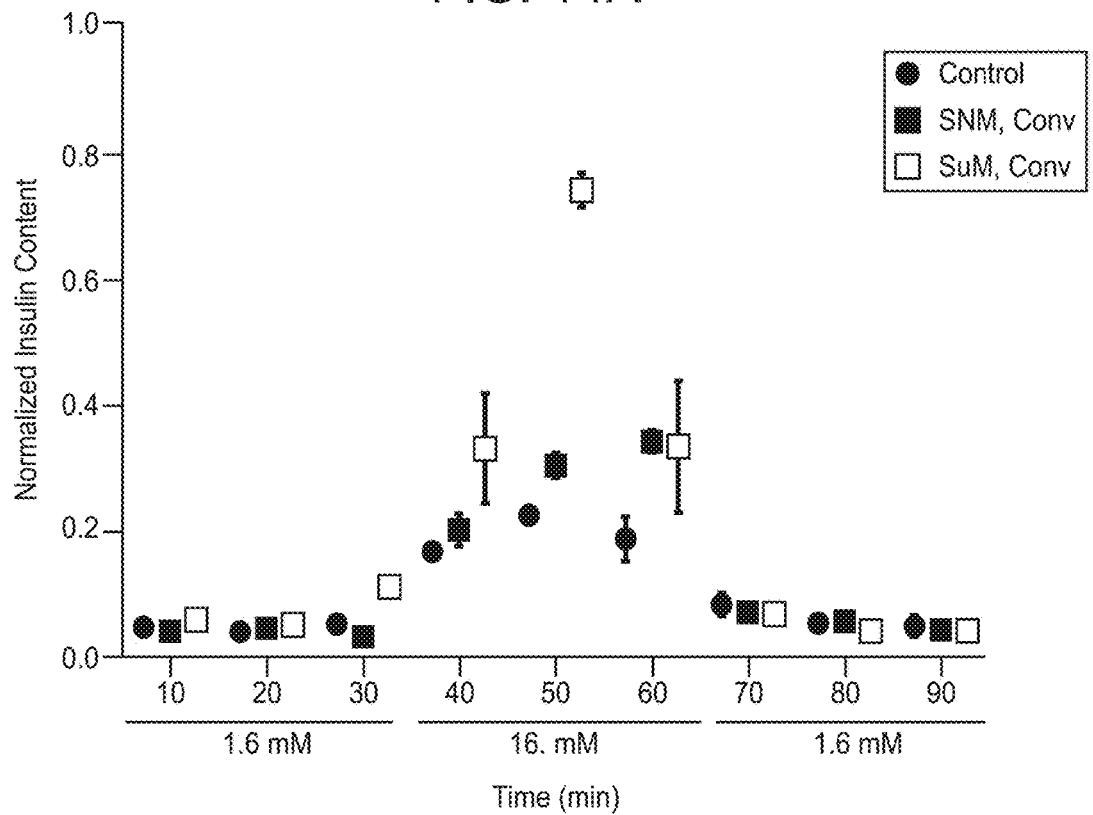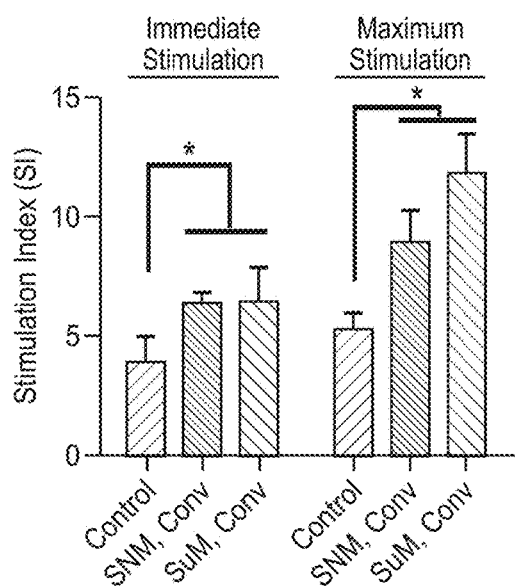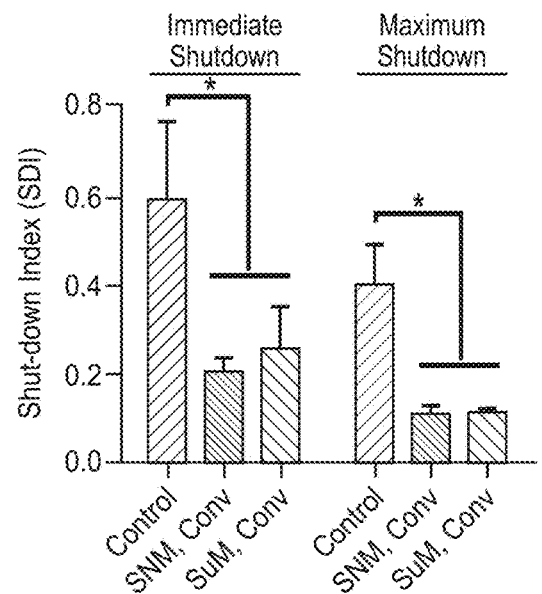

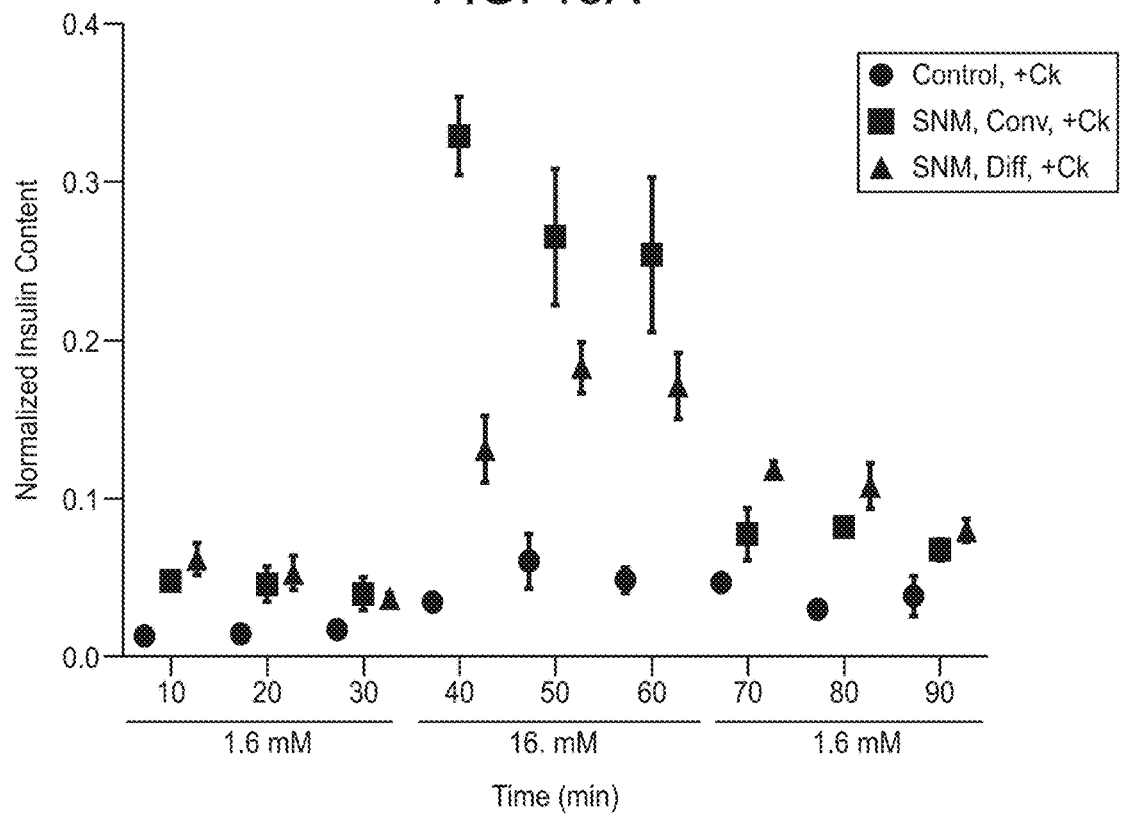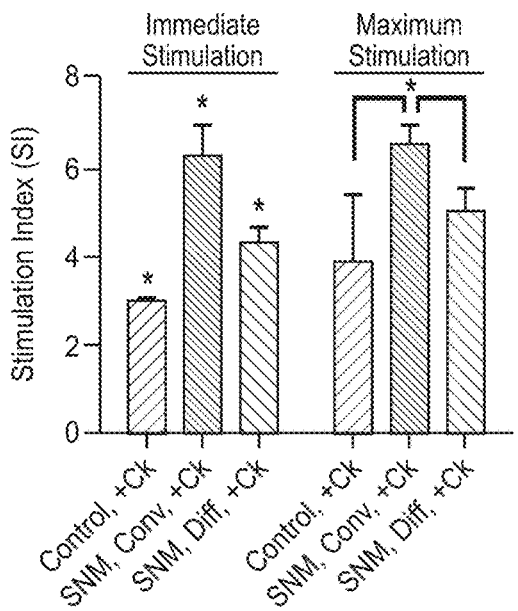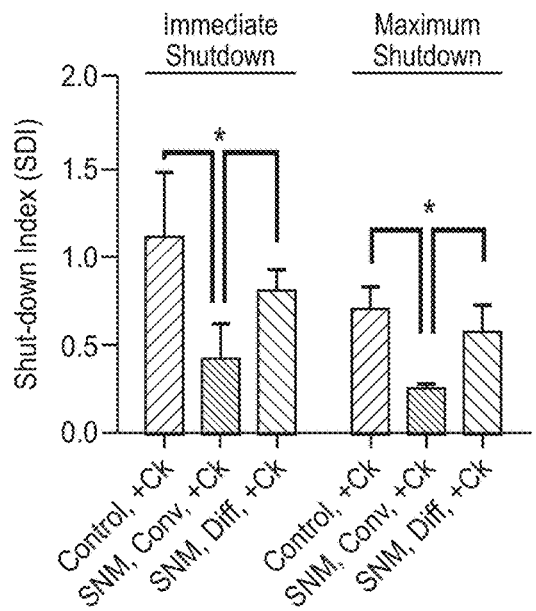

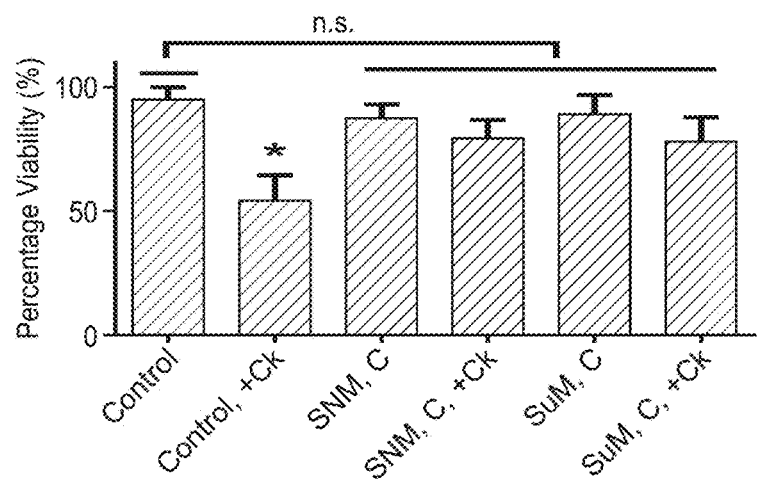
FIG. 17A
FIG. 17B
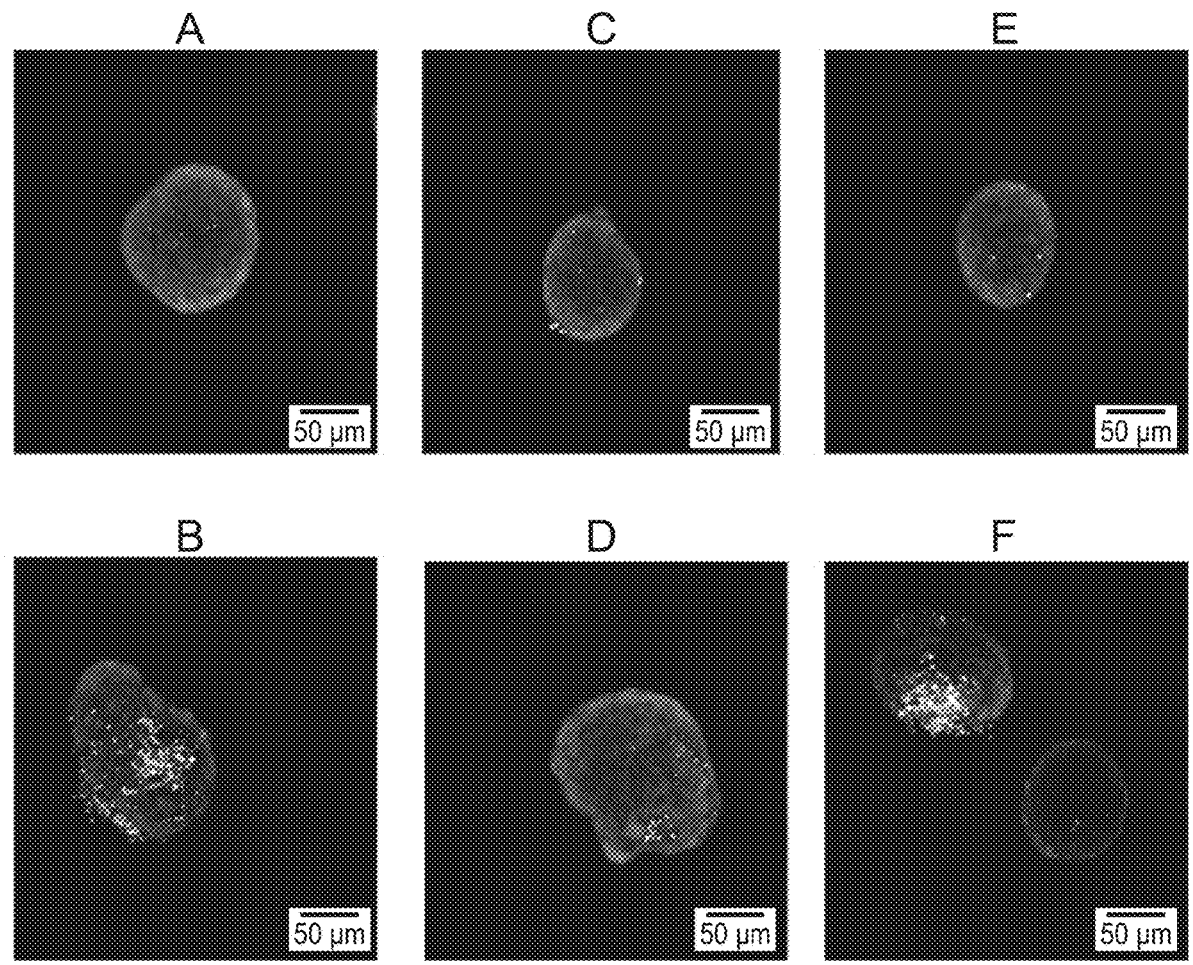

FIG. 18

| Experimental Condition | Low-High Glucose Stimulation ($10^{-2}$) (normalized insulin content * min$^{-1}$) | High-Low Glucose Shut-Down ($10^{-2}$) (normalized insulin content * min$^{-1}$) |
|---|---|---|
| Control | 0.86 | -0.71 |
| SNM, Diff | 0.84 | -0.42 |
| SNM, Conv | 1 | -2.71 |
| SµM, Conv | 3.15 | -3.36 |

FIG. 19

| Experimental Condition | Low-High Glucose Stimulation ($10^{-2}$) (normalized insulin content * min$^{-1}$) | High-Low Glucose Shut-Down ($10^{-2}$) (normalized insulin content * min$^{-1}$) |
|---|---|---|
| Control, +Ck | 0.22 | -0.092 |
| SNM, Diff, +Ck | 0.73 | -0.32 |
| SNM, Conv, +Ck | 2.89 | -1.76 |
| SµM, Conv, +Ck | 1.57 | -2.84 |

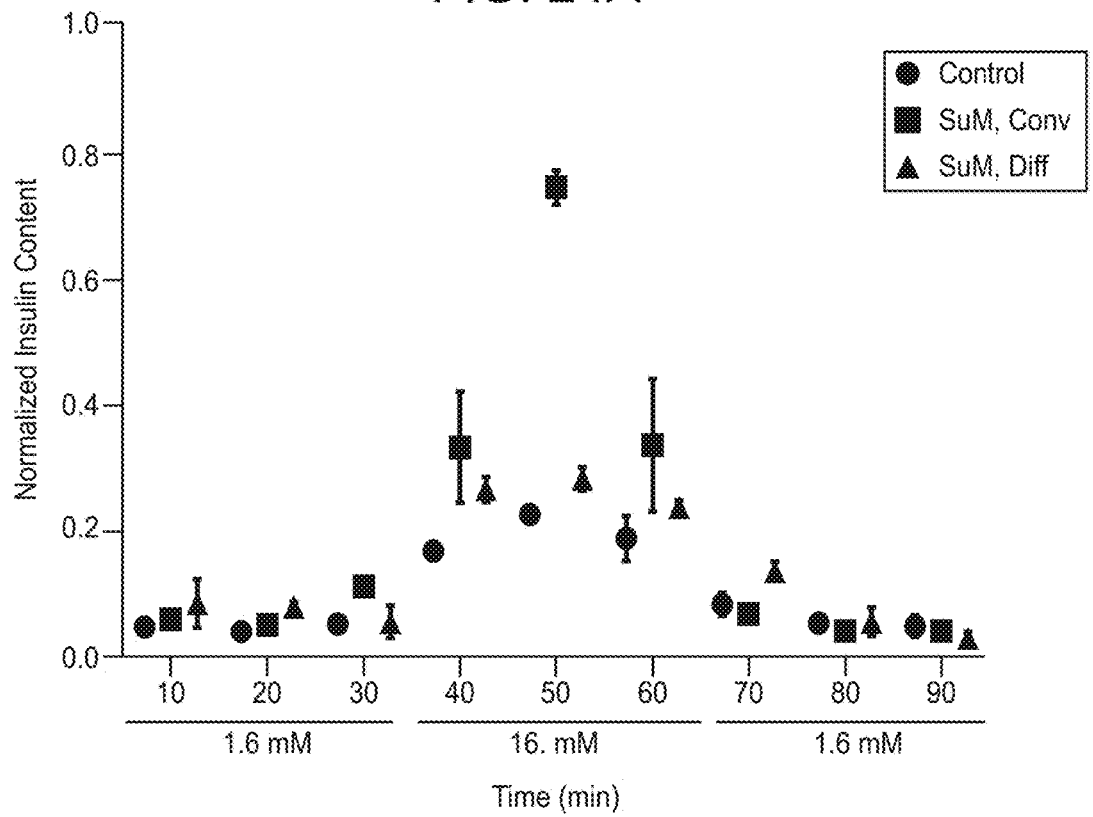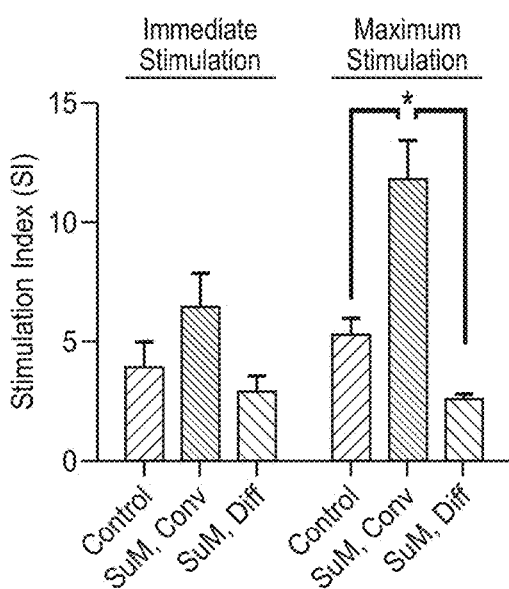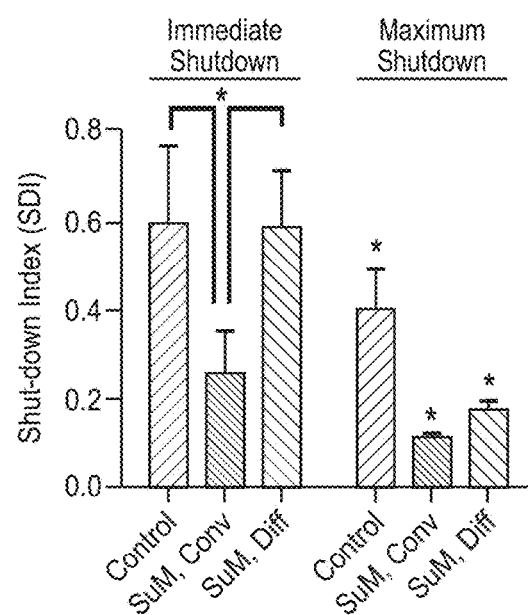

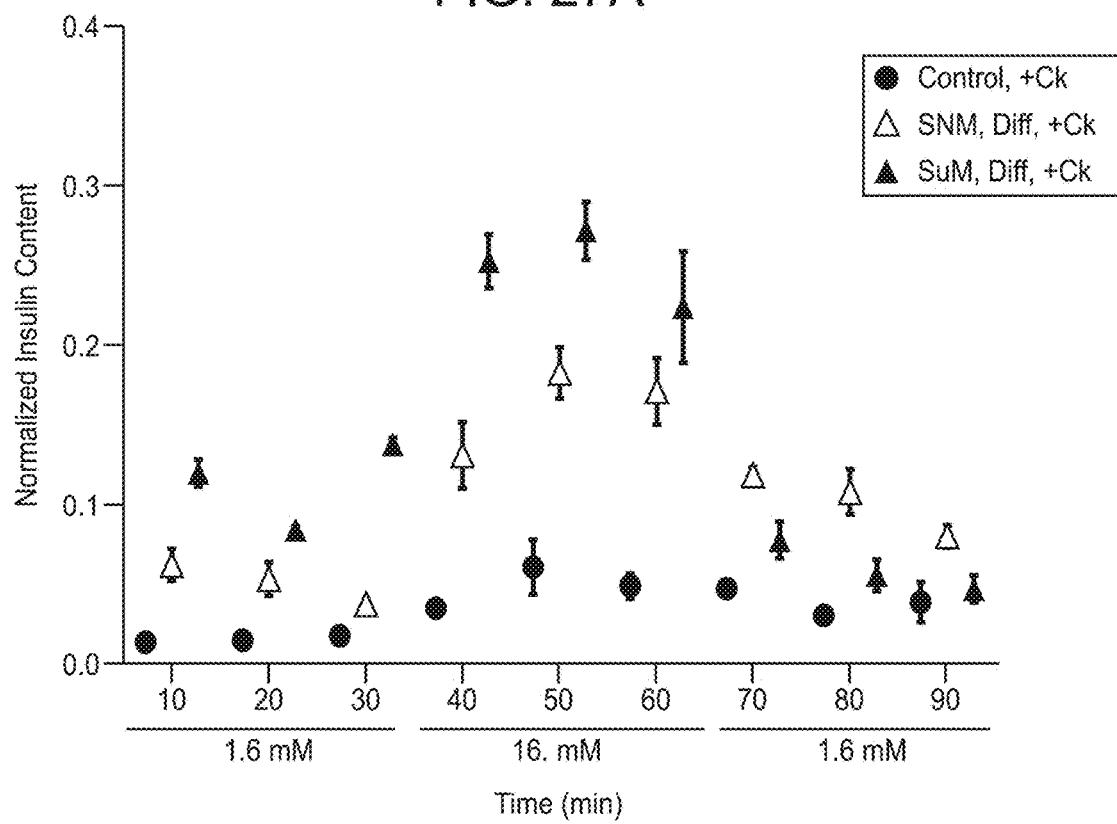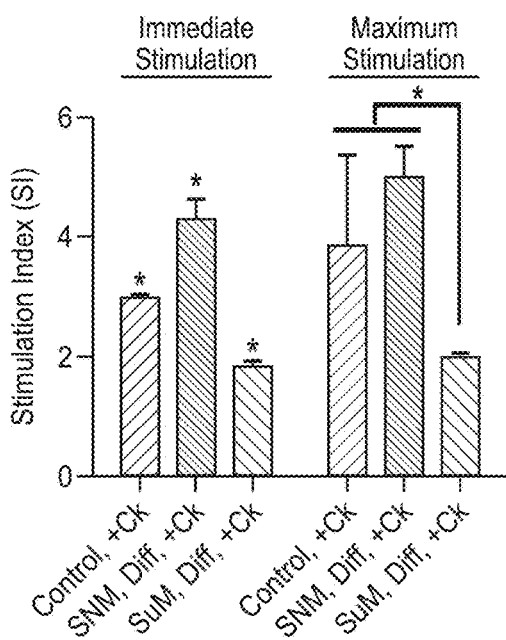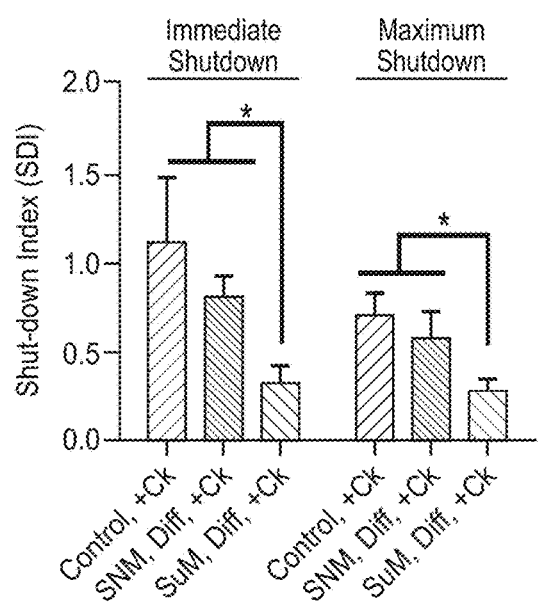

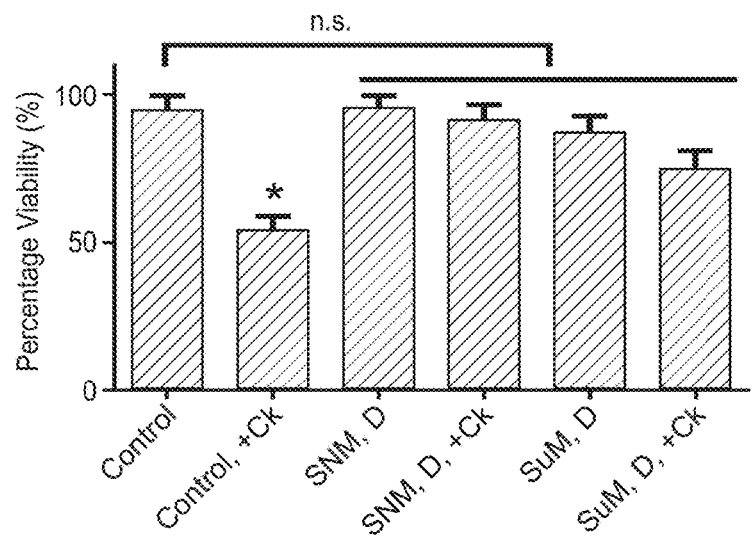
FIG. 28A
FIG. 28B
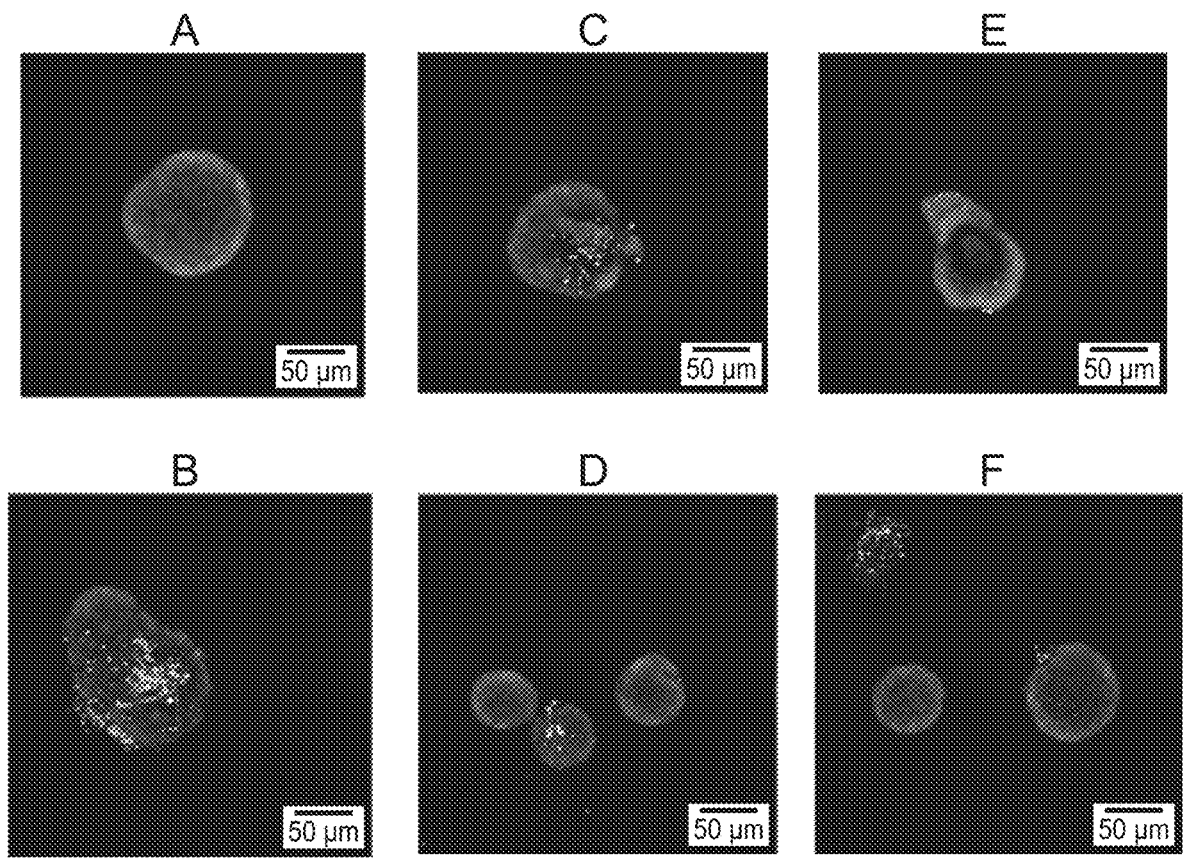

FIG. 29
| Experimental Condition | Low-High Glucose Stimulation ($10^{-2}$) | High-Low Glucose Shut-Down ($10^{-2}$) |
|---|---|---|
| SµM, Diff | 1.13 | -0.73 |
| SµM, Diff, +Ck | 1.15 | -1.46 |
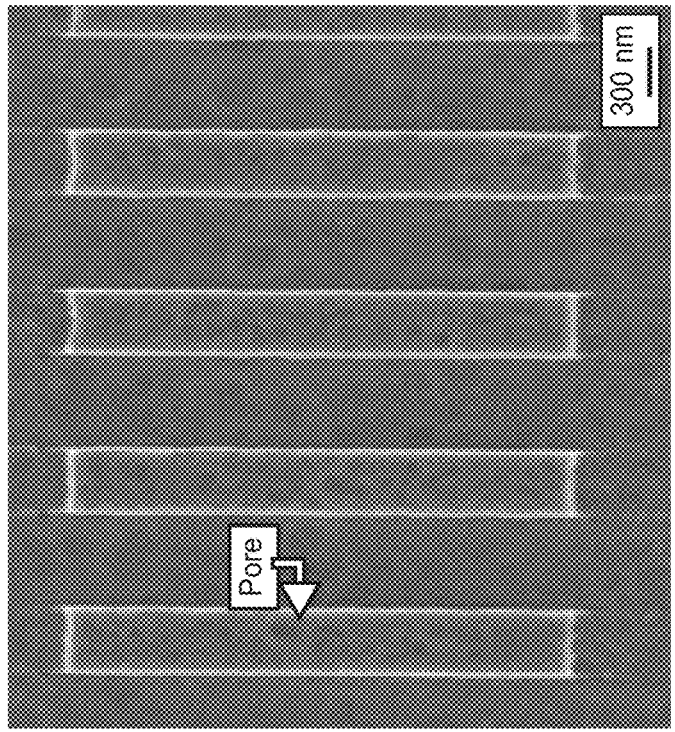
FIG. 30B
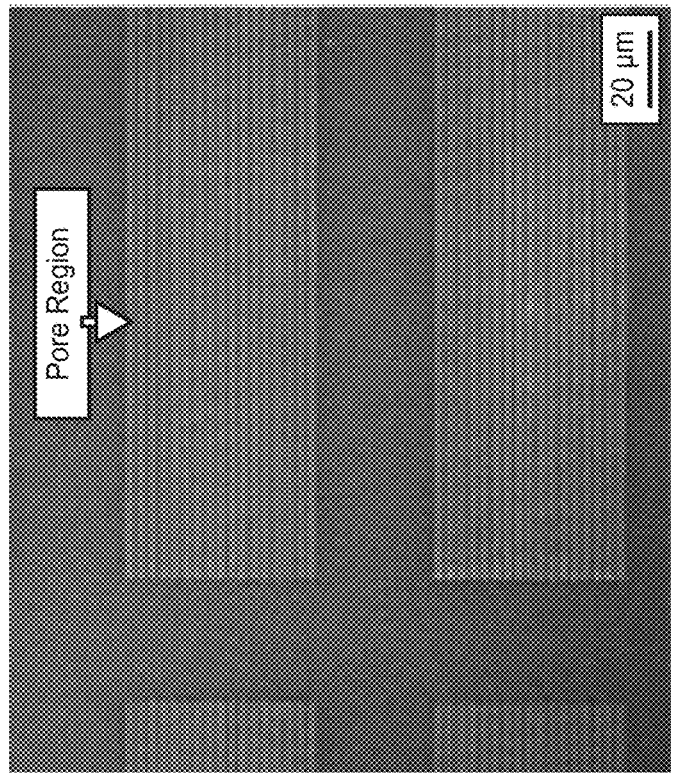
FIG. 30A FIG. 32A
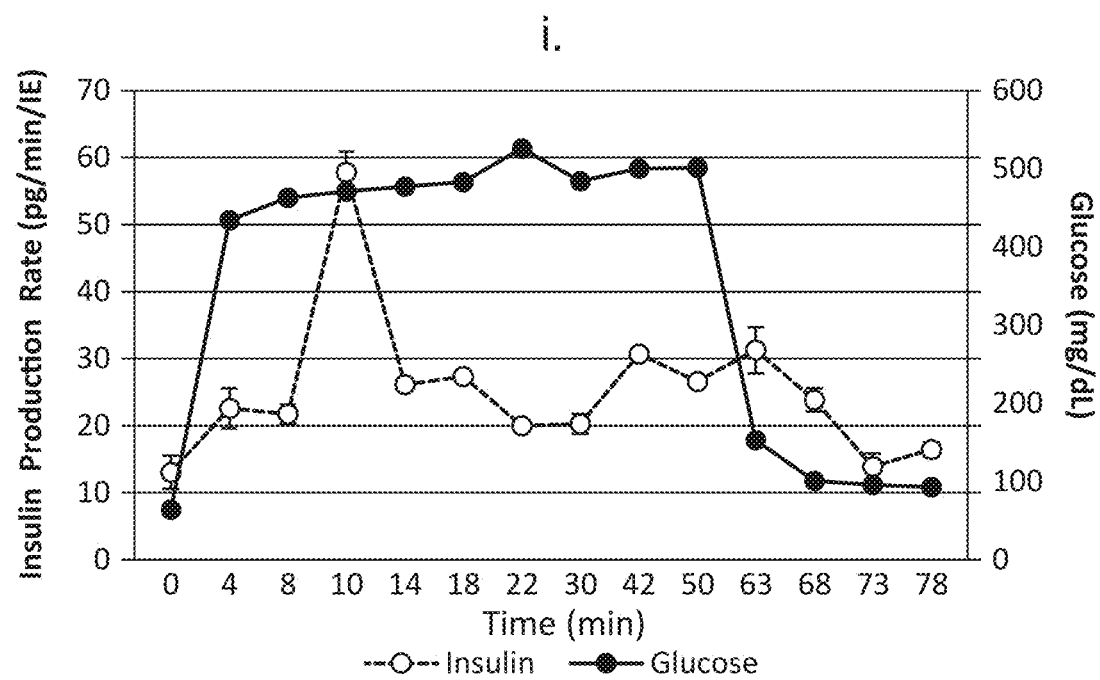
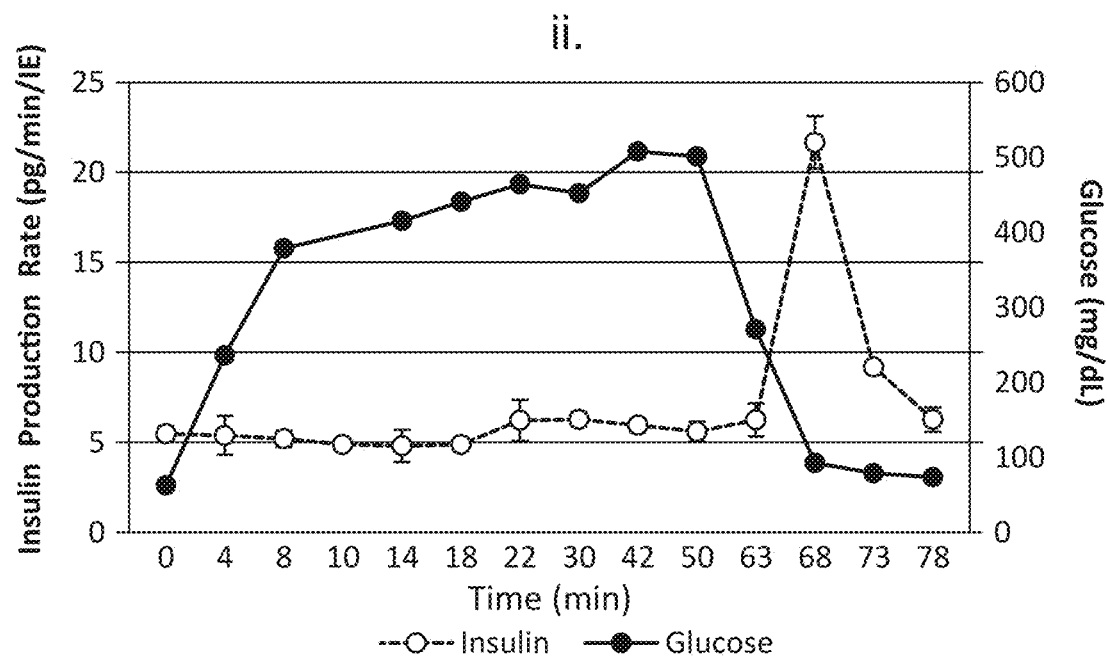

FIG. 33A
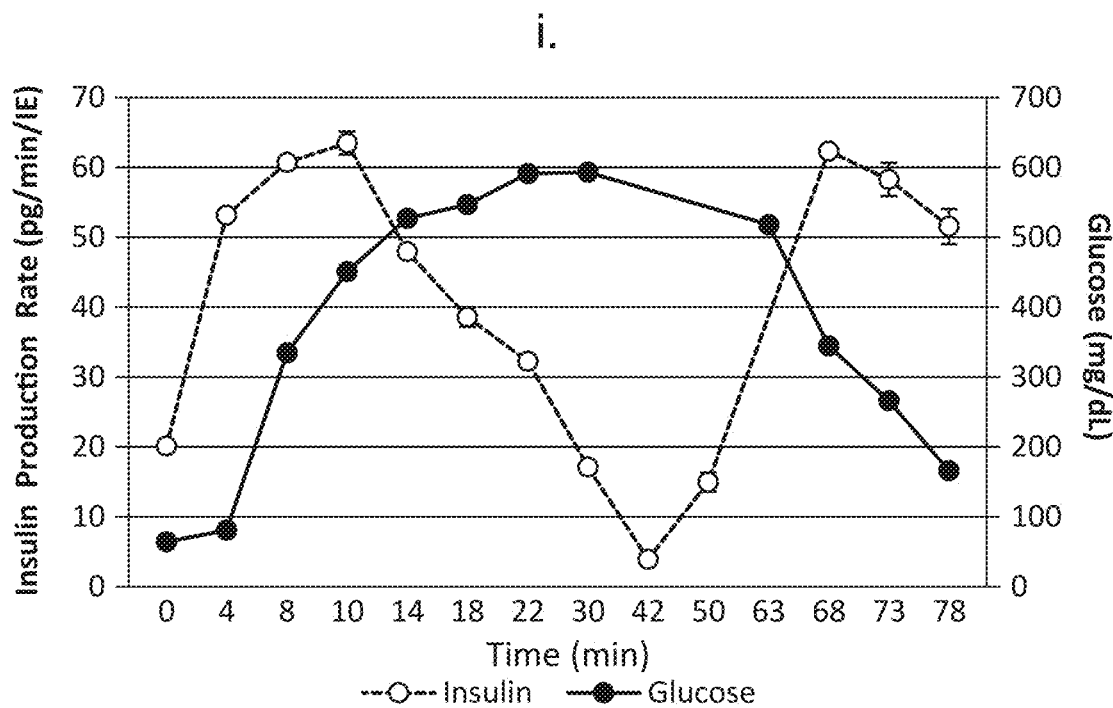
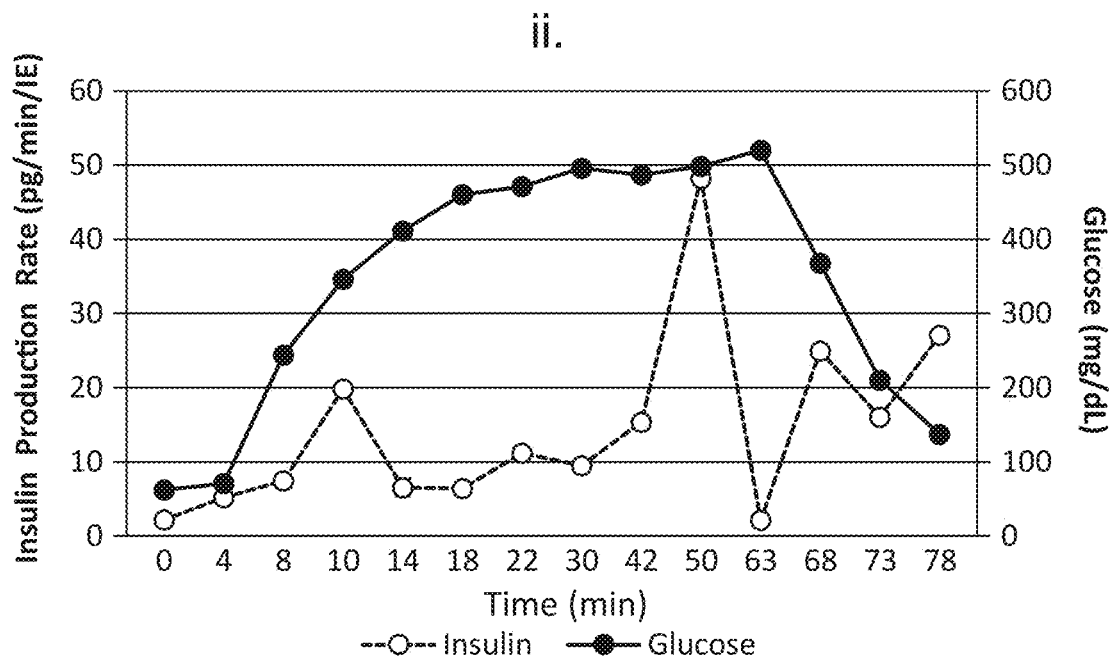

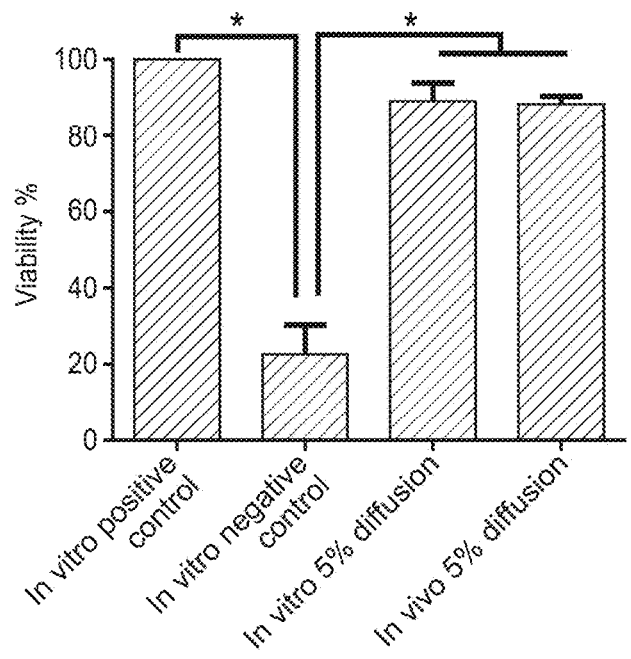
FIG. 34C
FIG. 34D
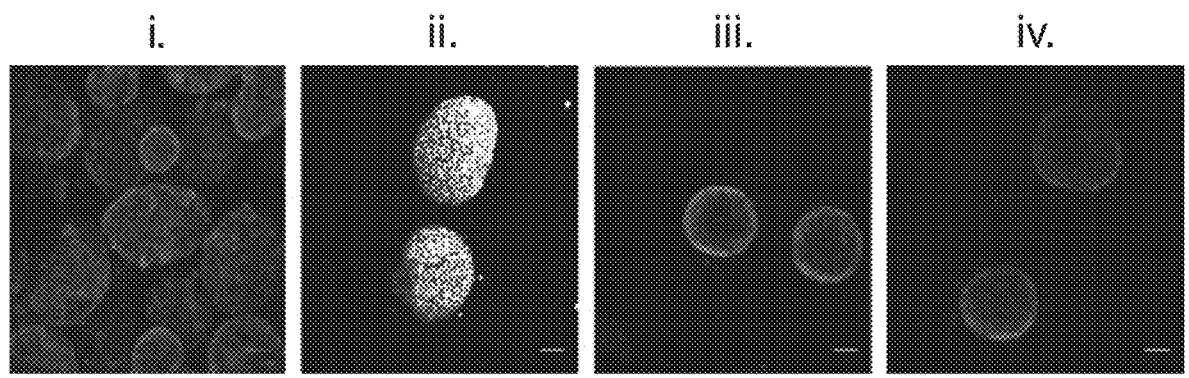

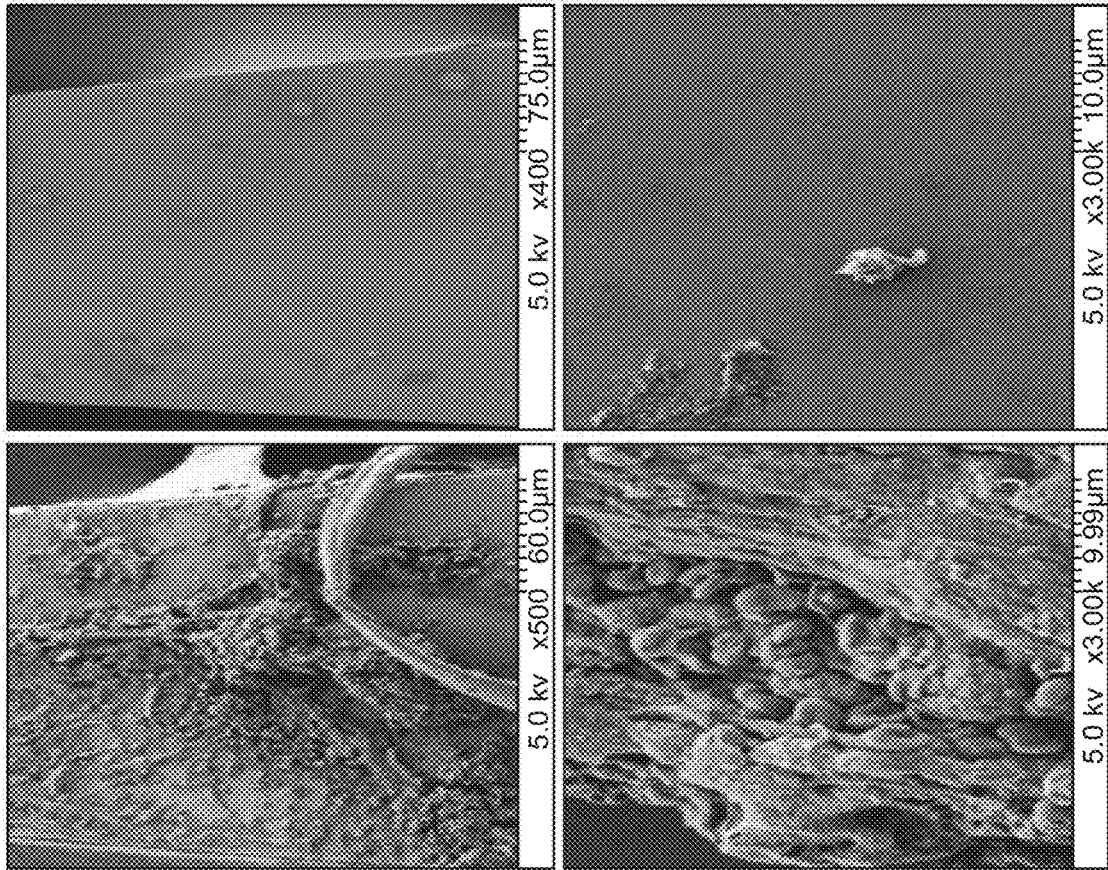

FIG. 46
| Cell Scaffold Features | Values |
| --- | --- |
| Cell Volume length and width | 200 - 600 µm |
| Cell Volume shape | Rectangular, circular, and oval |
| Fluid Channel length | 100 - 375 µm |
| Fluid Channel width | 10 - 100 µm |
| Fluid Channel Shape | Rectangular, circular, and oval |
| Cell Scaffold thickness | 500 - 2000 µm |
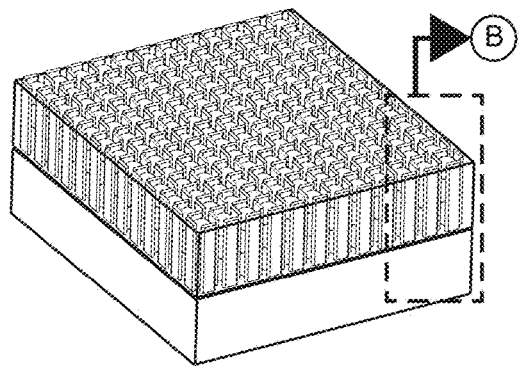
FIG. 47A
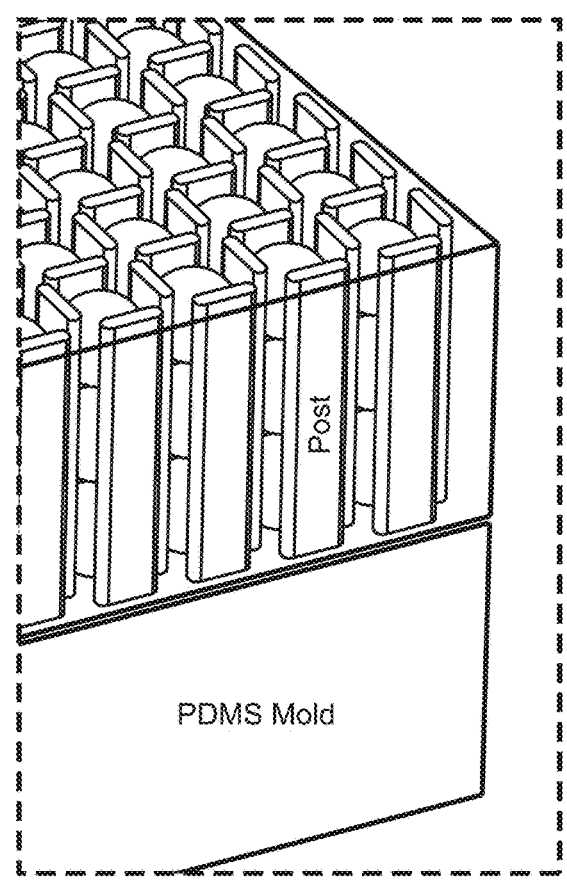
FIG. 47B

FIG. 50
| Islet Chamber Features | Values |
| --- | --- |
| Islet Volume length and width | 200 - 600 µm |
| Islet Volume shape | Rectangular, circular, and oval |
| Fluid Channel length | 100 - 375 µm |
| Fluid Channel width | 10 - 100 µm |
| Fluid Channel Shape | Rectangular, circular, and oval |
| Cell Scaffold thickness | 500 - 2000 µm |
FIG. 51
A  Pattern poly & grow thin oxide
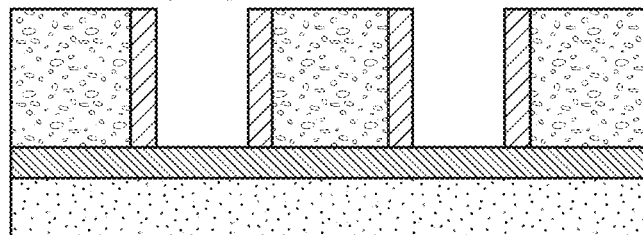
B  Deposit 2nd poly layer & planarize
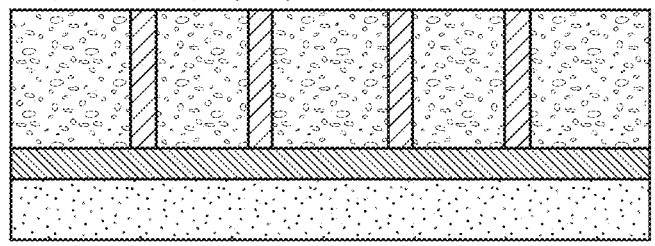
C  Etch windows & open pores
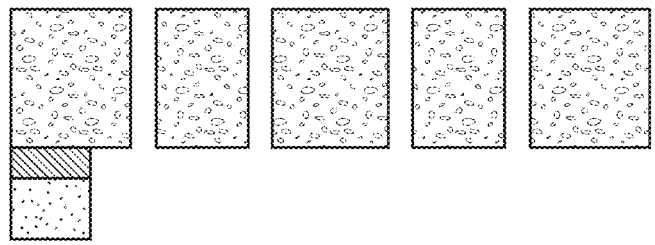

FIG. 56A
FIG. 56B
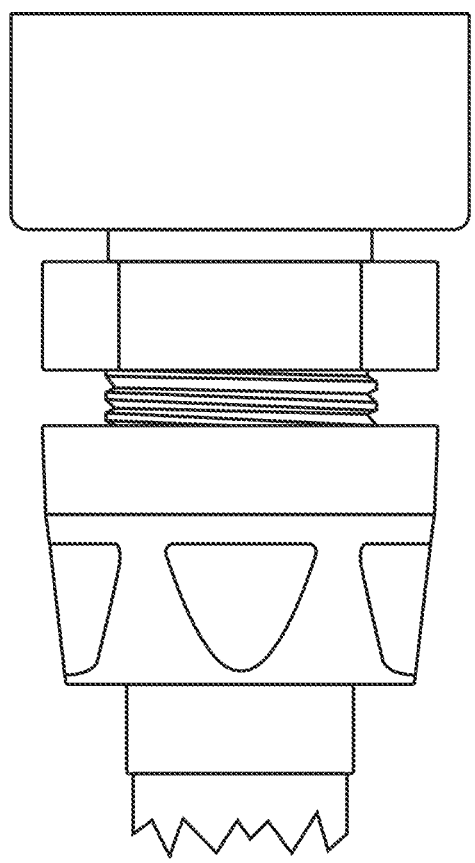
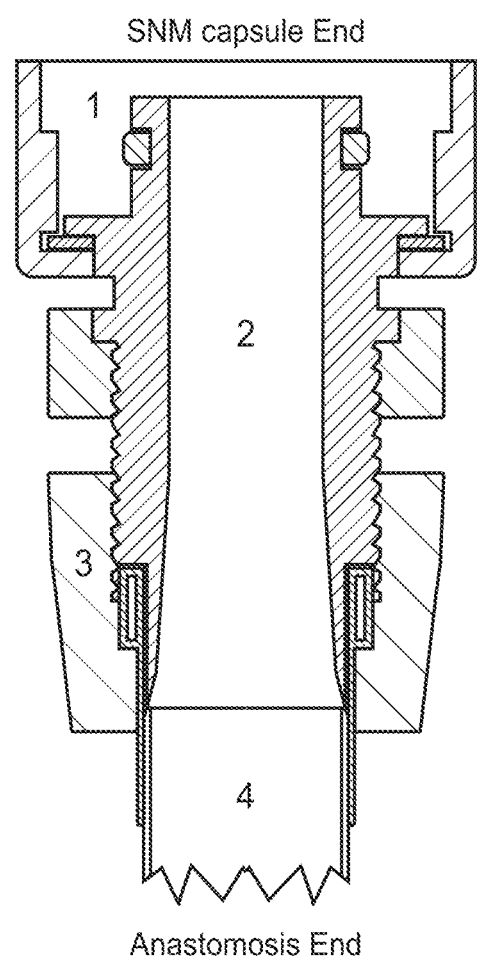
SNM capsule End
Anastomosis End

BIOARTIFICIAL ULTRAFILTRATION DEVICE AND METHODS RELATED THERETO

CROSS-REFERENCE TO RELATED APPLICATIONS

This application claims priority to U.S. application Ser. No. 16/082,501 filed Sep. 5, 2018, now issued as U.S. Pat. No. 11,033,668, which application claims priority to PCT Application No. US2017/021196 filed Mar. 7, 2017, which application claims priority to U.S. Provisional Application No. 62/304,758 filed Mar. 7, 2016 and to U.S. Provisional Application No. 62/328,298 filed Apr. 27, 2016, which provisional applications are both herein incorporated by reference in their entirety.

INTRODUCTION

Type 1 diabetes (T1D) results from autoimmune destruction of the insulin-producing β-cells within the pancreatic islets of Langerhans. Islet transplantation by direct infusion of cadaveric islets into the portal vein of the recipient's liver offers a non-invasive cure for patients with T1D mellitus 1. However, donor availability, poor engraftment, and side effects from global immunosuppression remain as obstacles for wider application of this approach. Moreover, up to 60% of the infused islets become nonviable within a few days after surgical delivery and the long-term insulin independence is frequently lost by 5 years of transplantation. The activation of innate and the adaptive immune responses are among the main causes of islet graft failure. The idea of encapsulating islets has generated tremendous interest. However, there is a need for improved devices and methods for providing encapsulated islets that maintain function and are protected from the patient's immune system.

SUMMARY

Bioartificial ultrafiltration devices for transplantation of cells in a subject are disclosed. These devices include a scaffold that encapsulates a population of cells while providing a plurality of channels adjacent the population of cells. In certain embodiments, a planar scaffold for facilitating exchange of molecules between a plurality of channels and cells adjacent the plurality of channels is disclosed. The planar scaffold may include a solid planar substrate comprising a first surface and a second surface; a void in the solid planar substrate, wherein the void extends from the first surface to the second surface; a matrix disposed in the void and extending from the first surface to the second surface, the matrix comprising: a plurality of channels extending from the first surface to the second surface, and a population of cells adjacent the plurality of channels.

In certain embodiments, the solid substrate has a thickness of 0.1 mm-10 mm, such as, 0.5 mm-5 mm, or 0.5 mm-3 mm and the first and second surfaces each have a surface area of 1 cm$^2$-100 cm$^2$. The matrix may have a surface area of 1 mm$^2$-10,000 mm$^2$, e.g., 1 mm$^2$-5000 mm$^2$, 1 mm$^2$-1000 mm$^2$, 1 mm$^2$-100 mm$^2$. In certain embodiments, the matrix comprises up to 25,000 channels. In certain embodiments, the channels comprise a width of 5 micron-1000 micron, e.g., a width of 10 micron-200 micron. In certain embodiments, the channels are circular and the width refers to diameter of the channels. In certain embodiments, the channels are rectangular. In certain embodiments, the length of the channels ranges from 100 micron to 1000 micron. In certain embodiments, a population of cells is separated from an adjacent channel by a distance of up to 500 microns or less, such as, 400 microns or less, or 300 microns or less. The population of cells may be insulin secreting cells. The population of cells may be pancreatic cells isolated from pancreatic islets, pancreatic islet cells, pancreatic beta cells, pancreatic islet cells, or cells in a pancreatic islet. Insulin secreting cells may be generated by differentiation of stem cells, such as, induced pluripotent stem cells (iPSCs).

The scaffold may include a semipermeable ultrafiltration membrane disposed on a first surface of the scaffold and covering the matrix on the first surface. In certain embodiments, a semipermeable ultrafiltration membrane may be disposed on a second surface of the scaffold and may be covering the matrix on the second surface. The semipermeable ultrafiltration membrane may be sized to immunoisolate the cells encapsulated in the matrix.

The planar scaffold may be used for culturing the population of cells, for example, for maintaining viability of the cells. The planar scaffold may be used for manufacturing a bioartificial ultrafiltration device as described herein.

In certain embodiments, the bioartificial ultrafiltration device may include a planar scaffold comprising a matrix comprising a population of cells and a plurality of channels adjacent to the population of cells, wherein the channels extend from a first surface to a second surface of the planar scaffold; a first semipermeable ultrafiltration membrane disposed on the first surface of the planar scaffold; a first compartment adjacent to the first surface of the planar scaffold and in fluidic communication with the planar scaffold via the first semipermeable ultrafiltration membrane and comprising an inlet and an outlet; a second compartment adjacent to the second surface of the planar scaffold and comprising an outlet, wherein the first semipermeable ultrafiltration membrane comprises a plurality of pores having a width in the range of 5 nm-5 micron, wherein the first semipermeable ultrafiltration membrane allows transport of ultrafiltrate from the first compartment to the plurality of channels and wherein the ultrafiltrate traverses from the plurality of channels into the second compartment.

In certain embodiments, the device may further include a second semipermeable ultrafiltration membrane disposed on the second surface of the planar scaffold and wherein the ultrafiltrate traverses from the plurality of channels across the second semipermeable ultrafiltration membrane into the second compartment. The second semipermeable ultrafiltration membrane may include a plurality of pores having a width in the range of 5 nm-5 micron. In certain embodiments, the first and second semipermeable ultrafiltration membranes may include a plurality of pores having a width in the range the range of 0.1 microns-2 microns.

In certain embodiments, the second semipermeable ultrafiltration membrane comprises a plurality of pores having a width larger than the width of the plurality of pores in the first semipermeable ultrafiltration membrane. In certain embodiments, the second semipermeable ultrafiltration membrane comprises a plurality of pores having a width smaller than the width of the plurality of pores in the first semipermeable ultrafiltration membrane.

In certain embodiments, the inlet of the first compartment is attachable to a conduit for connection to a blood vessel of a subject. In certain examples, this blood vessel may be an artery of the subject in whom the device is transplanted.

In certain embodiments, the outlet of the first compartment is attachable to a conduit for connection to a blood vessel of a subject. In certain examples, this blood vessel may be a vein or an artery of the subject. In certain cases, the outlet may be connect to an artery which may be the same artery as or different artery than the artery to which the inlet is connected.

In certain examples, the first compartment comprises a plurality of outlets that are each attachable to conduits for connection to (i) a plurality of different blood vessels of a subject or (ii) a plurality of connection sites on a single blood vessel.

In certain examples, the outlet of the second compartment is attachable to a conduit for connection to a blood vessel or a body cavity of a subject. In certain cases, the outlet of the second compartment provides the ultrafiltrate to one or more blood vessels or body cavity of the subject. In certain cases, the outlet of the second compartment is attachable to a tubing for connection to one or more veins of the subject. In other cases, the outlet of the second compartment is attachable to a tubing for connection to one or more arteries of the subject. In some cases, the outlet of the second compartment is attachable to an analyte analysis device. In yet other embodiments, the second compartment comprises a plurality of outlets for providing the ultrafiltrate to at least one blood vessel or a body cavity of the subject. In some cases, the second compartment comprises a plurality of outlets for providing the ultrafiltrate to an analyte analysis device.

In another embodiment, a bioartificial ultrafiltration device may include a first planar scaffold and a second planar scaffold each comprising a matrix comprising a population of cells and a plurality of channels adjacent the population of cells, wherein the channels extend from a first surface to a second surface of each of the planar scaffolds; a first semipermeable ultrafiltration membrane disposed on the first surface of the first and second planar scaffolds; a first compartment adjacent to and sandwiched between the first surface of the first and second planar scaffolds and comprising an inlet and an outlet, wherein the first semipermeable ultrafiltration membrane allows transport of ultrafiltrate from the first compartment to the scaffolds; a second compartment adjacent to the second surface of the first planar scaffold and comprising an outlet; a third compartment adjacent to the second surface of the second planar scaffold and comprising an outlet, wherein the first semipermeable ultrafiltration membrane comprises a plurality of pores having a width in the range of 5 nm-5 micron, and wherein the ultrafiltrate traverses from the plurality of channels in the scaffolds into the second compartment and the third compartment. In certain embodiments, the second semipermeable ultrafiltration membrane may include a plurality of pores having a width in the range of 5 nm-5 micron and wherein the second semipermeable ultrafiltration membrane is disposed on the second surface of the first and second planar scaffolds and wherein the ultrafiltrate traverses from the plurality of channels in the scaffolds into the second compartment and the third compartment via the second semipermeable ultrafiltration membrane.

In certain embodiments, the first semipermeable ultrafiltration membrane comprises a plurality of pores having a width in the range the range of 0.1 microns-2 microns. In certain embodiments, the second semipermeable ultrafiltration membrane comprises a plurality of pores having a width in the range the range of 0.1 microns-2 microns. In certain embodiments, the second semipermeable ultrafiltration membrane comprises a plurality of pores having a width larger than the width of the plurality of pores in the first semipermeable ultrafiltration membrane. In certain embodiments, the second semipermeable ultrafiltration membrane comprises a plurality of pores having a width smaller than the width of the plurality of pores in the first semipermeable ultrafiltration membrane.

In certain embodiments, the inlet of the first compartment is connectable to a conduit for connection to an artery of a subject. In certain embodiments, the outlet of the first compartment is connectable to a conduit for connection to an artery or a vein of a subject. In certain embodiments, the outlet of the second compartment is connectable to a conduit (e.g., a tubing) for connection to at least one blood vessel of a subject and/or to an analyte analysis device. In certain embodiments, the outlet of the third compartment is connectable to a tubing for connection to at least a blood vessel of a subject and/or to an analyte analysis device. In certain embodiments, the outlet of the third compartment is connectable to a tubing for connection to at least a vein of a subject and/or to an analyte analysis device. In certain embodiments, the outlet of the second compartment and the outlet of the third compartment are connected to a single tubing for connection to at least a blood vessel of a subject and/or to an analyte analysis device.

In certain embodiments, the plurality of pores in the first semipermeable membrane have a width in the range of 0.2 µm-0.5 µm and the plurality of pores in the second semipermeable membrane have a width in the range of 0.2 µm-0.5 µm. In certain embodiments, the thickness of the first semipermeable ultrafiltration membrane is in the range of 0.1 micron-1000 micron and the thickness of the second semipermeable ultrafiltration membrane is in the range of 0.1 micron-1000 micron.

In certain embodiments, the surface area of the first and second semipermeable ultrafiltration membrane is in the range of 1 $cm^2$-100 $cm^2$. In certain embodiments, the surface area of the first and second semipermeable ultrafiltration membrane is in the range 15 $cm^2$-30 $cm^2$.

As noted herein, the plurality of pores may be circular in shape and wherein the width refers to diameter of the pores. In some embodiments, the plurality of pores are slit-shaped and where the length of the pores is in the range of 0.1 micron-5 micron, e.g., 1 µm-3 µm.

The cells in the device may be insulin producing cells. For example, the insulin producing cells are derived from differentiation of stem cells or are pancreatic cells isolated from pancreatic islets. The cells may be autologous, allogenic, or xenogenic to the subject in whom the device will be transplanted.

A further embodiment of an bioartificial ultrafiltration device disclosed herein includes a planar scaffold comprising a matrix comprising a population of cells and a plurality of channels adjacent the population of cells, wherein the channels extend from a first surface to a second surface of the planar scaffold; a first semipermeable ultrafiltration membrane disposed on the first surface and a second semipermeable ultrafiltration membrane disposed on the second surface of the planar scaffold; a first compartment comprising a first inlet and a first outlet, wherein the first compartment is adjacent to the first surface of the planar scaffold; a second compartment comprising a second inlet and a second outlet, wherein the second compartment is adjacent to the second surface of the planar scaffold, wherein the first inlet is configured for connection to an artery of a subject and the first outlet is connected to the second inlet of the second compartment, wherein the second outlet of the second compartment is configured for connection to a vein of the subject, wherein the semipermeable ultrafiltration membranes comprise a plurality of pores having a width in the range of 5 nm-5 micron, wherein the first semipermeable ultrafiltration membrane allows transport of ultrafiltrate from the first compartment to the scaffold and the second semipermeable ultrafiltration membrane allows transport of the ultrafiltrate from the plurality of channels in the scaffold into the second compartment. The cells present in the device may insulin producing cells as described herein. In certain cases, the plurality of pores have a width in the range of 0.2 µm-0.5 µm.

In some embodiments, the plurality of pores in the second semipermeable ultrafiltration membrane have a width larger than the width of the plurality of pores in the first semipermeable ultrafiltration membrane. In some embodiments, the plurality of pores in the second semipermeable ultrafiltration membrane have a width smaller than the width of the plurality of pores in the first semipermeable ultrafiltration membrane.

In some embodiments, the thickness of the semipermeable ultrafiltration membranes is in the range of 0.1 micron-1000 micron, e.g., 200 µm-1000 µm. The surface area of the semipermeable ultrafiltration membrane is in the range of 1 cm$^2$-100 cm$^2$, e.g., 15 cm$^2$-30 cm$^2$.

As noted herein, the plurality of pores may be circular in shape and wherein the width refers to diameter of the pores.

In some embodiments, the plurality of pores are slit-shaped and wherein length of the pores is in the range of 1 micron-5 micron, e.g., 1 µm-3 µm.

Also disclosed herein are methods for transplanting the devices provided in the subject application into a patient. In certain cases, a method for providing a bioartificial ultrafiltration device comprising cells to a subject in need thereof includes connecting the bioartificial ultrafiltration device comprising a planar scaffold comprising a matrix comprising a population of cells and a plurality of channels adjacent to the population of cells, wherein the channels extend from a first surface to a second surface of the planar scaffold; a first semipermeable ultrafiltration membrane disposed on the first surface of the planar scaffold; a first compartment adjacent to the first surface of the planar scaffold and in fluidic communication with the planar scaffold via the first semipermeable ultrafiltration membrane and comprising an inlet and an outlet; a second compartment adjacent to the second surface of the planar scaffold and comprising an outlet, wherein the first semipermeable ultrafiltration membrane comprises a plurality of pores having a width in the range of 5 nm-5 micron, wherein the first semipermeable ultrafiltration membrane allows transport of ultrafiltrate from the first compartment to the plurality of channels and wherein the ultrafiltrate traverses from the plurality of channels into the second compartment, to the subject, wherein the connecting comprises connecting the inlet of the first compartment to an artery of the subject and connecting the outlet of the first compartment to a blood vessel of the subject; and connecting the outlet of the second compartment to a blood vessel or a body cavity of the subject; or connecting the outlet of the second compartment to an analyte analysis device.

In certain embodiments, a method for providing a bioartificial ultrafiltration device comprising cells to a subject in need thereof includes connecting the bioartificial ultrafiltration device comprising a first planar scaffold and a second planar scaffold each comprising a matrix comprising a population of cells and a plurality of channels adjacent the population of cells, wherein the channels extend from a first surface to a second surface of each of the planar scaffolds; a first semipermeable ultrafiltration membrane disposed on the first surface of the first and second planar scaffolds; a first compartment adjacent to and sandwiched between the first surface of the first and second planar scaffolds and comprising an inlet and an outlet, wherein the first semipermeable ultrafiltration membrane allows transport of ultrafiltrate from the first compartment to the scaffolds; a second compartment adjacent to the second surface of the first planar scaffold and comprising an outlet; a third compartment adjacent to the second surface of the second planar scaffold and comprising an outlet, wherein the first semipermeable ultrafiltration membrane comprises a plurality of pores having a width in the range of 5 nm-5 micron, and wherein the ultrafiltrate traverses from the plurality of channels in the scaffolds into the second compartment and the third compartment, to the subject, wherein the connecting comprises connecting the inlet of the first compartment to an artery of the subject and connecting the outlet of the first compartment to a blood vessel of the subject; and connecting the outlets of the second and third compartments to a blood vessel or body cavity of the subject; or connecting the outlets of the second and third compartments to an analyte analysis device; or connecting the outlet of the second compartment to a blood vessel or a body cavity of the subject and connecting the outlet of the third compartment to an analyte analysis device; or connecting the outlet of the second compartment to an analyte analysis device and connecting the outlet of the third compartment to a second vein of the subject.

In another embodiment, a method for providing a bioartificial ultrafiltration device comprising cells to a subject in need thereof includes connecting the bioartificial ultrafiltration device comprising a planar scaffold comprising a matrix comprising a population of cells and a plurality of channels adjacent the population of cells, wherein the channels extend from a first surface to a second surface of the planar scaffold; a first semipermeable ultrafiltration membrane disposed on the first surface and a second semipermeable ultrafiltration membrane disposed on the second surface of the planar scaffold; a first compartment comprising a first inlet and a first outlet, wherein the first compartment is adjacent to the first surface of the planar scaffold; a second compartment comprising a second inlet and a second outlet, wherein the second compartment is adjacent to the second surface of the planar scaffold, wherein the first inlet is configured for connection to an artery of a subject and the first outlet is connected to the second inlet of the second compartment, wherein the second outlet of the second compartment is configured for connection to a vein of the subject, wherein the semipermeable ultrafiltration membranes comprise a plurality of pores having a width in the range of 5 nm-5 micron, wherein the first semipermeable ultrafiltration membrane allows transport of ultrafiltrate from the first compartment to the scaffold and the second semipermeable ultrafiltration membrane allows transport of the ultrafiltrate from the plurality of channels in the scaffold into the second compartment, to the subject, wherein the connecting comprises connecting the first inlet to an artery of a subject; and connecting the second outlet to a vein of the subject.

In some embodiments, the method comprises providing insulin to the subject and wherein the cells comprise insulin producing cells. In some cases, the insulin producing cells are derived from differentiation of stem cells or are pancreatic cells such as, pancreatic beta cells isolated from pancreatic islets. In some examples, the cells are islet cells, for example, the cells may be present in islets isolated from pancreas. The cells may be autologous, allogenic, or xenogenic to the subject. In certain embodiments, connecting the bioartificial device to the subject in need thereof results in increased viability of the cells in the scaffold. In certain embodiments, the ultrafiltrate comprises one or more of glucose and oxygen. In certain embodiments, the ultrafiltrate comprises one or more of glucose and oxygen and wherein the insulin producing cells excrete insulin in response to presence of glucose in the ultrafiltrate and wherein the plurality of channels transport the insulin to the second compartment and/or to the third compartment. In certain embodiments, the excreted insulin is transported to the plurality of channels in the scaffold.

In certain embodiments, the semipermeable ultrafiltration membranes reduce or prevent the passage of immune system components into the scaffold, e.g., passage of antibodies into the scaffold, passage of cytokines (e.g., TNF-α, IFN-γ, and/or IL-1β) into the scaffold.

BRIEF DESCRIPTION OF THE DRAWINGS

FIGS. 2A-2I show a schematic for fabrication of silicon nanopore membranes.

FIGS. 3A-3E show in vitro viability of mouse islets under cytokine exposure.

FIGS. 14A-14C show glucose-insulin kinetics of SNM- and silicon micropore membrane (SμM)-encapsulated islets under convection without cytokine exposure.

FIGS. 15A-15C show glucose-insulin kinetics of SNM-encapsulated islets under convection and diffusion with cytokine exposure.

FIGS. 17A-17B show in-vitro viability of mouse islets.

FIG. 18 shows the rate of change in insulin secretion without cytokine exposure in Table 1.

FIG. 19 shows the rate of change in insulin secretion with cytokine exposure in Table 2.

FIGS. 24A-24C show glucose-insulin kinetics of SμM-encapsulated islets under convection and diffusion without cytokine exposure.

FIGS. 27A-27C show glucose-insulin kinetics of SNM- and SμM-encapsulated islets under diffusion with cytokine exposure.

FIGS. 28A-28B show in-vitro viability of mouse islets.

FIG. 29 shows the rate of change in insulin secretion as depicted in the table.

FIGS. 30A-30B show SEM images of the pore-containing regions surrounded by solid silicon regions.

FIGS. 32A-32C shows in vitro testing of the intravascular bioartificial pancreas device (iBAP) with 10% or 20% islet density encapsulated with 10 nm-pore size SNM.

FIGS. 33A-33C shows in vitro testing of the intravascular bioartificial pancreas device (iBAP) with 10% or 20% islet density encapsulated with 40 nm-pore size SNM.

FIGS. 34A-34D shows in vivo testing of the intravascular bioartificial pancreas device (iBAP) with 5% islet density encapsulated with 10 nm-pore size SNM for 3 days.

FIG. 39 shows silicon nanopore membrane (SNM) hydraulic permeability as a function of pore size.

FIG. 40 shows SEM images of uncoated (left) and PEG-coated (right) silicon surfaces at low (top) and high (bottom) magnification after 30 days of blood exposure in vivo in femoral vessels of anticoagulant free rodents.

FIG. 45A shows an isometric view of a 6 mm×6 mm×1.2 mm Islet Chamber that will be placed within the SNM support structure cavity. FIG. 45B shows a close up of the Islet Chamber corner with the Fluid Channel (FC) and the direction of ultrafiltrate flow. FIG. 45C illustrates a top view of the Islet Chamber's Islet Volume (IV), Structural Volume (SV) and FC regions labeled along with dimensions.

FIG. 46 shows cell scaffold design features to optimize.

FIGS. 47A-47B show views of a PDMS mold. FIG. 47A shows an isometric view of a 6 mm×6 mm×1.2 mm PDMS positive mold with cells/hydrogel mixture. FIG. 47B shows a close up where the PDMS posts and structural base are gray, the cells are green, and the hydrogel is a translucent purple.

FIG. 50 shows Islet Chamber design features to optimize.

FIG. 51 shows the process flow used to fabricate SNM.

FIGS. 56A-56B show a schematic of a connector for connecting a graft to a device as disclosed.

DEFINITIONS

Figure 1A:
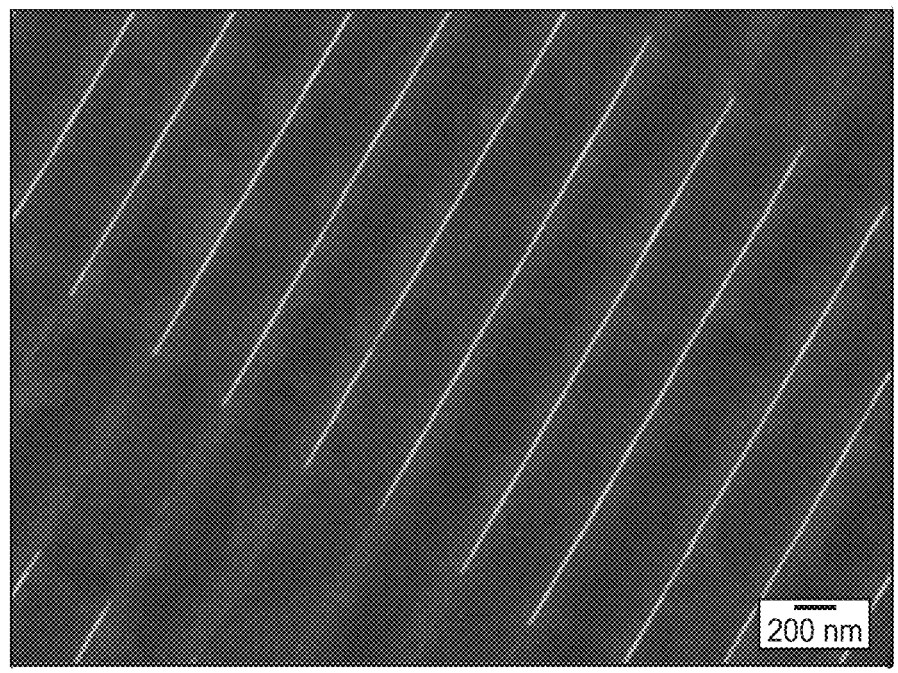
FIGS. 1A-1B show silicon nanoporous membranes (SNM).

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

As used herein, the term "filtration" refers to a process of separating particulate matter from a fluid, such as air or a liquid, by passing the fluid carrier through a medium (e.g., a semipermeable membrane) that will not pass the particulates.

As used herein, the term "ultrafiltration" refers to subjecting a fluid to filtration, where the filtered material is very small; typically, the fluid comprises colloidal, dissolved solutes or very fine solid materials, and the filter is a microporous or nanoporous. The filter may be a membrane, such as, a semi-permeable membrane. The fluid to be filtered is referred to as the "feed fluid." In certain embodiments, the feed fluid may be arterial blood. During ultrafiltration, the feed fluid is separated into a "permeate" or "filtrate" or "ultra-filtrate," which has been filtered through the filter, and a "retentate," which is that part of the feed fluid which did not get filtered through the membrane.

As used herein the terms "subject" or "patient" refers to a mammal, such as, a primate (e.g., humans or non-human primates), a bovine, an equine, a porcine, a canine, a feline, or a rodent. In certain embodiments, the subject or patient may be a human. In certain embodiments, the subject or patient may be pre-diabetic or may have diabetes, such as, type 1 diabetes (T1D) or type 2 diabetes. The terms "subject" and "patient" are used interchangeably herein.

As used herein, the terms "treat," "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

As used herein, the terms "layer", "film", or "membrane" and plurals thereof as used in the context of a device of the present disclosure refer to an individual layer of the device that may be formed from a silicon membrane, silicon nitride, silica, atomically thin membrane such as graphene, silicon, silicene, molybdenum disulfide ($MoS_2$), etc., or a combination thereof or a polymer. The "layer", "film", or "membrane" used to manufacture a porous layer of the present disclosure is typically porous and can be nanoporous or microporous. The phrases "nanoporous layer," "nanopore layer," "nanoporous membrane," "nanopore membrane," "nanoporous film," and "nanopore film" are used interchangeably and all refer to a polymer layer in which nanopores have been created. A nanoporous layer may include a frame for supporting the layer. The phrases "microporous layer," "micropore layer," "microporous membrane," "micropore membrane," "microporous film," and "micropore film" are used interchangeably and all refer to a polymer layer in which micropores have been created. A microporous layer may include a frame for supporting the layer.

As used herein, the term "encapsulated" as used in the context of cells disposed in a matrix of a scaffold as described herein. The scaffold may be included into the devices provided herein. The cells may be encapsulated in a matrix that includes a plurality of channels adjacent the encapsulated cells. The cells may be encapsulated in a matrix that includes a biocompatible polymerizable polymer.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "channels" includes a plurality of such channels and reference to "the agarose-cell region" includes reference to one or more agarose-cell regions and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

As summarized above, bioartificial ultrafiltration devices comprising a population of cells is disclosed. Also described herein are methods for making the devices and methods of using the devices. The bioartificial devices provided herein may be used for providing an ultrafiltrate produced by filtration of blood across a semipermeable porous membrane. The ultrafiltrate may be provided to the population of cells and may provide nutrients, such as, oxygen and glucose to the cells. The ultrafiltrate may take up molecules secreted by the cells such as insulin and other metabolites and the ultrafiltrate may be returned to the blood. The ultrafiltrate may be enclosed in channels which are surrounded by the cells thereby increasing the rate of exchange of molecules. The devices of the present disclosure can have a variety of configurations and uses. The following sections provide a detailed description of various embodiments and uses of the device disclosed herein.

Cell Scaffold

Provided herein are scaffolds that support a population of cells encapsulated in a matrix. In certain embodiments, the planar scaffold is three-dimensional and includes a first surface opposite a second surface. The planar scaffold may be include a sheet of a solid substrate in which a void has been created which void contains a matrix that supports the population of cells and a plurality of channels.

The solid substrate may be composed of any suitable material, such as, a polymer, such as a biocompatible polymer. Non-limiting examples of materials for the solid substrate region of the scaffold can be found in U.S. Pat. No. 9,132,210, which is herein incorporated by reference in its entirety. Non-limiting examples of materials for the solid substrate region of the scaffold: polylactic acid, polyglycolic acid, PLGA polymers, polyesters, poly(allylamines)(PAM), poly(acrylates), modified styrene polymers, pluronic polyols, polyoxamers, poly(uronic acids), poly(vinylpyrrolidone), alginate, polyethylene glycol, fibrin, and poly (methyl methacrylate) and copolymers or graft copolymers of any of the above. In certain embodiments, the solid substrate of the scaffold is composed of acrylate. In certain embodiments, the acrylate is in the form of an acrylate sheet.

In certain embodiments, the solid substrate may be laser-cut to create a void. In certain embodiments, a sheet of the solid substrate is laser-cut to create a void region. In certain embodiments, a sheet of the solid substrate is laser-cut to create two or more void regions which may be cut into individual pieces. The void or cut-out may have any shape, such as, square, or rectangular with edges that are substantially straight or undulating, or circular with substantially smooth periphery. The void may be of a size sufficient to contain a plurality of channels and a population of cells adjacent the plurality of channels. The size of the void may be proportional to the size of the device. In certain cases, the solid surface may be have a thickness of 0.1 mm-10 mm, such as, 0.5 mm-5 mm, or 0.5 mm-3 mm and may be in shape of a cube or a cuboid and the surface area of the first surface and the second surface may 1 $cm^2$-200 $cm^2$, e.g., 1 $cm^2$-100 $cm^2$, 1 $cm^2$-50 $cm^2$, 1 $cm^2$-25 $cm^2$, or 5 $cm^2$-50 $cm^2$. The matrix may have a surface area of 1 $mm^2$-10,000 $mm^2$, e.g., 1 $mm^2$-5000 $mm^2$, 1 $mm^2$-1000 $mm^2$, 1 $mm^2$-100 $mm^2$. In certain cases the void may have a surface area of 100 $cm^2$ or less such as, 15 $cm^2$ or less, 10 $cm^2$ or less, 5 $cm^2$ or less, 1 $cm^2$ or less, 0.5 $cm^2$ or less, for example, 20 $cm^2$-0.5 $cm^2$, 15 $cm^2$-0.3 $cm^2$, 10 $cm^2$-0.5 $cm^2$, 5 $cm^2$-0.5 $cm^2$, or 1 $cm^2$-0.5 $cm^2$. The depth of the void and the matrix disposed therein is determined by the thickness of the solid substrate used to form the scaffold and may be in the range of 200 micron to 1000 micron, such as, 200 micron-900 micron, 200 micron-800 micron, 300 micron-700 micron, 200 micron-700 micron, or 300 micron-600 micron. In certain embodiments, the void may have a dimension of about 1-5 mm (length)×1-5 mm (width)×0.5-1 mm (depth), e.g., 1 mm×3 mm×1 mm, 2 mm×3 mm×1 mm, 3 mm×3 mm×1 mm, or 4 mm×4 mm×1 mm.

In certain embodiments, the planar scaffold comprises a matrix. In certain embodiments, the matrix comprises a plurality of channels and a population of cells. In certain embodiments, the matrix is formed by disposing a plurality of elongate posts into the void where the elongate posts are oriented in a direction perpendicular to the first and second surfaces of the solid substrate in which the void was created. In certain embodiments, the elongate posts may be tubes or wires, such as, polytetrafluorethylene (PFTE) coated wires. In certain embodiments, the elongate posts may be substantially cylindrical in shape. The diameter of the elongate posts may range from 25 micron-500 micron, such as, 50 micron-500 micron, 50 micron-300 micron, 50 micron-200 micron, 75 micron-200 micron, 75 micron-150 micron, e.g., 100 μm in diameter. In other cases, the elongate posts may have a rectangular shape or an irregular shape. The matrix may be formed from a polymerizable biocompatible polymer that support viability of the encapsulated cells. For example, the matrix may enable transport of molecules (e.g., glucose, oxygen, insulin) to and from the cells. In certain embodiments, the matrix comprises a polylactic acid, polyglycolic acid, polyethylene glycol (PEG), polylactic-co-glycolic acid) (PLGA) polymer, alginate, alginate derivative, gelatin, collagen, fibrin, agarose, hyaluronic acid, hydrogel, matrigel, natural polysaccharide, synthetic polysaccharide, polyamino acid, polyester, polyanhydride, polyphosphazine, poly(vinyl alcohol), poly(alkylene oxide), modified styrene polymer, pluronic polyol, polyoxamer, poly(uronic acid), or poly(vinylpyrrolidone) polymer. In certain embodiments, the matrix is includes an agarose polymer, an extracellular matrix, hydrogel, matrigel, or a mixture thereof. In certain embodiments, the matrix further includes a population of cells. In certain embodiments, the matrix is formed by disposing a composition comprising an unpolymerized polymer and a population of cells as disclosed herein into the void region of the solid substrate of the scaffold, which void regions include the elongate posts. The composition is then polymerized and the elongate posts removed to provide a matrix that includes the population of cells and a plurality of channels created by removal of the wires. In certain embodiments, the plurality channels are cylindrical shaped channels. In certain embodiments, the channels are rectangular, cylindrical, or square shaped. In certain embodiments, the channels are at least 20 μm, 30 μm, 40 μm, 50 μm, 60 μm, 70 μm, 80 μm, 90 μm, 100 μm, 110 μm, 120 μm, 130 μm, 140 μm, or 150 μm in diameter. In certain embodiments, the channels 30-200 μm or 50-150 μm in diameter. In certain embodiments, the channels extend from a first surface to a second surface of the planar scaffold. The matrix may include two or more channels, such as, 3-25,000, 5-10,000, 10-10,000, 30-10,000, 50-10,000, 100-10,000, 1000-10,000, 100-3000, 3-100, 3-70, 3-50, 3-25, 3-20, 5-100, 6-75, 7-50, or 8-20 channels where the channels are adjacent a population of cells. The matrix is configured such that a channel is separated by a distance less than 500 μm from a cell in order to facilitate efficient exchange of molecules between the ultrafiltrate in the channel and the cell.

In certain embodiments, the scaffold includes a plurality of channels where at least one of the channels is surrounded by a hexagonal arrangement of the cells. In certain embodiments, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, or at least twenty channels are surrounded by a hexagonal arrangement of the cells. In certain embodiments, the cells are adjacent at least one of the plurality of channels such that the cells are separated from the channel by a distance less than 500 micron, such as, 400 micron, 300 micron, or 200 micron. The presence of cells adjacent to the channels facilitates diffusion of molecules 500 micron from at least one channel. In certain embodiments, the matrix includes a configuration of a channel surrounded by a hexagonal cluster of cells. In certain embodiments, the scaffold may include a cell density of at least 5% by volume, 10% (5,700 cell equivalents/cm$^2$), 20% (11,400 cell equivalents/cm$^2$) or more. The number of cells in the matrix of the bioartificial device may vary and may be determined empirically. In some cases, the scaffold may include at least $10^3$ cells, $10^5$ cells, $10^6$ cells, $10^{10}$ cells, such as $10^3$-$10^{10}$ cells, $10^5$-$10^8$ cells, $10^3$-$10^6$ cells, or $10^5$-$10^6$ cells. In certain embodiments, the matrix includes a plurality of channels surrounded by a population of cells, where the diameter of the channel-cell region is 100 μm, 200 μm, 300 μm, 400 μm, 500 μm, 600 μm, 700 μm, 800 μm, 900 μm, or 1000 μm, e.g., in the range of 800 μm-1000 μm in diameter. In certain embodiments, the scaffold includes eight 800 μm channel-cell regions with eight 100 μm diameter cylindrical channels. The scaffold thus includes a matrix in which the cells are encapsulated following polymerization of the composition containing the mixture of unpolymerized polymer and cells.

Figure 45A:
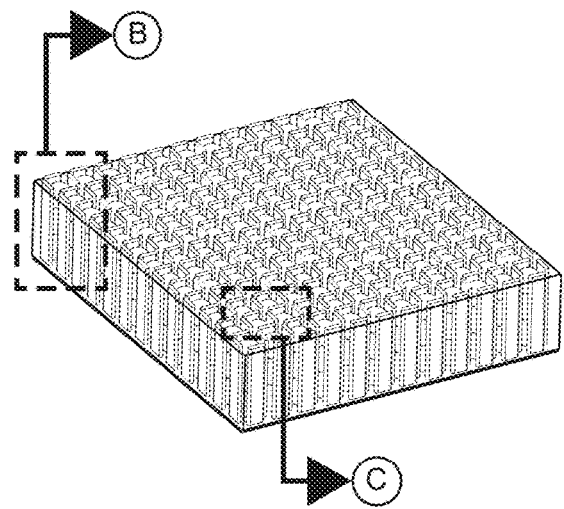
FIGS. 45A-45C show the structural layout of the Islet Chamber.
Figure 45B:
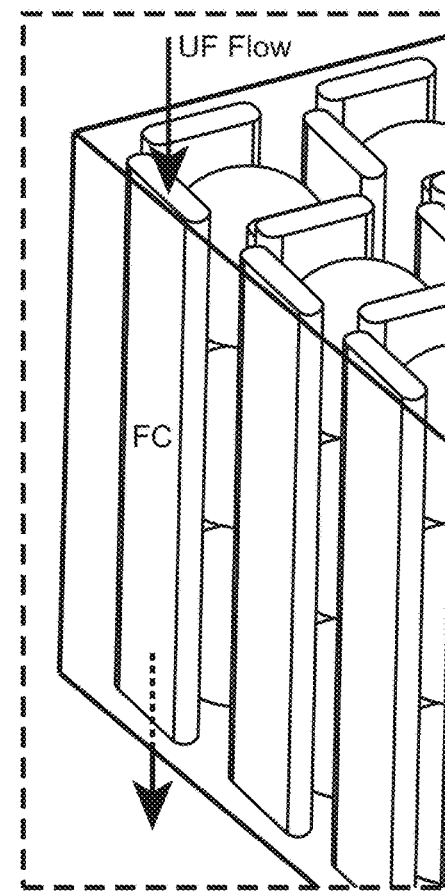
Figure 45C:
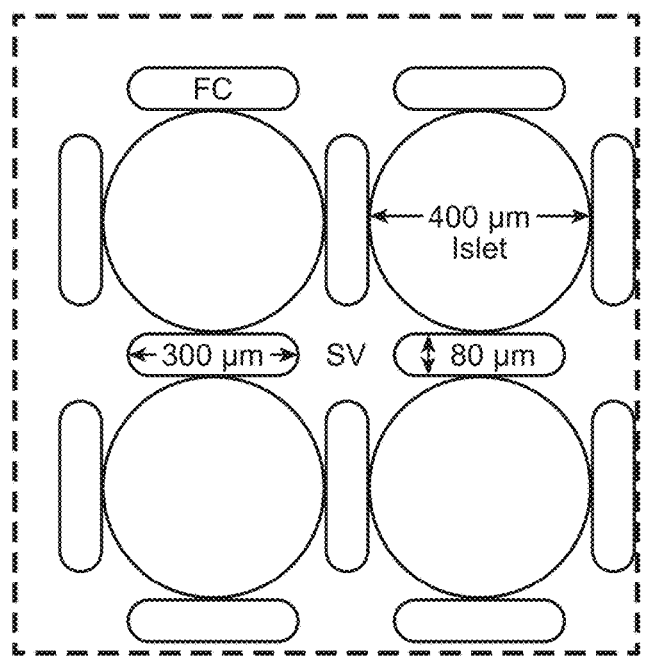

In certain cases, the matrix supported in a planar scaffold may be configured as depicted in FIGS. 45A-C. FIG. 45A shows an isometric view of a 6 mm×6 mm×1.2 mm matrix that will be placed within the planar scaffold cavity. FIG. 45B shows a close up of the matrix corner with a plurality of fluid channels (FC) and the direction of ultrafiltrate flow. FIG. 45C illustrates a top view of the Islet Chamber's Islet Volume (IV), Structural Volume (SV) and FC regions labeled along with dimensions.

In certain cases, the matrix of insulin secreting cells (referred to as islet cells) may be configured according to the arrangement depicted in FIG. 47 with dimensions as listed in FIG. 46. For example, the insulin secreting cells may be encapsulated in a matrix having a thickness of 500-2000 micron and the matrix may include a defined configuration of a periodic arrangement of channels for the flow of ultrafiltrate, wherein the channels may traverse the thickness of the matrix and may have a width of 10-100 micron.

Populations of cells that can be included in the devices described herein include but are not limited to, bone marrow cells; mesenchymal stem cells, stromal cells, pluripotent stem cells (e.g., induced pluripotent stem cells or embryonic stem cells), blood vessel cells, precursor cells derived from adipose tissue, bone marrow derived progenitor cells, intestinal cells, islets, Sertoli cells, beta cells, progenitors of islets, progenitors of beta cells, peripheral blood progenitor cells, stem cells isolated from adult tissue, retinal progenitor cells, cardiac progenitor cells, osteoprogenitor cells, neuronal progenitor cells, and genetically transformed cells, or a combination thereof. The population of cells may be from the subject (autologous cells), from another donor (allogeneic cells) or from other species (xenogeneic cells). The cells can be introduced into the scaffold and the scaffold may be immediately (within a day) implanted into a subject or the cells may cultured for longer period, e.g. greater than one day, to allow for cell proliferation prior to implantation.

In certain embodiments, the populations of cells in the matrix are stem cells. In certain embodiments, the population of cells in the matrix are pancreatic progenitor cells. In certain embodiments, the population of cells in the matrix are pancreatic cells isolated from islets of pancreas. In certain embodiments, the population of cells in the matrix are islets isolated from pancreas. In certain embodiments, the population of cells in the matrix may be in the form of a piece of tissue, such as, islet of Langerhans, which may have been isolated from the subject receiving the device or from another subject.

In certain embodiments, the devices disclosed herein may be used to treat a person having diabetes, such as, type 1 diabetes. The device may include pancreatic islet cells or may include stem cells that are capable of differentiating into insulin producing pancreatic cells. In certain embodiments, pluripotent stem cells (PSCs) may be differentiated into insulin producing pancreatic cells inside the device and then the bioartificial device containing the differentiated insulin producing pancreatic cells is placed in the subject (e.g., in the omentum, adjacent to pancreas or liver, adjacent to kidney, lung, or heart, or subdermally, e.g., in arm or abdomen). In some case, the device may include PSCs and the device may be implanted adjacent the pancreas or liver of the subject.

Bioartificial Ultrafiltration Device

In certain embodiments, the bioartificial device may include a planar scaffold described herein, e.g., a planar scaffold that includes a matrix comprising a population of cells and a plurality of channels adjacent to the population of cells, wherein the channels extend from a first surface to a second surface of the planar scaffold; a first semipermeable ultrafiltration membrane disposed on the first surface of the planar scaffold; a first compartment adjacent to the first surface of the planar scaffold and in fluidic communication with the planar scaffold only via the first semipermeable ultrafiltration membrane and comprising an inlet and an outlet; a second compartment adjacent to the second surface of the planar scaffold and comprising an outlet, wherein the first semipermeable ultrafiltration membrane comprises a plurality of pores having a width in the range of 5 nm-5 micron, wherein the first semipermeable ultrafiltration membrane allows transport of ultrafiltrate from the first compartment to the plurality of channels and wherein the ultrafiltrate traverses from the plurality of channels into the second compartment.

In certain embodiments, the bioartificial device may include two planar scaffolds which sandwich a compartment containing arterial blood. For example, the device may include a first planar scaffold and a second planar scaffold each comprising a matrix comprising a population of cells and a plurality of channels adjacent the population of cells, wherein the channels extend from a first surface to a second surface of each of the planar scaffolds; a first semipermeable ultrafiltration membrane disposed on the first surface of the first and second planar scaffolds; a first compartment adjacent to and sandwiched between the first surface of the first and second planar scaffolds and comprising an inlet and an outlet, wherein the first semipermeable ultrafiltration membrane allows transport of ultrafiltrate from the first compartment to the scaffolds; a second compartment adjacent to the second surface of the first planar scaffold and comprising an outlet; a third compartment adjacent to the second surface of the second planar scaffold and comprising an outlet, wherein the first semipermeable ultrafiltration membrane comprises a plurality of pores having a width in the range of 5 nm-5 micron, and wherein the ultrafiltrate traverses from the plurality of channels in the scaffolds into the second compartment and the third compartment.

Aspects of the present disclosure include a bioartificial device that includes a planar scaffold comprising a matrix comprising a population of cells and a plurality of channels adjacent the population of cells, where the channels extend from a first surface to a second surface of the planar scaffold; a first semipermeable ultrafiltration membrane disposed on the first surface and a second semipermeable ultrafiltration membrane disposed on the second surface of the planar scaffold; a first compartment comprising a first inlet and a first outlet, wherein the first compartment is adjacent to the first surface of the planar scaffold; a second compartment comprising a second inlet and a second outlet, wherein the second compartment is adjacent to the second surface of the planar scaffold, wherein the first inlet is configured for connection to an artery of a subject and the first outlet is connected to the second inlet of the second compartment, where the second outlet of the second compartment is configured for connection to a vein of the subject, where the semipermeable ultrafiltration membranes comprise a plurality of pores having a width in the range of 5 nm-5 micron, where the semipermeable ultrafiltration membrane allows transport of ultrafiltrate filtered from the arterial blood in the first compartment to the scaffold and transport of the ultrafiltrate from the plurality of channels in the scaffold into the second compartment. In certain cases, the first outlet may include a means for reducing the rate of flow of blood to the second compartment. In some case, the means may include a pressure reduction manifold. In some cases, the means for reducing the rate of flow of blood to the second compartment may include a pressure reduction channel. In some cases, the rate of flow of blood through the second compartment may be controlled by directing the blood through a channel having a reduced width compared to the width of the first compartment. In some case, the rate of flow of blood through the second compartment may be controlled by sizing the second compartment to have a reduced width compared to the width of the first compartment.

In some cases, the first compartment into which the blood is introduced into the device may have a dimension suitable for facilitating ultrafiltration of the blood. For example, the first compartment may have a height of 100 micron-6 mm, e.g., 500 micron-4 mm, 1 mm-3 mm, or 2 mm-3 mm.

In certain embodiments, the bioartificial device is dimensioned to fit in a body cavity of a subject. The device may be rectangular or cylindrical in shape. In certain case, the device may have a surface area of 50 cm$^2$ or less, such as 10-30 cm$^2$, 10-25 cm$^2$, 15-25 cm$^2$, 20-25 cm$^2$, 15-30 cm$^2$. In certain cases, the device may be rectangular and have a length of 3 cm-10 cm, a width of 1 cm-6 cm, and a height of 0.3 cm-2 cm, such as dimension (length×width×height) of 3 cm×1 cm×0.5 cm to 6 cm×4 cm×1 cm, e.g., 3 cm×1 cm×0.5 cm, 5 cm×2 cm×1 cm, or 6 cm×4 cm×1 cm.

As noted herein, the devices disclosed herein may maintain the transplanted cells in a functional and viable state for at least 1 month and up to a period of at least 2 months, 3 months, 4 months, 5 months, 6 months, 7 months, 8 months, 9 months, 10 months, 11 months, 1 year, 3 years, 5 years, 10 years, or up to 50 years, or longer, such as, 1 month-50 years, 1 year-25 years, 5 years-50 years, 5 years-25 years, 10 years-50 years, or 15 years-25 years.

In certain embodiments, the devices disclosed herein may be enclosed in a housing made from an inert material that does not degrade or foul when placed in a subject. Any material approved for medical devices placed in a subject may be utilized including but not limited to medical grade plastic, inert metals, such as, titanium, stainless steel, etc.

In certain embodiments, the bioartificial device comprises more than one semipermeable ultrafiltration membrane. In certain embodiments, the semipermeable ultrafiltration membrane is disposed on the first surface and the second surface of the planar scaffold. The semipermeable ultrafiltration membrane disposed on a first surface of the scaffold may be the same as the semipermeable ultrafiltration membrane disposed on the second surface of the scaffold or may be different. For example, the semipermeable ultrafiltration membrane adjacent to a compartment containing arterial blood may have smaller pores than the semipermeable ultrafiltration membrane adjacent a compartment containing the ultrafiltrate flowing through the channels in the matrix. In some cases, the semipermeable ultrafiltration membrane adjacent to a compartment containing arterial blood may have larger pores than the semipermeable ultrafiltration membrane adjacent a compartment containing the ultrafiltrate flowing through the channels in the matrix. In certain embodiments, the semipermeable membrane allows for filtration of an ultrafiltrate from the compartment containing arterial blood which ultrafiltrate is transported into the plurality of channels in the scaffold. The plurality of channels are adjacent the cells which provides for efficient exchange of molecules in the ultrafiltrate in the channels with the molecules released by the cells. These molecules diffuse in a concentration dependent manner between the lumen of the channels and the matrix surrounding the cells. For example, molecules, such as oxygen, glucose, lipids, vitamins, and minerals diffuse from the lumen of the channels into the matrix to the cells and molecules secreted by the cells such as urea, carbon dioxide, insulin are transported into the lumen of the channels. It is understood that in some embodiments, the some diffusion and exchange of molecules in the ultrafiltrate may occur outside of the channels, such as, with the ultrafiltrate that does not enter the channels and permeates through the matrix.

In certain embodiments, the semipermeable ultrafiltration membrane comprises a plurality of pores having a width in the range of 5 nm-5 micron. In some embodiments, the present disclosure provides a membrane comprising fabricated pores of defined dimensions and structure, and density. In certain embodiments, one or more surface of the membrane may be treated to limit protein adsorption. Such a treatment may include treatments that alter or confer surface charge, surface free energy, or treatments that promote adhesion of specific cell types. In certain embodiments, at least one pore of the membrane comprises any combination of a surface treatment. Surface treatments function to effect restriction of size and electrostatic charge of solutes that may be passed through such pores. Examples of surface treatments can be found, for example, in U.S. Patent Application Publication No. 20090131858, which is hereby incorporated by reference in its entirety.

In certain embodiments, the semipermeable ultrafiltration membrane is configured for filtration of biological fluids. In certain embodiments, the membrane comprises a plurality of nanopores, where the shapes and sizes of the pores are controlled. In certain embodiments, the membrane comprises a plurality of pores. In certain embodiments, the plurality of pores may be micropores and have a width in the range of 0.1 µm-5 µm, e.g., 0.1 µm-3 µm, 0.1 µm-0.5 µm, 0.5 µm-1 µm, 1 µm-1.5 µm, 1.5 µm-2 µm, 0.1 µm-1 µm, 0.1 µm-0.8 µm, 0.2 µm-0.7 µm, 0.2 µm-0.6 µm, 0.2 µm-0.5 µm. In certain embodiments, the plurality of pores may be nanopores and may have a width of 1 nm-500 nm, e.g., 1 nm-90 nm, 2 nm-50 nm, 3 nm-40 nm, 4 nm-50 nm, 4 nm-40 nm, 5 nm-50 nm, 5 nm-20 nm, 4 nm-20 nm, 7 nm-100 nm, 12 nm-20 nm, or 5 nm-10 nm. In certain embodiments, the plurality of pores are slit shaped and have a width as listed herein and have a length in the range of 1 µm-10 µm, e.g., 2 µm-3 µm, 3 µm-4 µm, 4 µm-5 µm, 5 µm-6 µm, 6 µm-7 µm, 7 µm-8 µm, 8 µm-9 µm, or 9 µm-10 µm. In certain cases, the rectangular pores have a depth of 100-1000 nm, a width of 3 nm-50 nm and a length of 1 micron-5 micron, e.g., a width×length×depth of 5 nm-50 nm×1 micron-2 micron× 200 nm-500 nm.

In certain embodiments, the devices of the present disclosure include semipermeable ultrafiltration membranes having a dimension (length×width) of 6 mm×6 mm, 5 mm×5 mm, 7 mm×7 mm, 8 mm×8 mm, 9 mm×9 mm, 10 mm×10 mm, 10 cm×10 cm, e.g., 10 mm×10 mm to 10 cm×10 cm. In some embodiments, the semipermeable ultrafiltration membrane may be rectangular.

In certain embodiments, the semipermeable ultrafiltration membrane has a surface area in the range of 0.5-100 $cm^2$, e.g., 30-100 $cm^2$, 10-30 $cm^2$, 15-30 $cm^2$, 15-20 $cm^2$, 20-25 $cm^2$, 25-30 $cm^2$, 0.5-10 $cm^2$, 0.75-5 $cm^2$, 0.75-3 $cm^2$, or 0.75-2 $cm^2$.

In certain embodiments, the devices disclosed herein may be substantially planar and may be dimensioned to have a surface area ranging from 20-100 $cm^2$ (on each planar side) and a thickness of 1 cm-3 cm. In certain embodiments, the devices disclosed herein may have a volume of up to 500 $cm^3$, such as, 50-500 $cm^3$, 100-500 $cm^3$, 100-300 $cm^3$, 100-150 $cm^3$. In certain cases, the device may include a semipermeable membrane having a surface of 5-75 $cm^2$, e.g., 5-50 $cm^2$, 10-30 $cm^2$, or 15-30 $cm^2$. The size of pores in the membrane may be 10 nm-100 nm in width, such as, 10 nm-20 nm.

The semipermeable ultrafiltration membranes of the present disclosure include any membrane material suitable for use in filtering biological fluids, wherein the membranes are structurally capable of supporting formation of pores. Examples of suitable membrane materials are known in the art and are described herein.

In certain embodiments, the membrane material is synthetic, biological, and/or biocompatible (e.g., for use outside or inside the body). Materials include, but are not limited to, silicon, which is biocompatible, coated silicon materials, polysilicon, silicon carbide, ultrananocrystalline diamond, diamond-like carbond (DLC), silicon dioxide, PMMA, SU-8, and PTFE. Other possible materials include metals (for example, titanium), ceramics (for example, silica or silicon nitride), and polymers (such as polytetrafluoroethylene, polymethylmethacrylate, polystyrenes and silicones). Materials for membranes can be found in, for example U.S. Patent Application Publication No. 20090131858, which is hereby incorporated by reference in its entirety.

A semipermeable ultrafiltration membrane of the present disclosure comprises a plurality of pores, where pore shapes include linear, square, rectangular (slit-shaped), circular, ovoid, elliptical, or other shapes. As used herein, width of a pore refers to the diameter where the pore is circular, ovoid or elliptical. In certain embodiments, the membrane comprises pores comprising a single shape or any combination of shapes. In certain embodiments, the sizes of pores are highly uniform. In certain embodiments, the pores are micromachined such that there is less than 20% size variability, less than 10% size variability, or less than 5% size variability between the dimensions of the slit-shaped pores. In certain embodiments, factors that determine appropriate pore size and shape include a balance between hydraulic permeability and solute permselectivity. In certain embodiments, the plurality of pores are slit-shaped pores which provide for optimum flux efficiency enabling efficient transport of molecules across the membrane. In certain embodiments, the membrane comprises slit-shaped nanopores. In certain embodiments, the semipermeable ultrafiltration membrane has approximately $10^3$-$10^8$ rectangular slit-shaped nanopores (e.g., $10^4$-$10^8$, or $10^5$-$10^7$) for example on a membrane surface area of 1 $cm^2$, 0.5 $cm^2$, or 0.4 $cm^2$. In certain embodiments, the number of slit-shaped nanopores on the semipermeable ultrafiltration membrane is sufficient to allow the membrane to generate physiologically sufficient ultrafiltration volume at capillary perfusion pressure. In certain embodiments, the porosity of the semipermeable ultrafiltration membrane is approximately 1%-50%, e.g., 10%-50%, 20%-50%, or 20%-75%, etc.).

In certain embodiments, the present disclosure provides a series of membranes comprising sparse arrays of monodisperse slit-shaped pores, manufactured, for example, using silicon bulk and surface micromachining techniques (see e.g., Fissell W H, et al., J Am Soc Nephrol 2002; 13:602 A; incorporated herein by reference in its entirety). In certain embodiments, the semipermeable ultrafiltration membrane is prototyped using microelectromechanical systems (MEMS) technology. In certain embodiments, the process uses the growth of a thin $SiO_2$ (oxide) layer on 400 μm-thick double side polished (DSP) silicon wafers followed by a low pressure chemical vapor deposition (LPCVD) of polysilicon (~500 nm). In certain embodiments the wafers are then specifically patterned, dry oxidized, wet etched, deposited with a second polysilicon layer, and finally blanket-etched until 400 nm of polysilicon remains and the underlying vertical oxide layer is exposed. In certain embodiments, the vertical sacrificial oxide layer defines the critical nanoscale pore size of the membranes. In certain embodiments, the low temperature oxide (LTO) (~1 μm) is deposited onto polysilicon of the wafers to serve as the hard mask for membrane protection. In certain embodiments, deep reactive ion etching (DRIE) removes the backside of each window until membranes were disclosed. In certain embodiments, the sacrificial oxide is etched away in 49% hydrofluoric acid (HF) during the final step of the fabrication process to leave behind open nanoscale slit pores. In certain embodiments, the wafers are subsequently cut into 1 cm×1 cm chips with an effective area of 6 $mm^2$×6 $mm^2$ containing 1500 windows each, with a total of $10^6$ pores per membrane. In certain embodiments, each rectangular pore is 7 nm in width, 300 nm in depth, and 2 μm in length. In certain embodiments, silicon micropore membrane (SμM) is fabricated to produce wafer-scale arrays of 500 nm deep by 4 μm long rectangular slit pores with 1000 nm-wide slit width using similar process. In certain embodiments, the wafers are diced to form 1 cm×1 cm chips with an effective area of 6×6 $mm^2$ containing 1500 windows each, with a total of 3.12×$10^6$ pores per membrane. In certain embodiments, all membranes may be cleaned using a conventional "piranha" clean procedure, which involve a 20 min-immersion in 3:1 sulfuric acid ($H_2SO_4$)/hydrogen peroxide ($H_2O_2$) mixture, followed by thorough rinses in deionized (DI) water.

In certain embodiments, the semipermeable ultrafiltration membrane is modified with PEG. Techniques for modification with PEG is well-known in the art, for example, in Papra et al. 2001 (Papra, A, et al., Langmuir 2001, 17 (5), 1457-1460.) In certain embodiments, the semipermeable ultrafiltration membrane is covalently modified with PEG. In certain embodiments, the surface modification with PEG prevents or minimizes protein fouling on the membrane surface. In certain embodiments, the technique used for PEG attachment involves a single reaction step which covalently couples silicon surface silanol group (Si—OH) to a chain of PEG polymer through a trimethoxysilane group forming a Si—O—Si-PEG sequence. In such embodiments, semipermeable ultrafiltration membranes were immersed in a solution of 3 mM 2-[methoxy(polyethyleneoxy)propyl] trimethoxysilane (PEG-silane) (Gelest: SIM6492.7) in toluene for 2 hrs at 70° C. In certain embodiments, a series of extensive washing steps involving toluene, ethanol, and DI water were used to rinse away unbounded PEG residue.

In certain embodiments, the compartments of the disclosed devices are of any appropriate shape and configuration to be compatible with the semipermeable ultrafiltration membranes and scaffold(s) included in the devices.

Figure 21:
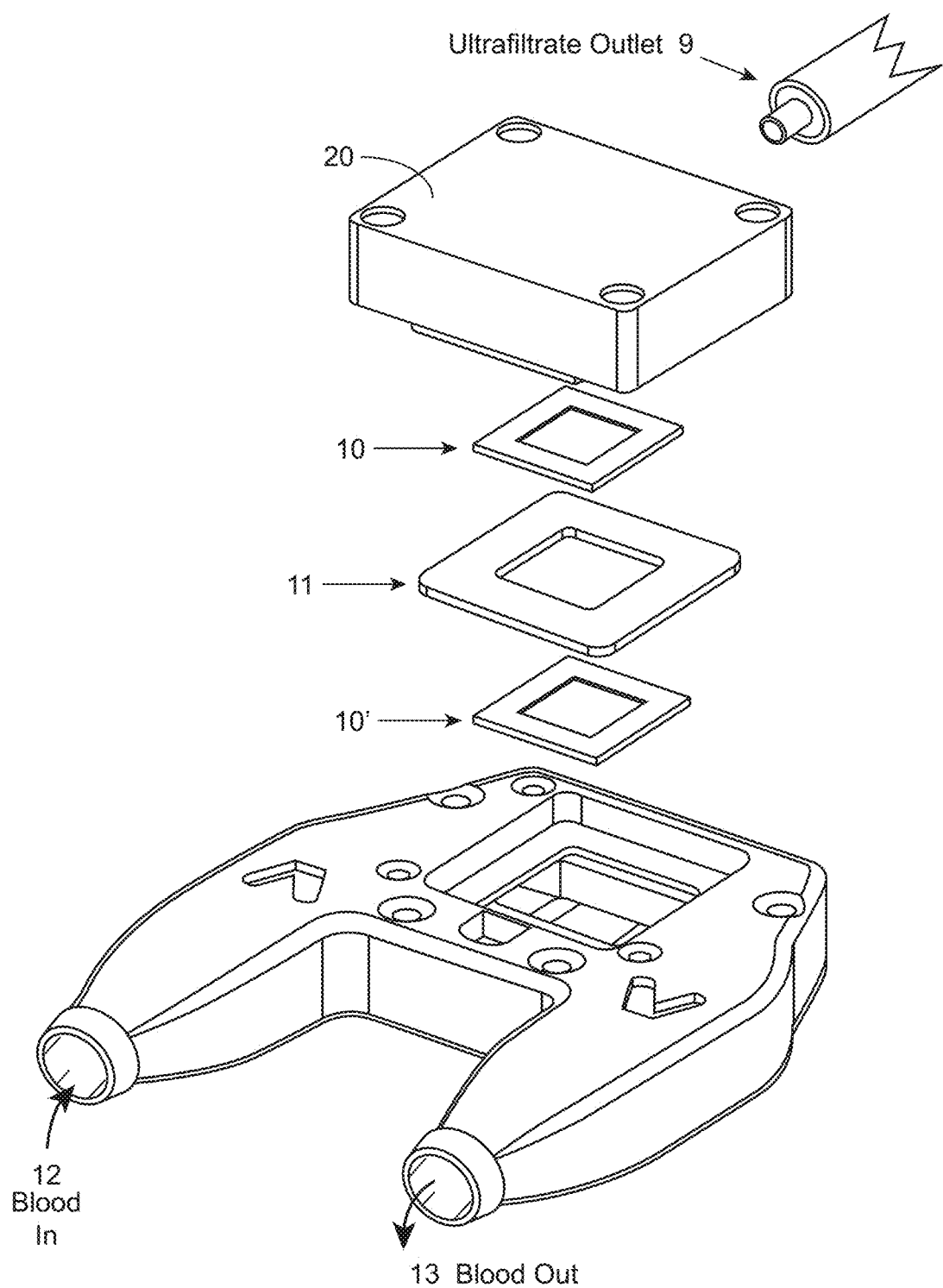
FIG. 21 shows a zoomed-in view of the components of the bioartificial device.
Figure 22A:
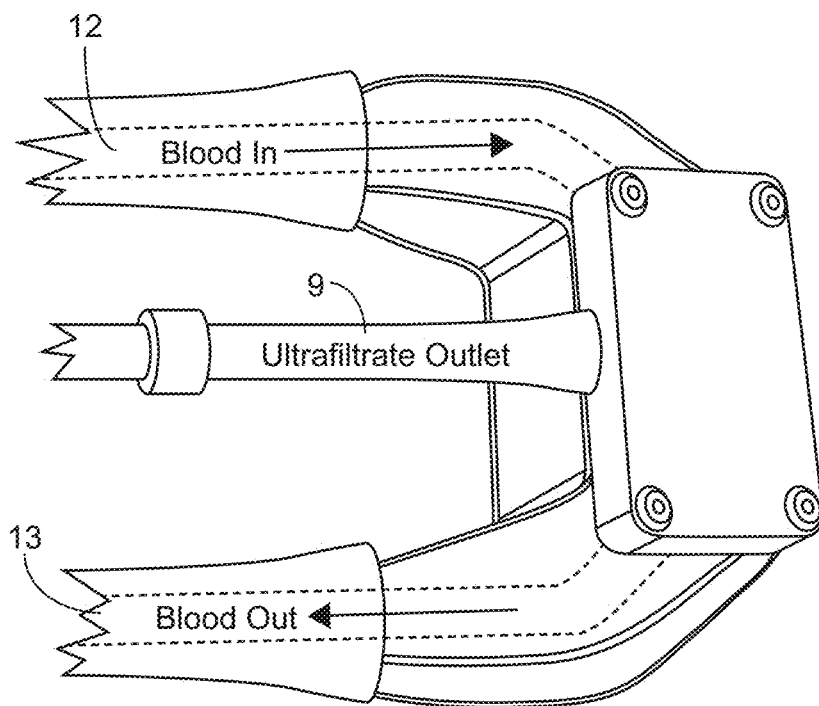
FIGS. 22A-22B show the inlet and outlet components of the bioartificial device.
Figure 22B:
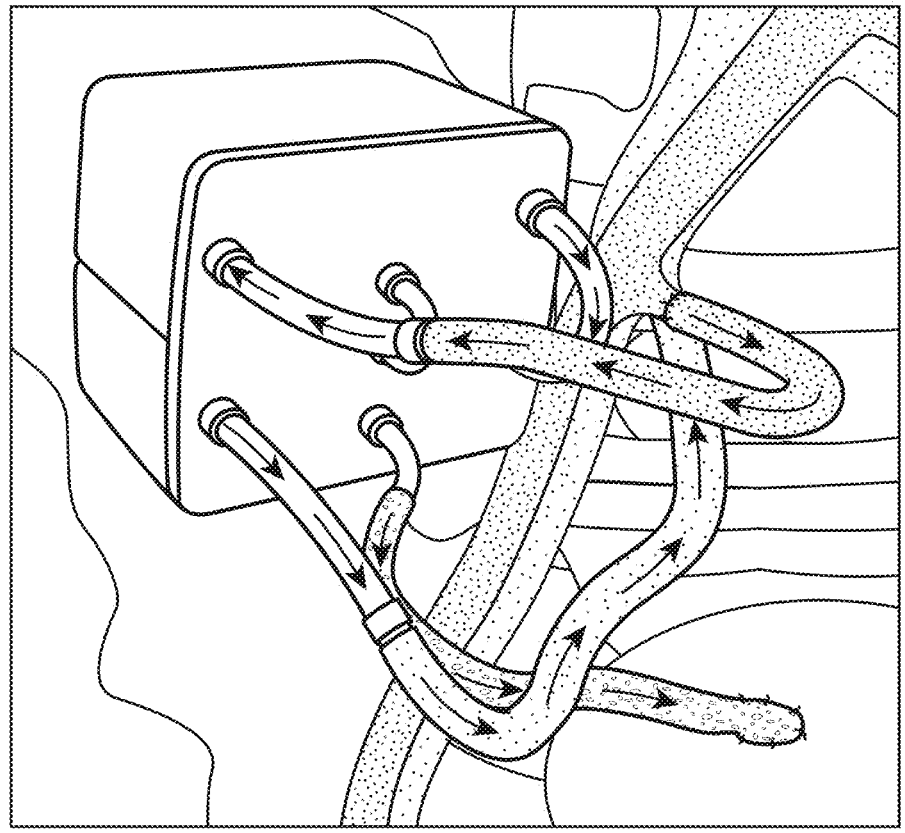

In certain embodiments, a device of the present disclosure may be as depicted in FIGS. 21 and 22A-22B. The device depicted in FIG. 21 includes a first compartment with an inlet that is connected to a tubing 12 for connection to an artery and an outlet connected to a tubing 13 for connection to a vein or an artery of a subject. The first compartment is shaped substantially as a cube or a cuboid and is closed on all sides other than an opening of the inlet, an opening of the outlet and an opening on a first side. This open first side is closed using a semipermeable membrane 10' as described herein. The semipermeable membrane allows for limited fluid connection between the first compartment and the scaffold 11. The first compartment is enclosed on all other sides with an impermeable biocompatible material. The semipermeable membrane 10' may be disposed on the open first side of the first compartment using a flexible compressible material such as a rubber support or a gasket. The scaffold with the plurality of channels and a population of cells may be disposed on the semipermeable membrane 10'. A second semipermeable membrane 10 may be supported by a frame of a flexible compressible material and may be disposed on the scaffold 11. A second compartment that is shaped substantially as a cube or a cuboid and is closed on all sides other than an outlet (for connection to a vein or body cavity of the subject or an analyte detection device, e.g., for measuring concentration of glucose and/or insulin in the ultrafiltrate) and a first open surface that is adjacent the semipermeable membrane 10. FIG. 22A depicts an assembled device which includes tubing 12 that is configured for connection to an artery and tubing 13 that is configured for connection to an artery or a vein of a subject and an ultrafiltrate outlet for connection to a second vein or a body cavity of the subject or to an analyte analysis device. As explained herein, the first compartment is in fluid communication with the first surface of the planar scaffold 11. In certain embodiments, the second compartment 20 is in fluid communication with the second surface of the planar scaffold 11. In certain embodiments, the first compartment is in fluid communication with the first surface of the planar scaffold 11 only by means of the pores within the membrane 10'. In certain embodiments, the second compartment is in fluid communication with the second surface of the planar scaffold 11 only by means of the pores within the membrane 10. In certain cases, the second semipermeable membrane 10 may include pores that are larger in size than the pores in the first semipermeable membrane 10'. In certain cases, the second semipermeable membrane 10 may include pores that are smaller in size than the pores in the first semipermeable membrane 10'. In certain cases, the device may not include the second semipermeable membrane 10. In these embodiments, the ultrafiltrate may flow from the plurality of channels in the scaffold to the second compartment.

In certain embodiments, the device may include two scaffolds to provide an increased amount of ultrafiltrate. For example, such a device may be configured as depicted in FIGS. 23A and 23B and 36A-36B. The device 25 includes a tubing 12 configured for supplying blood to first compartment 26 via an inlet in the first compartment. The tubing may be connected to an artery. The device may include a tubing 13 for returning the blood to the subject and may be connected to an outlet of the first compartment 26 and to an artery or a vein of the subject. The device 25 also includes a tubing 9 for transporting ultrafiltrate from an ultrafiltrate outlet connected to ultrafiltrate chambers 30a and 30b. FIG. 23B shows a perpendicular cross section of the device of FIG. 23A. FIG. 23B depicts the blood channel (first compartment 26) that includes an inlet for entry of arterial blood and an outlet for exit of the blood into back to the subject. The first compartment 26 is sandwiched between two scaffolds 11a and 11b across which ultrafiltrate moves into the ultrafiltrate chambers (second compartment 30a and third compartment 30b). Also depicted is a first membrane (10a) adjacent the first compartment 26 and a second membrane (10b) adjacent the ultrafiltrate compartments (second compartment 30a and third compartment 30b). The ultrafiltrate compartments (second compartment 30a and third compartment 30b) are connected to channels 31a and 31b which merge into a single channel 33 and is configured for connection to conduit 9 for connecting to a vein of the subject. As noted herein, in some embodiments, the device may not include the second membranes 10b. In some embodiments, the second membrane 10b may have pores that are larger in width than the pores in the first membrane 10a. In some embodiments, the second membrane 10b may have pores that are smaller in width than the pores in the first membrane 10a.

Figure 6:
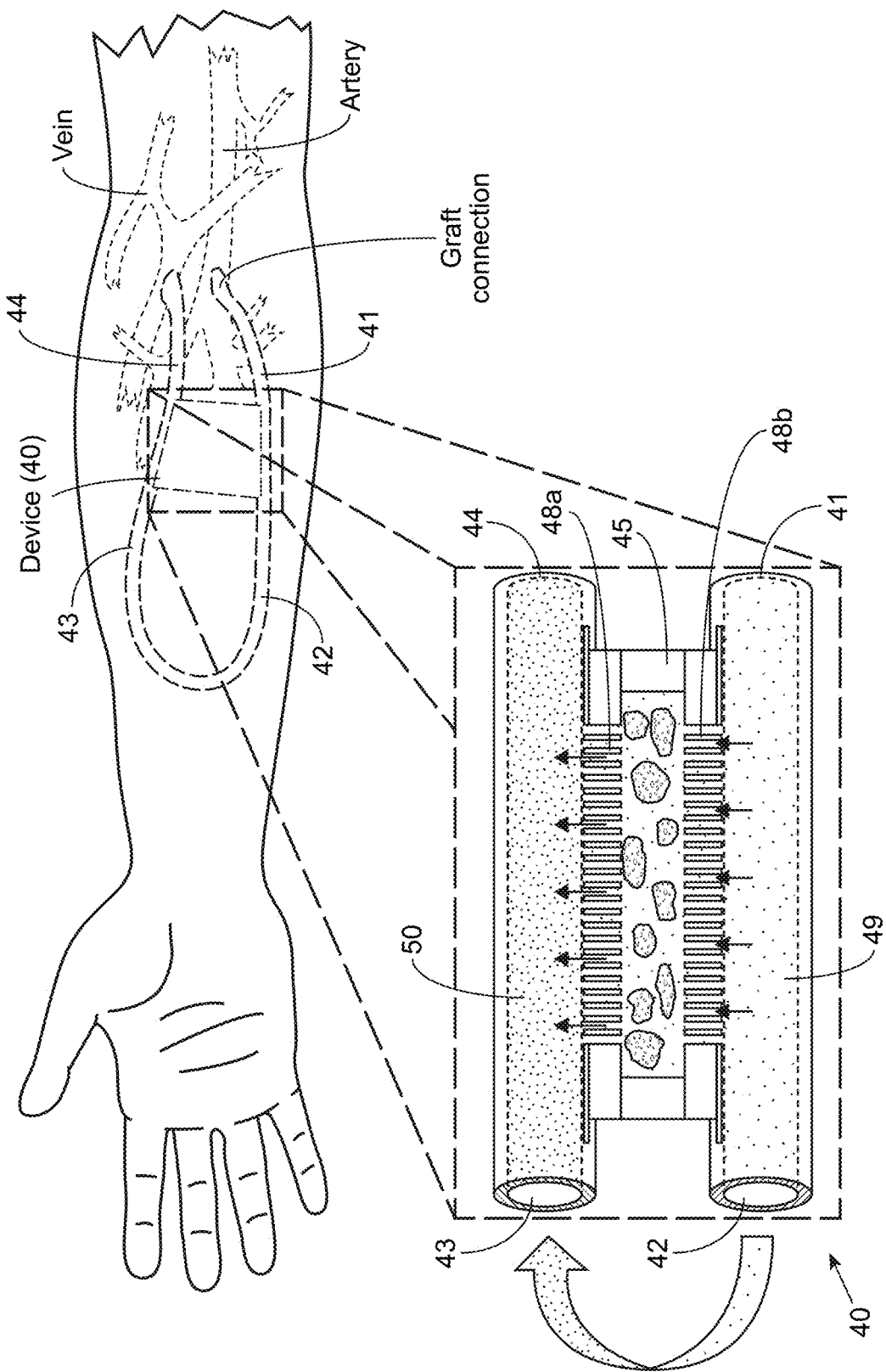
FIG. 6 shows a conceptual illustration of the implantable intravascular bioartificial pancreas device in the arm of a T1D patient.

Another exemplary device is depicted in FIG. 6. The device 40 includes a first compartment 49 with an inlet 41 for connection to an artery of a subject and an outlet 42 connected to a second compartment 50 via its inlet 43. The second compartment 50 includes an outlet 44 for returning the blood to a vein of the subject. In this embodiment, the ultrafiltrate returns to the subject via the second compartment 50 after traversing through the second membrane 48a. The ultrafiltrate is produced by filtration of arterial blood across the first membrane 48b. The ultrafiltrate carries metabolites exchanged with the cells in the scaffold 45 into the second compartment 50. As noted herein, in some embodiments, the device may not include the second membrane 48a. In some embodiments, the second membrane 48a may have pores that are larger in width than the pores in the first membrane 48a.

Figure 20A:
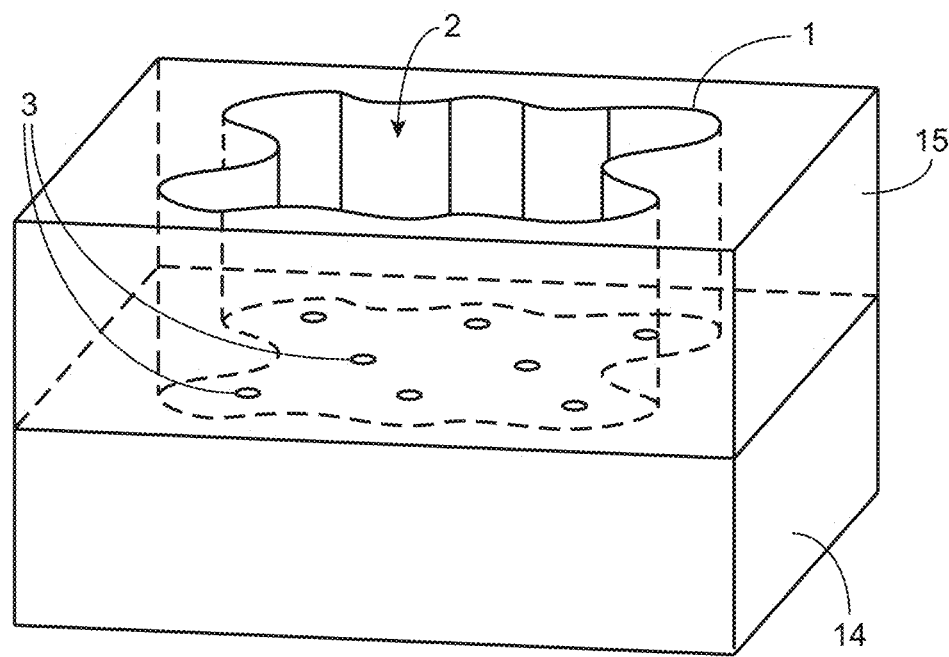
FIGS. 20A-20D show an illustration of the process and fixtures for Cell Scaffold/islet chamber (IC) construction. The terms cell scaffold and islet chamber are used interchangeably.
Figure 20B:
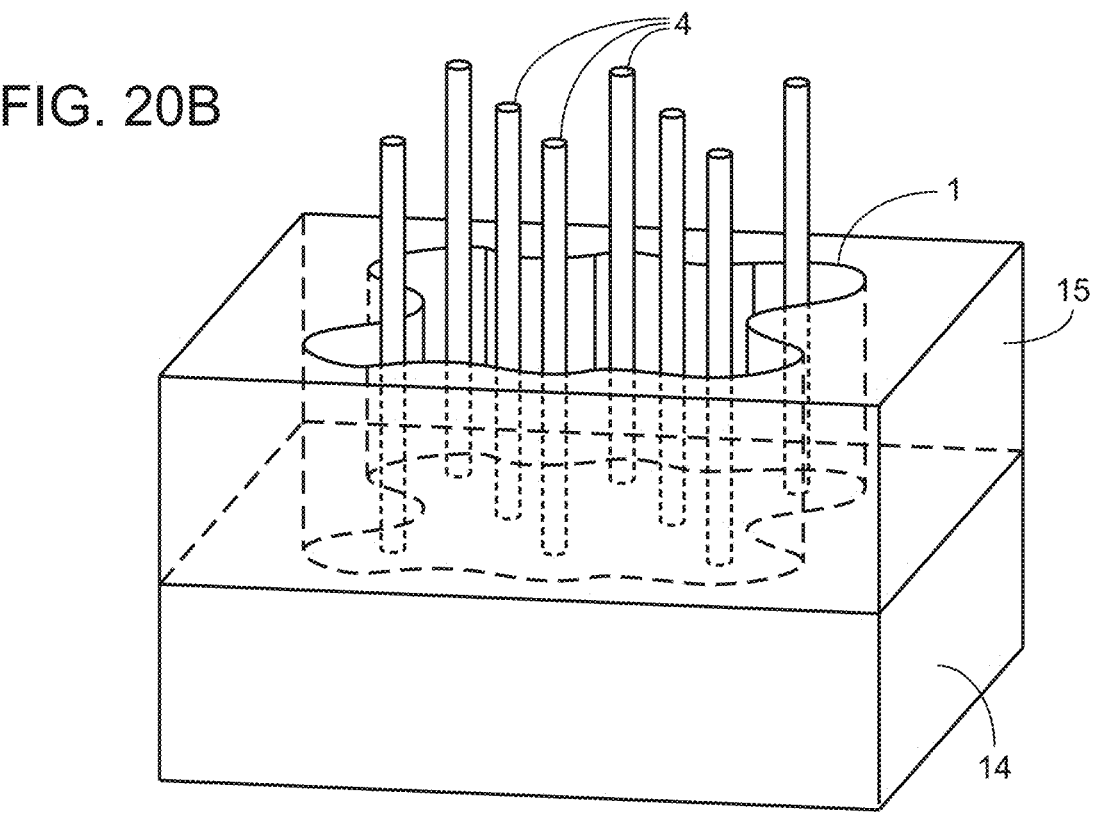
Figure 20C:
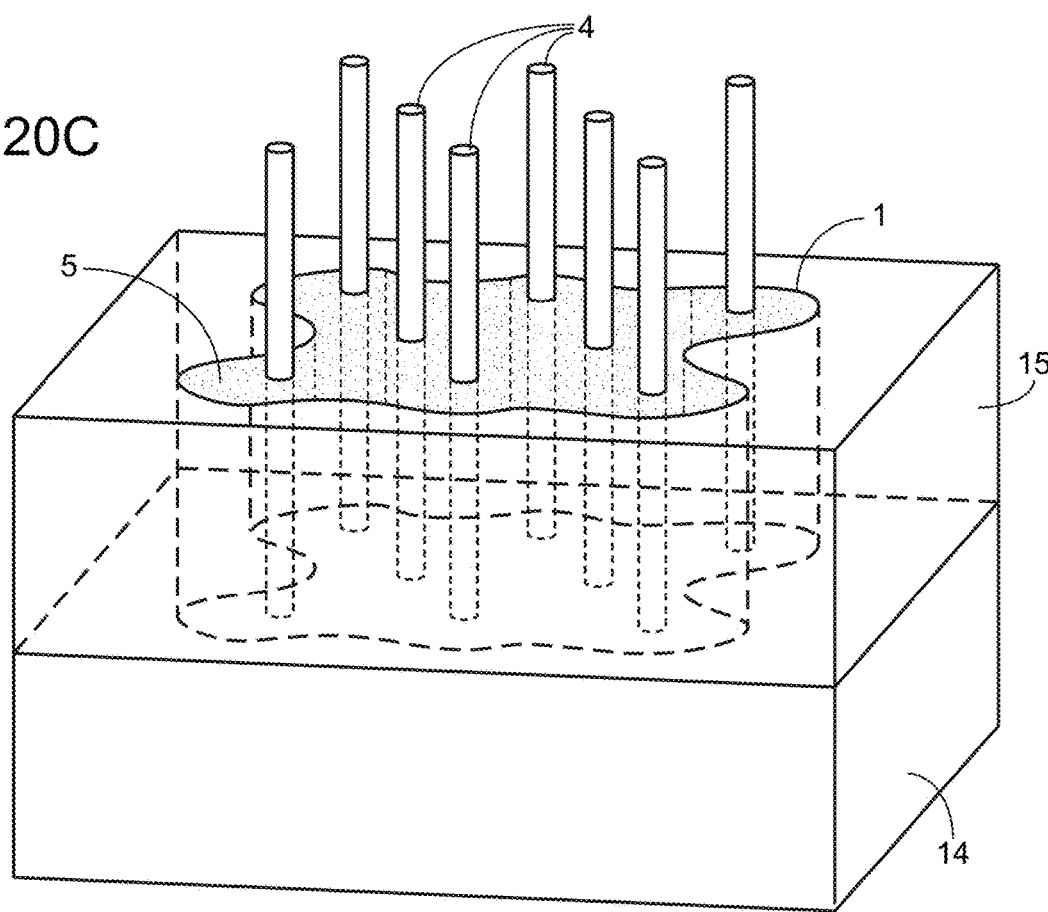
Figure 20D:
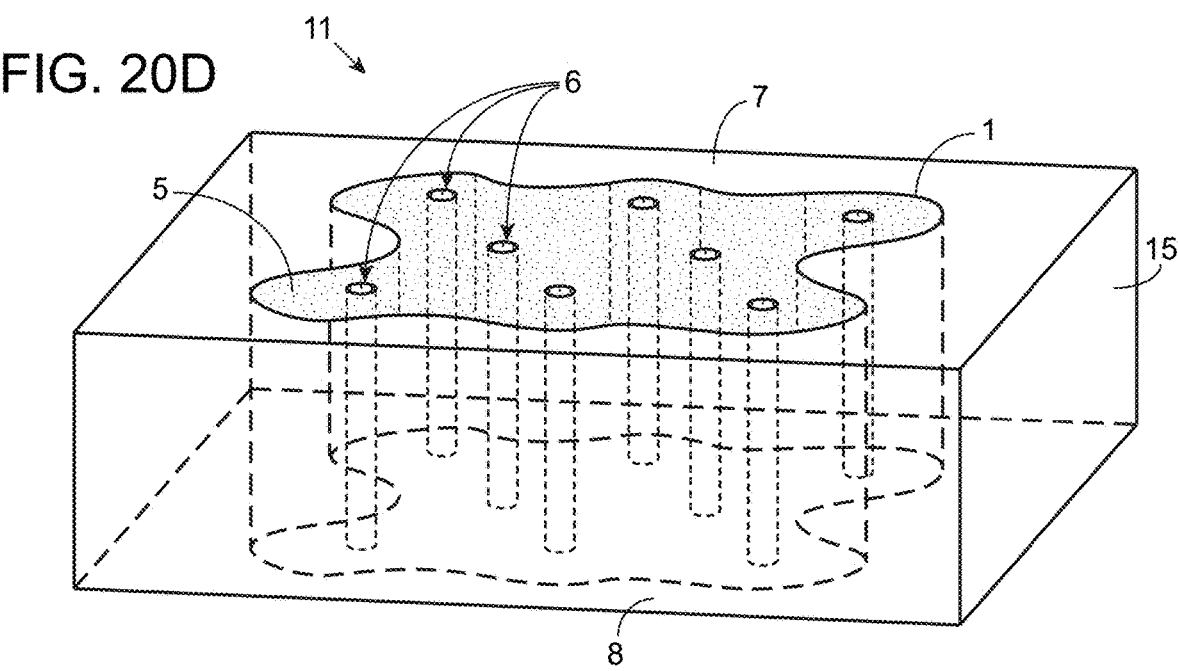

In certain aspects, the scaffold may also be referred to as an islet chamber (IC) or a cell scaffold and may be formed as depicted in FIGS. 20A-20D. FIG. 20A depicts a substantially planar solid substrate 15 disposed on a supporting substrate 14. The solid substrate 15 includes a void 2 that has been formed by removal of a portion of the solid substrate 15. The supporting substrate includes a plurality of holes or indents (3) to hold elongate posts (e.g., wires or tubes) in a substantially straight orientation (perpendicular to the first and second surfaces of the solid substrate 15). FIG. 20B depicts wires 4 inserted into the holes 3 of the supporting layer 15. The periphery of the void is marked by the border 1. FIG. 20C illustrates the void filled with a matrix 5 that is polymerized and/or solidified (e.g., at a lower temperature). As discussed in the foregoing sections, the matrix also includes a population of cells. After the matrix is set (e.g., via polymerization), the wires 4 are removed to reveal a plurality of channels 6 which extend from a first surface 7 to a second surface 8 of the scaffold 11 (FIG. 20D). In certain aspects, the plurality of channels may have a rectangular periphery, such as depicted in FIGS. 47A-47C. FIGS. 47A-47C show a schematic of a region of the scaffold of the present disclosure which includes a plurality of rectangular shaped channels adjacent a population of cells.

Figure 55:
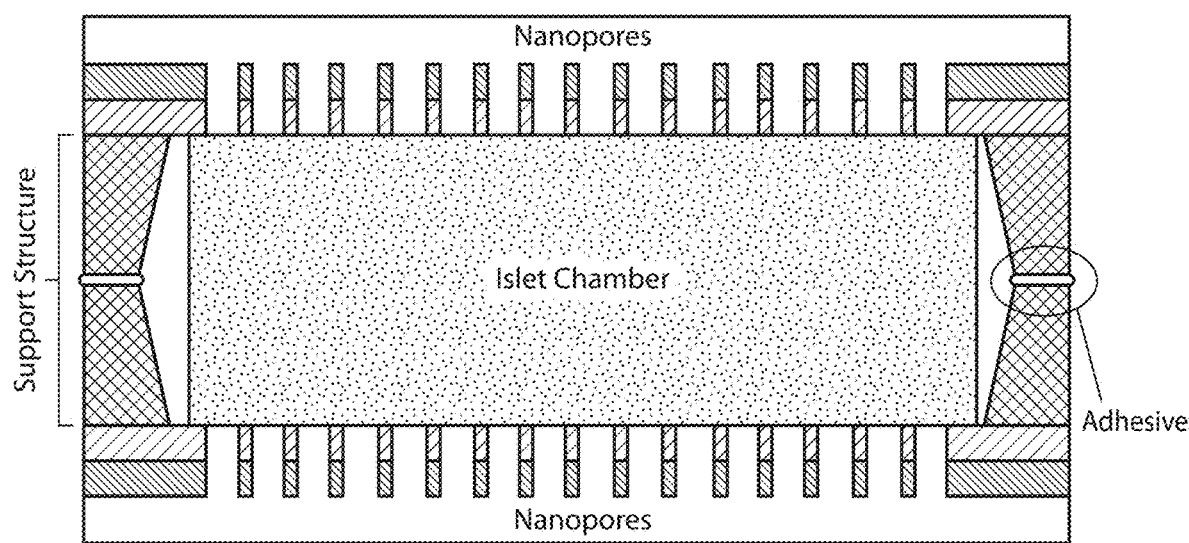
FIG. 55 shows a cross-sectional view of SNM and Islet Chamber.

FIGS. 55A and 55B show a schematic of a connector for connecting a graft to a device as disclosed. The capsule-graft connector will affix the bioartificial device to vascular grafts and provide a blood flow path between the device and the vascular grafts on both the arterial and venous ends. FIG. 55A illustrates a device-graft connector design and FIG. 55B is a cross-sectional depiction of this design. Part 1 affixes the connector to the device's blood port (inlet). Part 2 provides the blood flow path from the vascular graft to the device and may possess a tapered lumen that gradually transitions blood from the larger diameter vascular graft to the smaller diameter blood port (inlet, not shown) of the device. Part 3 affixes the vascular graft (Part 4) to Part 2 by compressing the vascular graft to Part 2. Part 4 (vascular graft) provides the blood path between the device-graft connector and either the arterial or venous vessel anastomosis site (not shown).

In certain embodiments, the devices provided herein provide formation of ultrafiltrate by convection rather than predominantly by diffusion thereby increasing the efficiency of ultrafiltrate formation and/or flow of the ultrafiltrate back to the subject.

Methods

The bioartificial devices of the present disclosure may be used for transporting nutrients to a planar scaffold comprising the population of cells in the device and release ultrafiltrate fluid containing molecules secreted by the cells to a subject. In certain embodiments, the cells are progenitor cells. In certain embodiments, the cells are pancreatic cells, such as, insulin producing cells isolated from pancreatic islets or derived by differentiation of stem cells (e.g., induced pluripotent stem cells). In certain embodiments, the cells excrete insulin. In certain embodiments, the cells release insulin into the ultrafiltrate fluid.

In certain embodiments, the bioartificial device of the present disclosure having semipermeable ultrafiltration membranes with pores are used for protecting cells encapsulated in the scaffolds described herein from an attack by the immune system of the subject. In certain embodiments, the bioartificial device of the present disclosure can reduce passage of immune system components such as cells, immune factors, such as, antibodies and cytokines. In certain embodiments, the bioartificial device of the present disclosure can reduce passage of immune factors. In certain embodiments, the bioartificial device of the present disclosure can reduce passage of cytokines. In certain embodiments, the bioartificial device of the present disclosure can reduce passage of TNF-α, IFN-γ, and/or IL-1β while permitting transport of nutrients from the blood of the subject to the cells in the device. In certain embodiments, the bioartificial device of the present disclosure can reduce passage of components of the immune system (e.g., immune cells, antibodies, cytokines, such as, TNF-α, IFN-γ, and/or IL-1β) by at least 50% (e.g., 60%-80%). In certain embodiments, the bioartificial device of the present disclosure having semipermeable ultrafiltration membranes with nanopores (e.g. slit-shaped nanopore membranes with a PEG surface coating) are used for exchange of nutrients and small molecules to the population of cells. In certain embodiments, the bioartificial device may limit the diffusion of cytokines and immunoglobulins through the semipermeable ultrafiltration membrane.

In certain embodiments, the bioartificial device of the present disclosure comprising a population of pancreatic islet cells in the matrix increase pancreatic islet cell viability within the matrix.

The bioartificial device of the present disclosure are sized to house an effective number for cells within the bioartificial device for treatment of a subject in need thereof. For example, the subject may be suffering from a condition caused by lack of functional cells, e.g., wherein molecules typically secreted by functional cells are not secreted or are secreted at a level resulting in the condition. Providing functional cells within the bioartificial device of the present disclosure could alleviate the condition. Exemplary conditions include type 1 diabetes, Parkinson's disease, muscular dystrophy and the like.

The device may be transplanted into any suitable location in the body, such as, subcutaneously, intraperitoneally, or in the brain, spinal cord, pancreas, liver, uterus, skin, bladder, kidney, muscle and the like. The site of implantation may be selected based on the diseased/injured tissue that requires treatment. For treatment of a disease such as diabetes mellitus (DM), the device may be placed in a clinically convenient site such as the subcutaneous space or the omentum. The device may be connected to the vascular system of the subject as described herein. In some case, the device may be connected inline to a vascular graft. In some cases, the device may be connected to the subject to supply the ultrafiltrate to an artery, a vein, a body cavity (e.g., peritoneal cavity), or a combination thereof, of the subject. In some cases, the device may be connected to a catheter to supply the ultrafiltrate to a vein to which the catheter is connected.

In certain cases, the device may be connected to an artery of the subject and may supply the ultrafiltrate back to the same artery (e.g., at a connection downstream to the site at which the artery was connected to the device). In certain cases, the device may be connected to an artery of the subject and may supply the ultrafiltrate to a vein of the subject. In certain cases, the device may be connected to an artery of the subject and may supply the ultrafiltrate to a body cavity of the subject. In some embodiments, the device may include a sampling port for sampling the ultrafiltrate, for example, using an analyte analysis device for measuring concentration of insulin and/or glucose in the ultrafiltrate.

In certain embodiments, the bioartificial device disclosed herein may be used to treat a person having diabetes, such as, type 1 diabetes. The device may include pancreatic islet cells or may include stem cells that are capable of differentiating into pancreatic islet cells. In certain embodiments, pluripotent stem cells (PSCs) may be differentiated into pancreatic islet cells inside the device. In some case, the device may include PSCs and the device may be implanted adjacent the pancreas or liver of the subject.

As noted herein, the devices disclosed herein may maintain the transplanted cells in a functional and viable state for at least 1 month and up to a period of at least 2 months, 3 months, 4 months, 5 months, 6 months, 7 months, 8 months, 9 months, 10 months, 11 months, or up to a year or longer. In some embodiments, the present device provide immunoisolation while supporting supply of essential components to enable islets, beta cells, and other insulin producing cells to remain viable and functional for treatment of diabetes.

The methods and devices disclosed herein can be used for both human clinical and veterinary applications. Thus, the subject or patient to whom the bioartificial device is administered can be a human or, in the case of veterinary applications, can be a laboratory, agricultural, domestic, or wild animal. The subject devices and methods can be applied to animals including, but not limited to, humans, laboratory animals such as monkeys and chimpanzees, domestic animals such as dogs and cats, agricultural animals such as cows, horses, pigs, sheep, goats, and wild animals in captivity such as bears, pandas, lions, tigers, leopards, elephants, zebras, giraffes, gorillas, dolphins, and whales.

In operation, blood is directed from a patient's vasculature (i.e. artery) into the inlet of the first compartment of the bioartificial device. Blood flows through the first compartment of the bioartificial device, and nutrients and small molecules from the blood are passed through the semipermeable ultrafiltration membrane, while large molecules, such as immunoglobulins and cytokines within the blood are prevented from coming in contact with the cells in the device. Nutrients and small molecules include, but are not limited to glucose, oxygen, and insulin. The small molecules and nutrients that pass through the semipermeable ultrafiltration membrane are filtered to form an ultrafiltrate which contacts the matrix of the device comprising the population of cells. In certain embodiments, the population of cells release insulin into the ultrafiltrate. The ultrafiltrate then passes through the ultrafiltrate channels of the matrix, which then passes through a second semipermeable ultrafiltration membrane. Optionally, the outlet of the second compartment can be configured to connect to a catheter. In certain embodiments, the catheter connects to the second vein.

The disclosed devices provide a high rate of ultrafiltration creating ultrafiltrate at the rate of 1-15 ml/min at physiological rate of blood flow.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., room temperature (RT); base pairs (bp); kilobases (kb); picoliters (pl); seconds (s or sec); minutes (m or min); hours (h or hr); days (d); weeks (wk or wks); nanoliters (nl); microliters (ul); milliliters (ml); liters (L); nanograms (ng); micrograms (ug); milligrams (mg); grams ((g), in the context of mass); kilograms (kg); equivalents of the force of gravity ((g), in the context of centrifugation); nanomolar (nM); micromolar (uM), millimolar (mM); molar (M); amino acids (aa); kilobases (kb); base pairs (bp); nucleotides (nt); intramuscular (i.m.); intraperitoneal (i.p.); subcutaneous (s.c.); and the like.

Example 1

The development and characterization of a new generation of semipermeable ultrafiltration membrane, the silicon nanopore membrane (SNM), designed with approximately 7 nm-wide slit-pores to provide middle molecule selectivity by limiting passage of proinflammatory cytokines is shown. The use of convective transport with a pressure differential across the SNM overcomes the mass transfer limitations associated with diffusion through nanometer-scale pores. The SNM exhibited a hydraulic permeability of 130 ml/hr/$m^2$/mmHg Analysis of sieving coefficients revealed 80% reduction in cytokines passage through SNM under convective transport. SNM protected encapsulated islets from infiltrating cytokines and retained islet viability over 6 hours and remained responsive to changes in glucose levels unlike non-encapsulated controls. The concept involves using the pressure difference between the artery and vein to generate ultrafiltrate and drive transport of glucose, insulin, and other small molecules through the SNM to support function of encased islets while preventing passage of immune components. SNM design and fabrication, followed by characterization of its immunobarrier properties under cytokine challenge with convective transport, and assessment of SNM encapsulated islet viability and glucose-insulin response were developed. Specifically, hydraulic permeability measurement and solute selectivity for SNM were determined. Mouse islets were encapsulated between SNM in a closed mock-loop fluid circuit (FIG. 7) under simulated physiological pressure difference in the presence of a cocktail of pro-inflammatory cytokines including TNF-α, IL-1β, and IFN-γ. Islet viability and glucose stimulated insulin production were evaluated to demonstrate the potential of SNM as an encapsulation material for islet immunoisolation under convective transport. Together, these data demonstrate the novel membrane exhibiting unprecedented hydraulic permeability and immunoprotection for islet transplantation therapy.

1.1 Materials and Methods
Experimental Overview

Figure 8:
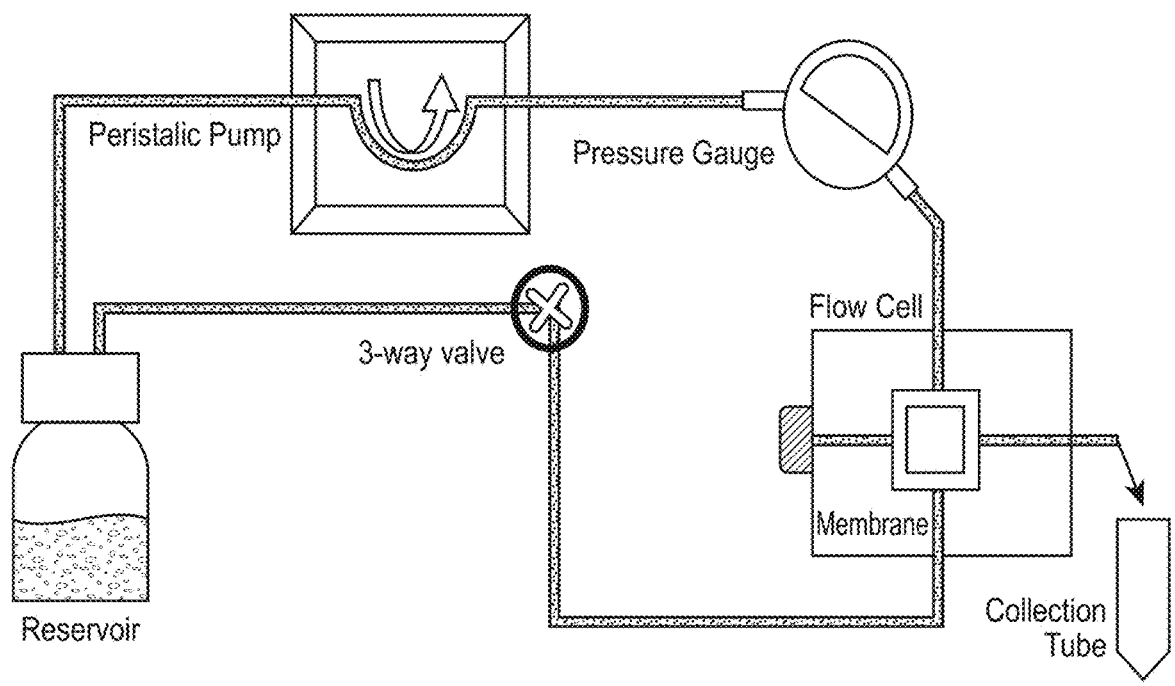
FIG. 8 shows a schematic diagram of the pressure-driven cytokine filtration testing system.

SNM were fabricated to produce an active membrane area (6×6 mm) consisting of ~$10^6$ rectangular slit pores with ~7 nm in width, 300 nm in depth, and 2 μm in length (FIG. 1). The surface of SNM was subsequently modified with polyethylene glycol (PEG) to minimize protein fouling. All SNM membranes in this study were tested with an average pore size of ~7 nm. The transport of small solutes was first analyzed including cytokines across a single SNM using a pressure-driven filtration assembly (FIG. 8). To mimic the proposed bioartificial pancreas device with convective ultrafiltration under physiological pressure, a construction of a benchtop mock-loop circuit consisting of a three-layer flow cell with two enclosed SNM (FIG. 9), where the top, middle, and bottom compartments recapitulated the "artery", "encapsulated islet chamber", and "vein", respectively. The percentage of cytokines, glucose, and insulin was subsequently characterized within the different locations of the mock-loop device. Finally, the viability and glucose-insulin response of the SNM-encapsulated mouse islets in the mock-loop circuit with circulating cytokines were tested.

1.2 Substrate Preparation
1.2.1 Silicon Nanopore Membranes (SNM) Architecture and Fabrication Silicon nanopore membranes (SNM) have been prototyped from silicon substrates by MEMS technology as previously reported with some modifications (FIG. 2A-I). Briefly, the process used the growth of a thin $SiO_2$ (oxide) layer on 400 μm-thick double side polished (DSP) silicon wafers followed by a low pressure chemical vapor deposition (LPCVD) of polysilicon (~500 nm). The wafers were then specifically patterned, dry oxidized, wet etched, deposited with a second polysilicon layer, and finally blanket etched until 400 nm of polysilicon remained and the underlying vertical oxide layer was exposed. The vertical sacrificial oxide layer defined the critical nanoscale pore size of the membranes. The low temperature oxide (LTO) (~1 μm) was deposited onto polysilicon of the wafers to serve as the hard mask for membrane protection. Deep reactive ion etching (DRIE) removed the backside of each window until membranes were disclosed. Eventually, the sacrificial oxide was etched away in 49% hydrofluoric acid (HF) during the final step of the fabrication process to leave behind open nanoscale slit pores. The wafers were subsequently cut into 1×1 cm chips with an effective area of 6×6 mm² containing 1500 windows each, with a total of $10^6$ pores per membrane. Each rectangular pore was 7 nm in width, 300 nm in depth, and 2 μm in length. All membranes were cleaned using a conventional "piranha" clean procedure, which involved a 20 min-immersion in 3:1 sulfuric acid ($H_2SO_4$)/hydrogen peroxide ($H_2O_2$) mixture, followed by thorough rinses in deionized (DI) water. Images of SNM were obtained using scanning electron microscope (SEM) (Leo 1550) (FIG. 1).

1.2.2 Surface Modification of SNM with Poly(ethylene glycol) (PEG)

SNM were covalently modified with PEG using a previously reported protocol with some modifications to prevent protein fouling on the membrane surface. The technique used for PEG attachment involved a single reaction step which covalently couples silicon surface silanol group (Si—OH) to a chain of PEG polymer through a trimethoxysilane group forming a Si—O—Si-PEG sequence. Briefly, SNM were immersed in a solution of 3 mM2[methoxy(polyethyleneoxy)propyl] trimethoxysilane (PEGsilane) (Gelest: SIM6492.7) in toluene for 2 hr at 70° C. A series of extensive washing steps involving toluene, ethanol, and DI water were used to rinse away unbounded PEG residue.

1.2.3 Hydraulic Permeability for SNM Pore Size Characterization

An automated mass and pressure measurement system was utilized for characterizing liquid flow through the SNM under a tangential-flow filtration operation. The pore size of the SNM can be related to filtration flow parameters using $$h = \sqrt[3]{\frac{12\mu l Q}{nw\Delta P}}, \qquad \text{(Equation 1)}$$

where h is pore width, H is the viscosity, l is the membrane thickness, Q is the volumetric flow rate, n is the number of pores per membrane, w is the pore length, and ΔP is the transmembrane pressure. To assemble the overall system for SNM pore size characterization (FIG. 9), air was applied through a syringe pump (Sigma: Z675709) into a water reservoir. Water was circulated by a peristaltic pump (Masterflex: 07551-00) through a differential pressure transducer (Omega: PX429 015GI), a flow cell with enclosed membrane, and returned to the original water reservoir. The flow cell was assembled with the SNM submerged under water to remove air bubbles from all compartments. Specifically, a membrane was positioned with the polysilicon interface facing down with a customized silicone gasket positioned on top of the membrane, followed by the final placement of a filtrate chamber on top of the gasket. All sections were fastened together and secured to the base with hand-tightened hex bolts until gasket was visibly compressed. The ultrafiltrate permeated through the membrane was routed to a liquid collection container that rested on a precision mass balance (Mettler Toledo: XS205). Measurements from the differential pressure transducer and the mass balance were automatically collected with a data acquisition laptop. A typical membrane hydraulic permeability test consisted of 5 ml/min flow rate and 4 pressure cycles (5, 1, 5, and 1 psi) for durations of 150 s each.

Using the specifications for pore length, membrane thickness, and total number of pores provided based on individual wafer designs, the average pore size of SNM was calculated using Equation 1. All SNM membranes in this study were surface-modified with PEG and exhibited an average pore size of ~7 nm.

1.3 Assessment of SNM Immunoisolation In Vitro
1.3.1 Membrane Sieving Coefficients Under Pressure-Driven Filtration Fluid was circulated by a peristaltic pump through a circuit that consisted of a differential pressure transducer, a polycarbonate flow cell with enclosed SNM, a three-way valve, and a fluid reservoir (FIG. 8). The flow cell consisted of two separate flow cell compartments sandwiching a single SNM and silicone gasket. The top filtrate chamber routed permeated ultrafiltrate to a liquid collection container, whereas the base chamber was connected to a three-way valve. A solution of 3% bovine serum albumin (BSA) (Sigma: A-7030) was used to flush the entire loop prior to the experiment. Solution consisting of mouse cytokines TNF-α (1000 U/ml) (Peprotech: 315-01A), IFN-γ (1000 U/ml) (Peprotech: 315-05), IL-1β (50 U/ml) (Peprotech: 211-11B) 37, glucose (400 mg/dL) (Sigma-Aldrich: G8270), and insulin (150 mU/L) (Novo Nordisk: 0169-1833-11) in a 3% BSA solution was then switched to the circuit at 5 ml/min with a physiological pressure difference ~2 psi 38. Ultrafiltrate that permeated through the SNM was collected at various time points for up to 6 hrs and analyzed with the enzyme-linked immunosorbent assays (ELISA) (BD Biosciences: 560478 & 558258; Thermo Pierce: EM2IL1B). The sieving coefficients of solutes across SNM were calculated using $$S = \frac{C_f}{C_b},$$ (Equation 2)

where S is the sieving coefficient, Cf is the concentration of the solute in the filtrate, and Cb is the molecule concentration in the bulk retentate solution.

1.3.2 Solute Distribution in the Mock-Loop Circuit

A mock-loop circuit assembly with three flow cell components without cells to mimic the architecture of the final bioartificial pancreas device. Briefly, two SNM with customized silicone gasket frames were sandwiched in between three flow cell components. The middle flow cell was the encapsulation chamber comprised of a cylindrical chamber separating the two membranes. A peristaltic pump drove the fluid through the top of the flow cell mimicking the "artery", then over the bottom of the flow cell resembling "vein", and finally back to the original reservoir. For convective experiments, a three-way valve was used to create flow resistance for a physiological pressure difference ~2 psi between the top and the bottom compartments of the flow cell. Ultrafiltration occurred in the middle encapsulation chamber at this pressure difference. To study the transport of cytokines through the three-layered bioartificial pancreas device, solution consisting of mouse cytokines TNF-α (1000 U/ml), IFN-γ (1000 U/ml), and IL-1β (50 U/ml), glucose (400 mg/dL), insulin (150 mU/L) in 3% BSA was circulated through the circuit at a flow rate of 5 ml/min. Silicon membranes with 1000 nm-wide slit pores (SμM) were used as the control. Solutions were collected and analyzed with ELISA at the end of 6-hr experiments for the top, middle, and bottom chambers.

1.3.3 Culture of Membrane-Encapsulated Islets in the Mock-Loop Circuit

Figure 7:
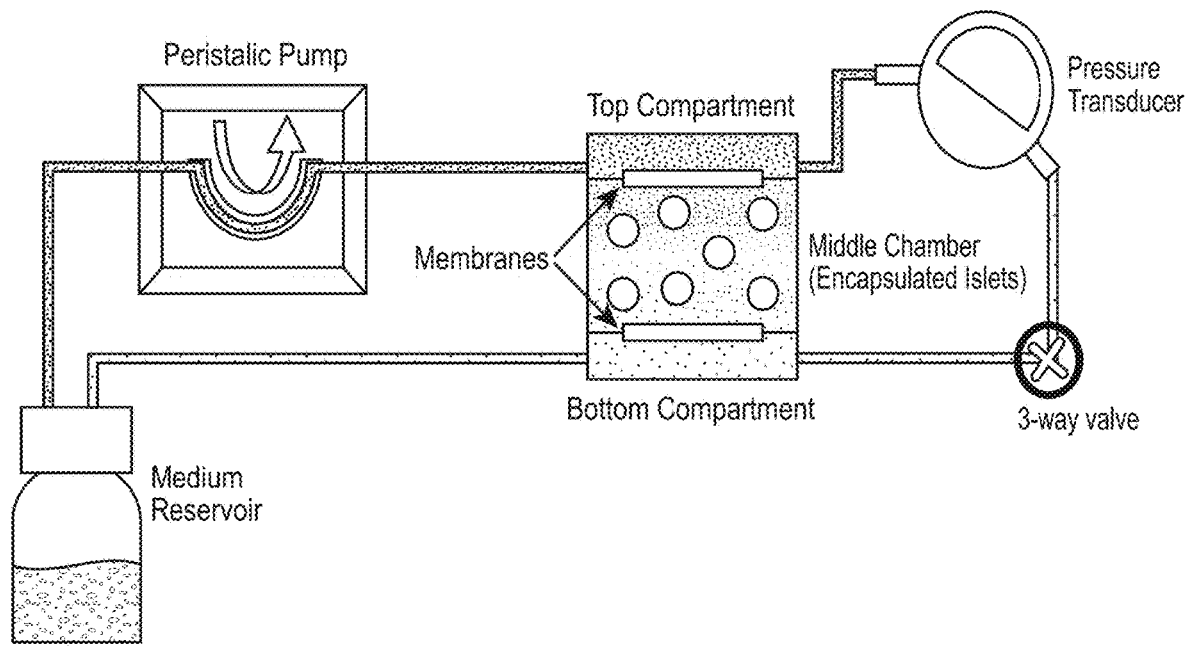
FIG. 7 shows a schematic diagram of the mock-loop circuit for in vitro assessment of SNM-encapsulated islets under convective conditions.

All procedures described involving isolation of mouse islets were performed in accordance with protocols approved by the Institutional Animal Care and Use Committee (IACUC) at the University of California, San Francisco (UCSF). Mouse islets were isolated from 8 to 10-week-old male B6 mice (Jackson Laboratories) based on previously described protocols 40. Harvested islets were maintained in suspension culture with RPMI 1640 with L-glutamine and 11.1 mM glucose (Gibco: 11875-093), 10% fetal bovine serum (FBS) (Gibco: 16000), and 1% penicillin-streptomycin (P/S) (UCSF Cell Culture Facility: CCFGK003). A group of 500 mouse islets were introduced into the middle encapsulation chamber of the mock-loop device (FIG. 7). To evaluate cell performance with cytokine exposure, the circuit reservoir was replaced with culture medium added with TNF-α (1000 U/ml), IFN-γ (1000 U/ml), and IL-1β (50 U/ml) for 6 hrs. Static culture conditions with or without cytokine exposure were used as the controls. Mouse islets were subsequently isolated for viability testing and glucose challenge.

1.3.4 Islet Viability

Islet viability was assessed by double staining with fluorescein diacetate (FDA) (Sigma: F7378) and propidium iodide (PI) (Sigma: 287075) as described by protocol (SOP Document: 3104, A02) from National Institute of Allergy and Infectious Diseases (NIAID). Briefly, mouse islets were incubated in phosphate buffered saline (PBS) containing 0.067 HM FDA and 4.0 HM PI for 30 min and extensively washed in PBS to remove excess staining. Images of mouse islets were obtained using laser scanning Nikon Spectral C1si confocal microscope (Nikon Instruments). Viability of islets was calculated based on the ratio between the number of live cells in the islet and the area of that islet.

1.3.5 Glucose Stimulated Insulin Secretion Assay

Mouse islets retrieved from the middle chamber of the mock-loop circuit were rested in RPMI 1640 containing 30 mg/dL glucose (Gibco: 11879) for 15 minutes before exposed to medium containing 300 mg/dL glucose for 15 minutes. After glucose stimulation, the islets were then returned to medium containing 30 mg/dL glucose. Supernatant was collected every 5 minutes during the series of incubations and insulin content was measured with mouse insulin ELISA kits (Mercodia: 10-1247-01) and normalized by extracted total protein concentration (Thermo: 78505; 23225).

1.4 Statistical Analysis

Sample pairs were analyzed using Student's t-test. Multiple samples were evaluated with oneway or two-way analysis of variance (ANOVA) followed by Bonferroni and multiple comparison using Graphpad Prism software (San Diego, Calif.). A p value of <0.05 was accepted as statistically significant for all analyses.

1.5 Results

MEMS fabrication technologies offers unprecedented potential in reproducibility and precision to engineer controlled pore dimensions that can selectively block the passage of immune components while allowing transport of small molecules (e.g. glucose and insulin) to sustain the viability of the encased cells. In the present study, the permeability and selectivity of the SNM were characterized to prevent cytokine infiltration and assessed the functional performance of SNM-encapsulated mouse islets in a mock-loop device under convective transport.

1.5.1 SNM Design and Fabrication

A new generation of semipermeable membranes, SNM, with slit-pore designs initially investigated by Desai et al. 26, 27. The SNM exhibit a pore size distribution of ~1%, and a consistent pore size control in the range of 5-15 nm (FIG. 1) has been engineered. The slit pore microarchitecture of SNM was achieved by dry oxidation of polysilicon for the growth of silicon dioxide ($SiO_2$) (FIG. 2D) and through backside patterning with deep ion-reactive etching (DRIE) which resulted in vertical sidewalls in each membrane window (FIG. 2H). This process allowed for fabrication of membranes with greater number of exposed nanopores per area. The travel path could be further optimized by lowering the thickness of the membrane which can easily be controlled by the thin film low-pressure chemical vapor deposition (LPCVD) (FIG. 2B) or dry etch process (FIG. 2G).

The utilization of a sacrificial layer to define the nanopores resulted in a membrane with a straight slit pore path that presents a shorter distance for molecules to travel. The permeability-selectivity analysis for ultrafiltration demonstrated that membranes with slit-shaped pores showed higher performance and greater selectivity at a given value of permeability, than membranes with cylindrical pores for pore size below 100 nm. To circumvent the slow concentration-dependent diffusion occurred in size-restricted nanoporous membranes, the concept of using convection-dominated transport is advantageous in terms of creating faster solvent movement under transmembrane pressure gradient, which efficiently drags small molecules such as glucose and insulin across membranes to the encapsulated cells.

1.5.2 SNM Permeability and Selectivity Characterization

Figure 5:
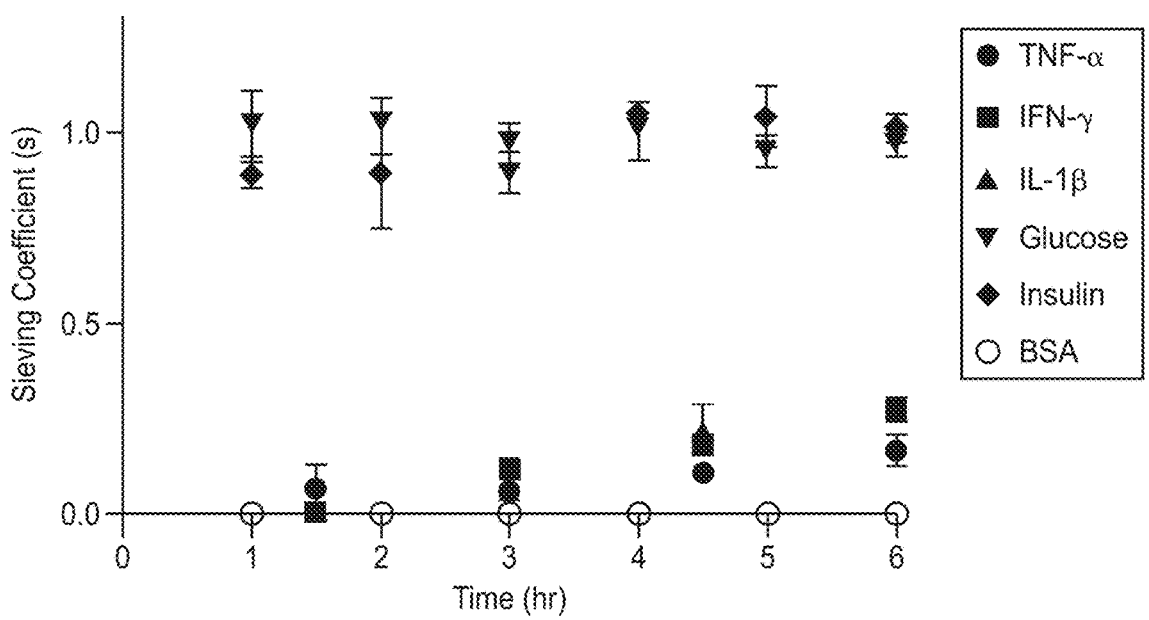
FIG. 5 shows a transport of various molecules through slit-pore of SNM under a pressure difference of ~2 psi.
Figure 10:
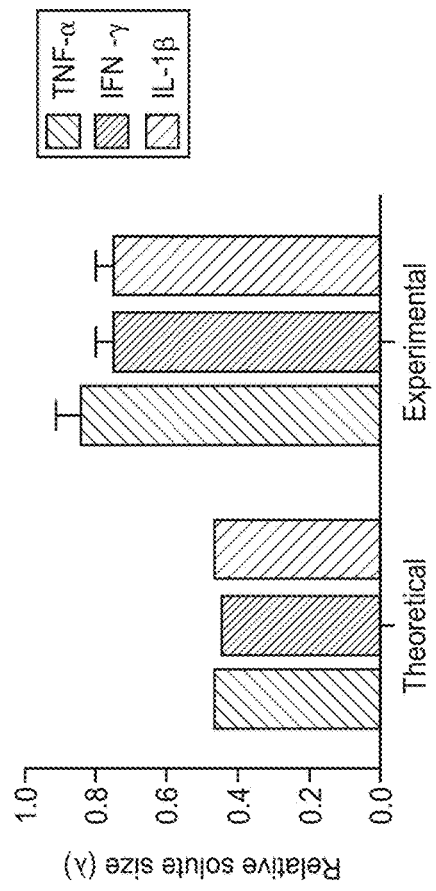
FIG. 10 shows a. comparison of relative solute size (λ).

Permeability and selectivity of the SNM were characterized with the hydraulic permeability testing setup (FIG. 9), which uses liquid flow through planar nanoporous membranes under tangential-flow filtration operation. It was demonstrated that SNM with pore sizes of 7 nm generated a hydraulic permeability of 130 ml/hr/m$^2$/mmHg, which is much greater compared with conventional polymer membranes (~40 ml/hr/m$^2$/mmHg) used in previous bioartificial pancreas devices. To further demonstrate the feasibility of SNM for immunoisolation, the membrane selectivity was characterized against transport of cytokines and small molecules using the pressure-driven ultrafiltration system (FIG. 8). Solute transport was evaluated at ~2 psi driving pressure to mimic the typical physiological pressure difference between artery and vein 38, which results in an ultrafiltration rate of ~4 ul/min. The membrane Peclet number (Pe) for the pressure-driven ultrafiltration system was significantly greater than 1, suggesting that convective transport dominates. The observed sieving coefficients (calculated using Equation. 2) should reflect the rejection characteristics of the membrane. After 6 hours, the sieving coefficients of TNF-α, IFN-γ, and IL-1β were 0.16, 0.27, and 0.27, respectively (FIG. 5). In contrast, the sieving coefficients of glucose and insulin quickly reached 1 (FIG. 5). These data collectively demonstrate that SNM provide about 80% rejection of cytokine passage, while allowing complete transport of small molecules. Because concentration polarization and transmembrane diffusion were negligible in this experimental system, the observed sieving coefficient should be equal to the product of the solution partition coefficient (Φ) and the convective hindrance factor (Kc). Previously, Dechadilok and Deen derived an analytic expression for the product of ΦKc which describes a rigid sphere passing in a slit shaped pore:

$$\Phi K_c = 1 - 3.02\lambda^2 + 5.776\lambda^3 - 12.3675\lambda^4 + 18.9775\lambda^5 - 15.2185\lambda^6 + 4.8525\lambda^7 \quad \text{(Equation 3)},$$

where λ is the relative solute size indicating the ratio between the diameter of the molecule and the width of slit-pore channel. Based on the observed sieving coefficients of cytokines (FIG. 5), the corresponding relative solute sizes λ from Deen's model (Eq. 3) can be calculated for TNF-α, IFN-γ, and IL-1β as 0.83, 0.74, and 0.74, respectively. The experimental relative solute sizes of these cytokines are larger than the theoretic values, as indicated by Stokes-Einstein's radius 14 (FIG. 10). This difference in relative solute sizes between the experimental and theoretical values could be explained by the fact that cytokines are not strictly spherical: TNF-α is a packed cubic shape consisting of trimers formed with β-sheet structure, IFN-γ is a globular dimer with flattened elliptical shaped subunits 52, and IL-1β has β-strands wrapped around in a tetrahedron-like fashion. Furthermore, the electrostatic interactions associated with diffuse electrical double layer (EDL) around charged proteins could also increase the overall molecule size, thereby overestimating the experiment relative solute sizes.

In summary, the SNM enables higher levels of ultrafiltrate production and demonstrate selective rejection against middle molecules like cytokines. Therefore, by encapsulating islets in SNM, it was postulated that the increased convective mass transport of nutrients and glucose can support islet viability and insulin production, while the selective rejection of immune components enables immunoisolation.

1.5.3 Assessment of SNM-Encapsulated Islets Cultured Under Mock-Loop Circuit

Figure 11:
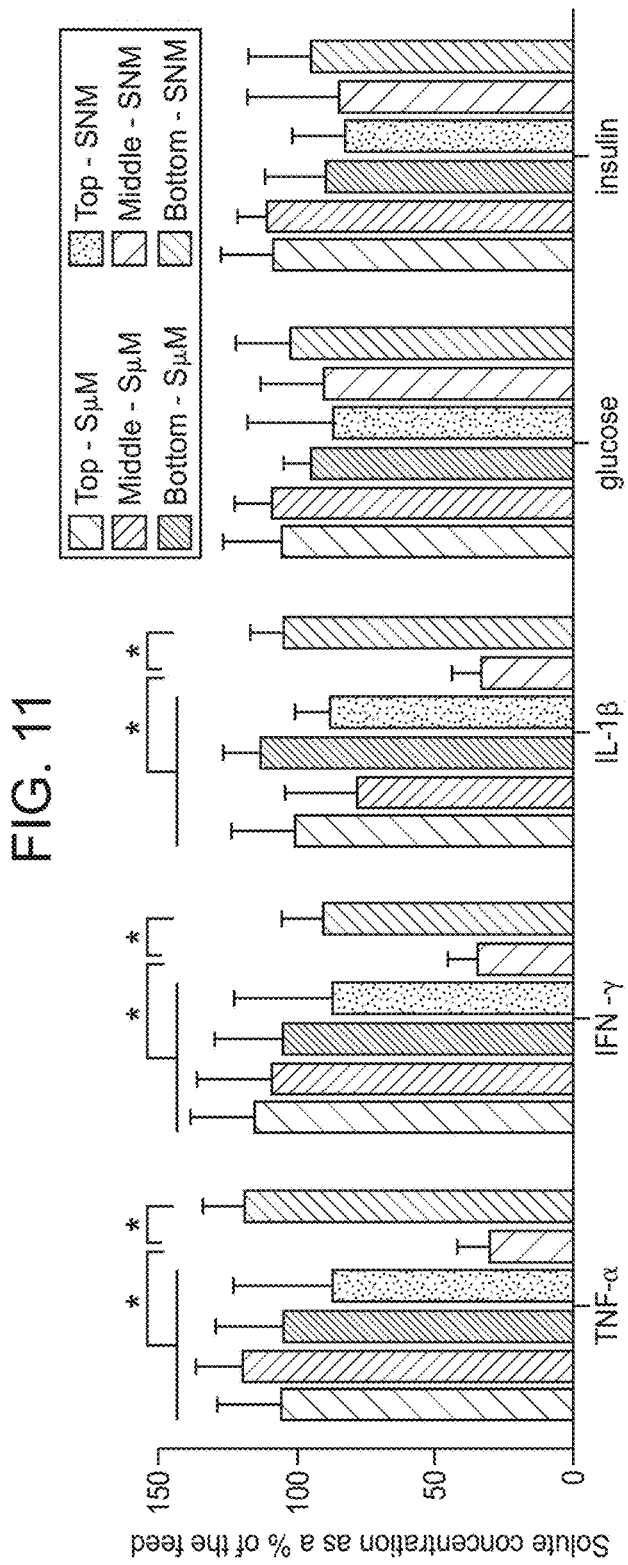
FIG. 11 shows an assessment of solute distribution in the mock-loop system.

The feasibility of developing an implantable SNM-encapsulated bioartificial pancreas device using convective transport was demonstrated using a mock-loop setup. The middle cell chamber is sandwiched between two membranes to closely mimic the in vivo conditions where SNM-encapsulated islets will be mounted as an arterio-venous (AV) graft (FIG. 6). The pressure difference between the artery and vein will generate the ultrafiltrate and drive transport of water, salts, glucose, insulin, and other small molecules through the SNM, while passage of immune components such as cytokines will be blocked. After passing the cytokine-contained media from the reservoir through the mock-loop circuit for 6 hr under applied physiological pressure ~2 psi 38, samples that were collected from the top, middle, and bottom chambers of the flow cell device were compared against the reservoir concentration. The level of cytokines TNF-α, IFN-γ, and IL-1β were significantly reduced to 30%, 35%, and 34% in the middle chamber, whereas small molecules insulin and glucose passed completely (~100%) through both membranes (FIG. 11). To further examine the SNM-encapsulated islets under convective transport in the proposed mock-loop circuit, mouse islets were loaded into the middle chamber with or without cytokine circulation for 6 hr. The static culture incubated with cytokines showed a more than 2.2-fold increase in cell death compared to the static culture without cytokines, mock-loop device without cytokines, and mock-loop flow cell device with cytokines (FIG. 3). Moreover, no significant change in islet viability was observed among the static culture without cytokines, mock-loop device without cytokines, and mock-loop flow cell device with cytokines (FIG. 3). This demonstrated the effectiveness of SNM to protect islets from pro-inflammatory cytokine attack maintaining islet viability.

Figure 4:
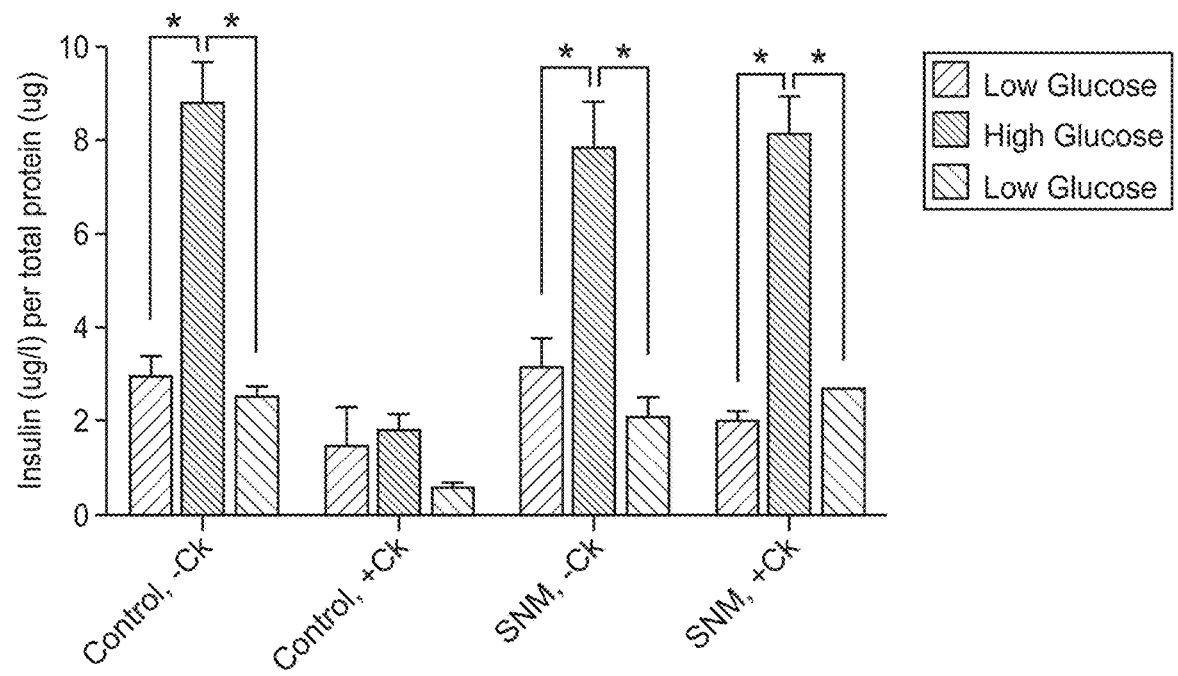
FIG. 4 shows glucose-stimulated insulin release from mouse islets in the SNM-encapsulation chamber and in static culture.

Additionally, the static culture without cytokines, mock-loop device without cytokines, and mock loop flow cell device with cytokines demonstrated a 3.0-fold, 2.6-fold, and 4.1-fold changes, respectively, in the amount of insulin secreted during high glucose challenge compared with those secreted during low glucose challenge, respectively (FIG. 4). However, the static culture incubated with cytokines exhibited little variation in insulin secretion upon changes in glucose level (FIG. 4) due to loss in islet viability (FIG. 3). The glucose challenge demonstrated that the SNM-encapsulated mouse islets responded properly to changes in glucose level, whereas cytokine-infiltrating mouse islets lost their insulin-secreting ability to sense glucose stimuli. These data confirmed the usefulness of SNM to provide desired immunoisolation to support the viability and functional performance of the encapsulated islets.

1.4 Conclusions

An improved silicon nanopore membrane, SNM, for the encapsulation of pancreatic islets under convective flow was developed and characterized. The SNM structure was specifically designed to obtain a well-defined slit pore in the nanometer range with a remarkably high hydraulic permeability. Furthermore, SNM achieved high molecule selectivity against middle molecules such as cytokines under convective transport and provided adequate immunoprotection to the encapsulated islets while generating sufficient filtrate to support viability and functionality of the encapsulated islets.

Example 2

Semipermeable membrane capsules can immunoprotect transplanted islets by blocking passage of the host's immune components while providing exchange of glucose, insulin and other small molecules. However, capsules-based diffusive transport often exacerbates ischemic injury to islets by reducing the rate of oxygen and nutrient transport. The efficacy of a newly-developed semipermeable ultrafiltration membrane, the silicon nanopore membrane (SNM) under convective-driven transport, limits the passage of pro-inflammatory cytokines while overcoming the mass transfer limitations associated with diffusion through nanometer-scale pores. SNM-encapsulated mouse islets perfused in culture solution under convection outperformed those under diffusive conditions in terms of magnitude (1.49-fold increase in stimulation index and 3.86-fold decrease in shut-down index) and rate of insulin secretion (1.19-fold increase and 6.45-fold decrease during high and low glucose challenges) respectively. SNM-encapsulated mouse islets under convection demonstrated rapid glucose-insulin sensing within a physiologically relevant time-scale while retaining healthy islet viability even under cytokine exposure. The encapsulation of islets with SNM under convection improves graft function and survival.

This study showed that SNM and silicon micropore membrane (SμM) with 7 nm and 1000 nm-wide slit-shaped pores respectively, were used to encapsulate mouse islets under diffusive and convective conditions with and without cytokine exposure. The islets were then exposed to varying concentration of glucose inside the reservoir culture medium, and glucose-stimulated insulin responses and islet viability were evaluated. In addition, to determine the immunoprotective effect of the membranes, a highly concentrated cocktail of pro-inflammatory cytokines was added to the circulating system to challenge the encapsulated islets.

Materials and Methods

SNM were designed to have an active membrane area (6×6 mm) consisting of ~$10^6$ rectangular slit pores with an average pore size of 7 nm in width, 2 μm in length, and 300 nm in depth (FIG. 1). The surface of SNM was coated with polyethylene glycol (PEG) to minimize protein fouling. All SNM used in this study exhibited a measured average pore size of ~7 nm post-pegylation. The control silicon micropore membrane (SμM) had the same design, but with an average pore size of 1000 nm. In this study, it was observed how encapsulated islets responded to changes in glucose concentration across a single silicon membrane under convective transport (~2 psi transmembrane pressure) or diffusive transport (0 psi transmembrane pressure) using a pressure-driven filtration circuit. The glucose-insulin response was further tested by using highly concentrated cytokine solution in the circuit. The respective stimulation index (SI) and shut-down index (SDI) of encapsulated islets subsequently analyzed under convective and diffusive conditions. The rate of change in insulin production was also tested based on the slopes of curves that were fitted on glucose-insulin kinetics graphs to describe the quickness of insulin being secreted as glucose concentration changes. Finally, the viability of encapsulated islets was characterized in the pressure-driven filtration assembly under various mass transfer and cytokine exposure conditions.

1.1 Substrate Preparation 1.1.1 Silicon Nanopore Membranes (SNM) and Silicon Micropore Membrane (SμM): Architecture and Fabrication Silicon nanopore membranes (SNM) have been prototyped from silicon substrates by MEMS technology as previously reported 19, 36-37 with some modifications (FIG. 2A-I). Briefly, the process used the growth of a thin SiO2 (oxide) layer on 400 μm-thick double side polished (DSP) silicon wafers followed by a low pressure chemical vapor deposition (LPCVD) of polysilicon (~500 nm). The wafers were then specifically patterned, dry oxidized, wet etched, deposited with a second polysilicon layer, and finally blanket-etched until 400 nm of polysilicon remained and the underlying vertical oxide layer was exposed. The vertical sacrificial oxide layer defined the critical nanoscale pore size of the membranes. The low temperature oxide (LTO) (~1 μm) was deposited onto polysilicon of the wafers to serve as the hard mask for membrane protection. Deep reactive ion etching (DRIE) removed the backside of each window until membranes were disclosed. Eventually, the sacrificial oxide was etched away in 49% hydrofluoric acid (HF) during the final step of the fabrication process to leave behind open nanoscale slit pores. The wafers were subsequently cut into 1×1 cm chips with an effective area of 6×6 mm2 containing 1500 windows each, with a total of 106 pores per membrane. Each rectangular pore was 7 nm in width, 300 nm in depth, and 2 μm in length. Silicon micropore membrane (SμM) were fabricated to produce wafer-scale arrays of 500 nm by 4 μm rectangular slit pores with 1000 nm-wide slit width using similar process. The wafers were diced to form 1×1 cm chips with an effective area of 6×6 mm2 containing 1500 windows each, with a total of 3.126 pores per membrane. All membranes were cleaned using a conventional "piranha" clean procedure, which involved a 20 min-immersion in 3:1 sulfuric acid (H2SO4)/hydrogen peroxide (H2O2) mixture, followed by thorough rinses in deionized (DI) water. Images of SNM were obtained using scanning electron microscope (SEM) (Leo 1550) (FIG. 2A-I).

1.1.2 Surface Modification of SNM with Poly(Ethylene Glycol) (PEG)

SNM were covalently modified with PEG using a previously reported protocol38 with some modifications to prevent protein fouling on the membrane surface. The technique used for PEG attachment involved a single reaction step which covalently couples silicon surface silanol group (Si—OH) to a chain of PEG polymer through a trimethoxysilane group forming a Si—O—Si-PEG sequence. Briefly, SNM were immersed in a solution of 3 mM 2-[methoxy (polyethyleneoxy)propyl]trimethoxysilane (PEG-silane) (Gelest: SIM6492.7) in toluene for 2 hr at 70° C. A series of extensive washing steps involving toluene, ethanol, and DI water were used to rinse away unbounded PEG residue.

1.1.3 Hydraulic Permeability for SNM Pore Size Characterization

An automated mass and pressure measurement system was utilized for characterizing liquid flow through the SNM under a tangential-flow filtration operation.9 The pore size of the SNM can be related to filtration flow parameters using (Equation 1), where h is pore width, μ is the viscosity, l is the membrane thickness, Q is the volumetric flow rate, n is the number of pores per membrane, w is the pore length, and ΔP is the transmembrane pressure. To assemble the overall system for SNM pore size characterization (FIG. 9), air was applied through a syringe pump (Sigma: Z675709) into a water reservoir. Water was circulated by a peristaltic pump (Masterflex: 07551-00) through a differential pressure transducer (Omega: PX429 015GI), a flow cell with enclosed membrane, and returned to the original water reservoir. The flow cell was assembled with the SNM submerged under water to remove air bubbles from all compartments. Specifically, a membrane was positioned with the polysilicon interface facing down with a customized silicone gasket positioned on top of the membrane, followed by the final placement of a filtrate chamber on top of the gasket. All sections were fastened together and secured to the base with hand-tightened hex bolts until the gasket was visibly compressed. The ultrafiltrate permeated through the membrane was routed to a liquid collection container that rested on a precision mass balance (Mettler Toledo: XS205). Measurements from the differential pressure transducer and the mass balance were automatically collected with a data acquisition laptop. A typical membrane hydraulic permeability test consisted of 5 ml/min flow rate and 4 pressure cycles (5, 1, 5, and 1 psi) for durations of 150 s each. Using the specifications for pore length, membrane thickness, and total number of pores provided based on individual wafer designs, the average pore size of SNM was calculated using Equation 1. All SNM membranes in this study were surface-modified with PEG and exhibited an average pore size of ~7 nm.

1.2 Culture of Membrane-Encapsulated Islets in the Pressure-Driven Filtration Assembly All procedures described involving isolation of mouse islets were performed in accordance with protocols approved by the Institutional Animal Care and Use Committee (IACUC) at the University of California, San Francisco (UCSF). Mouse islets were isolated from 8 to 10-week-old male B6 mice (Jackson Laboratories) based on previously described protocols. Harvested islets were maintained in suspension culture with RPMI 1640 with L-glutamine and 11.1 mM glucose (Gibco: 11875-093), 10% fetal bovine serum (FBS) (Gibco: 16000), and 1% penicillin-streptomycin (P/S) (UCSF Cell Culture Facility: CCFGK003).

A mock-loop circuit was assembled with two flow cell components. Briefly, one SNM with customized silicone gasket frames were sandwiched in between two flow cell components. A group of 40-50 mouse islets were introduced into the bottom chamber separated by the SNM from the circulating fluid (5 ml/min) in the top chamber. A peristaltic pump drove the fluid through the top of the flow cell component, and finally back to the original medium reservoir. For convective experiments, a three-way valve was used to create flow resistance for a physiological pressure difference ~2 psi between the top and the bottom compartments of the flow cell. The membrane Peclet number (Pe) for the pressure-driven ultrafiltration system was significantly greater than 1, suggesting that convective transport dominates. For diffusive experiments, no transmembrane pressure was induced and fluid still circulated throughout the system. To study the effects of cytokines on SNM-encapsulated islets, solution consisting of mouse cytokines TNF-α (2,000 U/ml), IFN-γ (1,000 U/ml), and IL-1β (10,000 U/ml) was added to the original reservoir. Silicon membranes with 1 μm-wide slit pores (SμM) were used as the control with adjusted pressure (~0.127 psi) and flow rate (~20 μl/min) to produce similar amount of ultrafiltrate as the SNM in this mock-loop system. Naked mouse islets cultured under static conditions were also used as controls.

1.2.1 Glucose Challenge in the Pressure-Driven Filtration Mock-Loop System

The membrane-encapsulated mouse islets in the mock-loop systems were exposed to a series of low (1.6 mM), high (16.6 mM), and low (1.6 mM) glucose (Gibco: 11879) stimulation for 30 min each. Supernatant was sampled every 10 min from the bottom islet chamber during this series of glucose challenge. For convective experiments, an ultrafiltrate rate of ~3.5 ul/min was observed for the SNM with ~7 nm pore size and the same ultrafiltrate rate was obtained for the SμM with lowered transmembrane membrane pressure and system flow rate. For diffusive experiments, islet chambers were re-filled after individual sampling to ensure that the volume of islet chamber was kept constant at all time. This step minimized the any bubbles that might potentially be formed during the process which could hinder mass transfer within the system. Insulin content was measured with mouse insulin enzyme-linked immunosorbent assay (ELISA) kits (Mercodia: 10-1247-01) with accounted dilutions and normalized by extracted total protein concentration (Thermo: 78505; 23225). Naked mouse islets were also challenged under static culture condition as controls. About 7-10 μl chamber fluid per islet were used in all cases.

1.2.2 Analysis of Stimulation Index (SI) and Shut-Down Index (SDI)

A stimulation index was calculated as the ratio of stimulated to basal insulin secretion. In our study, the stimulation index (SI) was the ratio of (1) the first insulin collection point in the high glucose phase to the last insulin collection point of the previous low glucose phase (Immediate Stimulation), and (2) the highest insulin secretion in the high glucose phase to the last insulin collection point of the previous low glucose phase (Maximum Stimulation). The shut-down index (SDI) was calculated as the ratio of (1) the first insulin collection point in the subsequent low glucose phase to the last insulin collection point in the high glucose phase (Immediate Shutdown), and (2) the lowest insulin secretion in the subsequent low glucose phase to the last insulin collection point in the high glucose phase (Maximum Shutdown). The stimulation index indicates the magnitude of insulin released as stimulated by a higher concentration of glucose, whereas the shut-down index reflects the magnitude of cessation in insulin production once glucose concentration returns to normal.

1.2.3 Analysis of Rate of Change in Insulin Secretion

The rate of change in insulin secretion was calculated for the stimulation and shut-down phases. For the stimulation phase, a curve was fitted on the glucose-insulin kinetic graph with the last point of insulin produced during low glucose exposure to the highest point of insulin produced during high glucose exposure. For the shut-down phase, a curve was fitted on the glucose-insulin kinetic graph with the last point of insulin produced during high glucose exposure to the first point of insulin produced during low glucose exposure. The rate of change was obtained by taking derivatives of those curves to study the quickness of insulin being secreted during changes in glucose concentration.

1.2.4. Islet Viability

Islet viability was assessed by double staining with live green and dead red solutions (Invitrogen: R37601). Briefly, mouse islets were incubated in live green and dead red solutions for 15 min at room temperature followed by extensive washes in PBS to remove excess staining. Images of mouse islets were obtained using laser scanning Nikon Spectral C1si confocal microscope (Nikon Instruments). Viability of islets was calculated based on the percentage of live cells in the islets as described by protocol on assessment of islet viability by fluorescent dyes from Department of Surgery Division of Transplantation at University of Wisconsin-Madison.

1.3 Statistical Analysis

Sample pairs were analyzed using Student's t-test. Multiple samples were evaluated with one-way or two-way analysis of variance (ANOVA) followed by Bonferroni and multiple comparison using Graphpad Prism software (San Diego, Calif.). A p value of <0.05 was accepted as statistically significant for all analyses.

Results and Discussion

A construction of a benchtop flow loop circuit consisting of a single membrane that separated islets from the circulating fluid (FIG. 7). Using this system, the kinetics of glucose-stimulated insulin secretion of SNM- and SµM-encapsulated islets was characterized under both convective and diffusive transport modalities. The effect of cytokine exposure was further analyzed to the function of SNM- and SµM-encapsulated islets by adding a highly concentrated cocktail of pro-inflammatory cytokines including TNF-α, IL-1β, and IFN-γ to the circuit. The ability of membrane-encapsulated islets to secrete insulin upon changes in glucose concentration was characterized by: (1) computing the stimulation index (SI) and shut-down index (SDI) which reflect the magnitude of stimulatory and shut-down insulin response as a function of changes in glucose concentration, respectively; and (2) characterizing the rate of change in insulin secretion as the ambient fluid changed from low-to-high and high-to-low glucose concentrations. The viability of encapsulated-islets was also assessed in the mock-loop circuit at the end of the various experimental conditions.

2.1 Membrane Fabrication and Characteristics

Figure 2D:
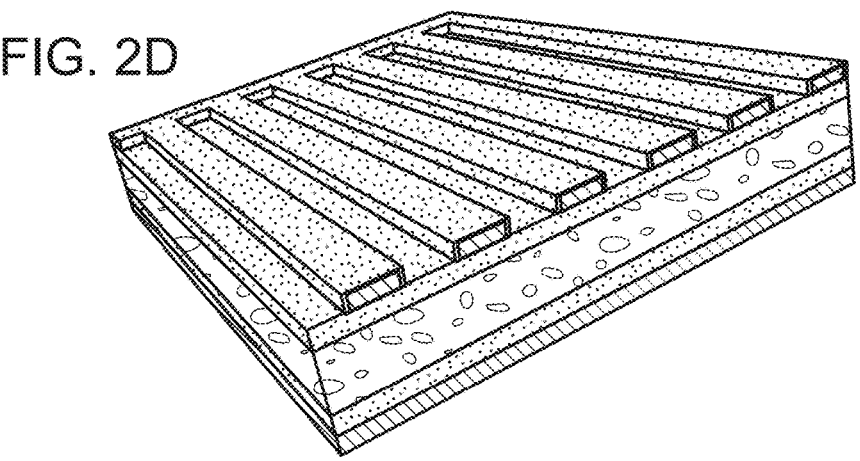
Figure 2E:
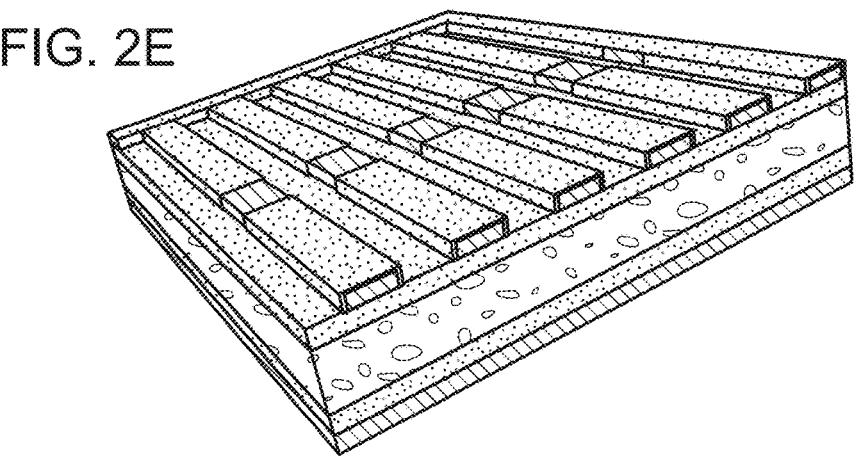

The slit pore microarchitecture of SNM is produced by dry oxidation of polysilicon for the growth of silicon dioxide ($SiO_2$) followed by backside patterning with deep ion-reactive etching (DRIE) that produces vertical walls in each membrane window (FIG. 2A). The SNM wafer is diced into 1 cm×1 cm chips, each with an active membrane area (6×6 mm) consisting of ~$10^6$ rectangular slit pores with ~7 nm width, 300 nm depth, and 2 µm thickness (FIG. 2B-C). Using similar fabrication techniques, silicon micropore membranes (SµM) chips were produced, each with an active membrane area (6×6 mm) consisting of 3.12×$10^6$ rectangular slit pores with ~4000 nm width, 500 nm in depth, and 4 µm in length (FIG. 2D-E). Previously, it was demonstrated that that SNM with ~7 nm pore size resulted in a 3.25-fold increase in hydraulic permeability compared with conventional polymer membranes used in other bioartificial pancreas devices. Whereas the SµM allowed complete passage of all molecules, SNM demonstrated size selectivity with an ~80% rejection of cytokine passage, while allowing complete transport of glucose and insulin.

Figure 13A:
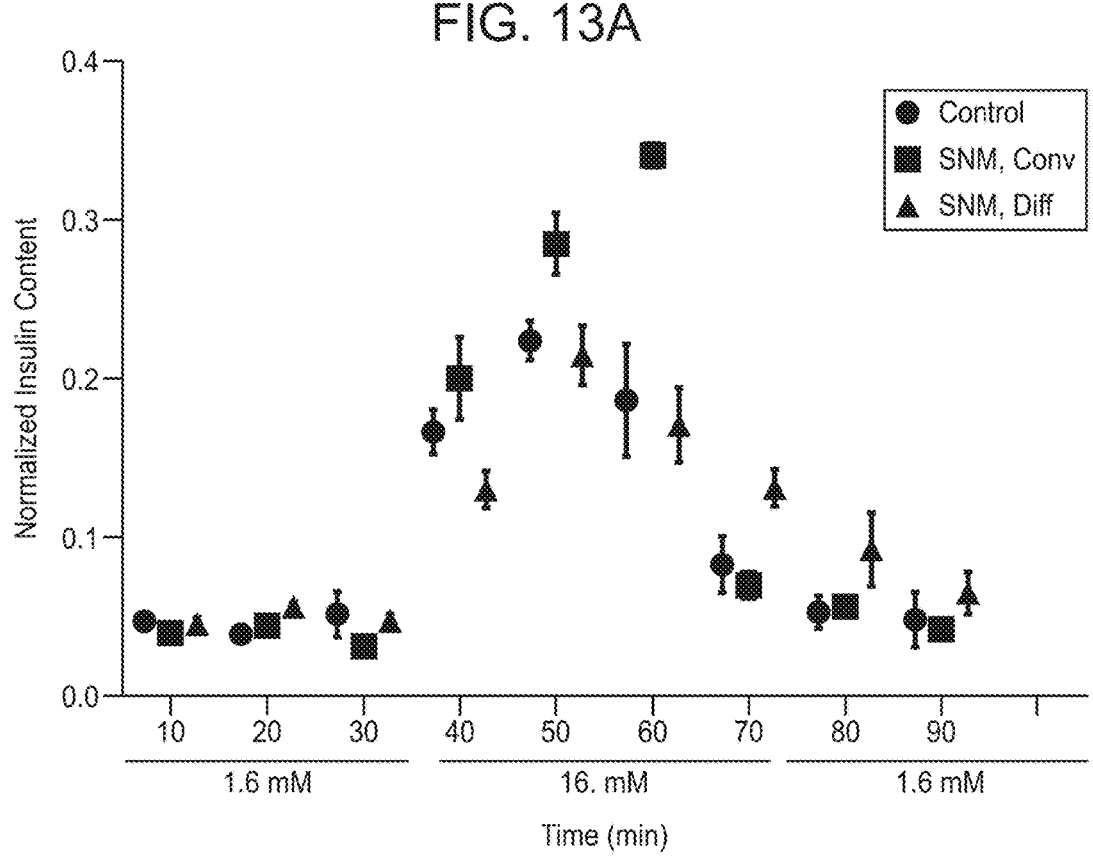
FIGS. 13A-13C show Glucose-insulin kinetics of SNM-encapsulated islets under convection and diffusion without cytokine exposure.
Figure 13B:
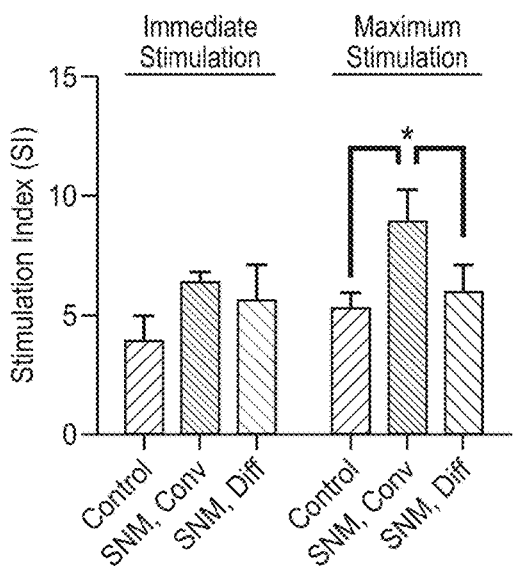

2.2 Kinetics of Glucose-Stimulated Insulin secretion of Encapsulated Islets 2.2.1 No Cytokine Exposure A benchtop flow loop circuit incorporating membrane-encapsulated islets under applied physiological transmembrane pressure (FIG. 9) was used. It was observed how encapsulated islets responded to changes in glucose concentration across a single silicon membrane under convective transport (~2 psi transmembrane pressure) or diffusive transport (0 psi transmembrane pressure) using this flow circuit. Unencapsulated islets cultured under static conditions were used as controls. Islets under all conditions reacted quickly to the high glucose concentration (16.6 mM) within the first 10 minutes by producing more insulin (40 minute time point; FIG. 13A). The unencapsulated islets under static culture and SNM-encapsulated islets under diffusion reached the peak of the response 20 minutes after high glucose exposure, whereas insulin secretion of the SNM-encapsulated islets under convection continued to increase during the entire 30-minute duration of high glucose challenge (FIG. 13A). The quick insulin response within 5-10 minutes of high glucose exposure was consistent with normal functioning islets releasing insulin in a biphasic manner (e.g. the first insulin phase appeared within 5-10 minutes followed by a second sustained phase). Furthermore, the stimulation index (SI), calculated as the ratio of the first insulin collection in the high glucose phase to the last insulin collection in the previous low glucose phase (Immediate Stimulation), were generally comparable among naked islets under static conditions and the SNM-encapsulated islets under convection and diffusion cases, which were 3.92±1.07, 6.38±0.44, and 5.62±1.51, respectively (FIG. 13B). However, when the highest level of insulin secretion from high glucose phase was used to calculate the magnitude of stimulation (Maximum Stimulation), the naked islets under static conditions and SNM-encapsulated islets under convection and diffusion cases showed SI of 5.29±0.69, 8.92±1.35, 5.97±1.16, respectively (FIG. 13B). The SI of SNM-encapsulated islets under convection showed a 1.49-fold increase than that under diffusion.

Figure 13C:
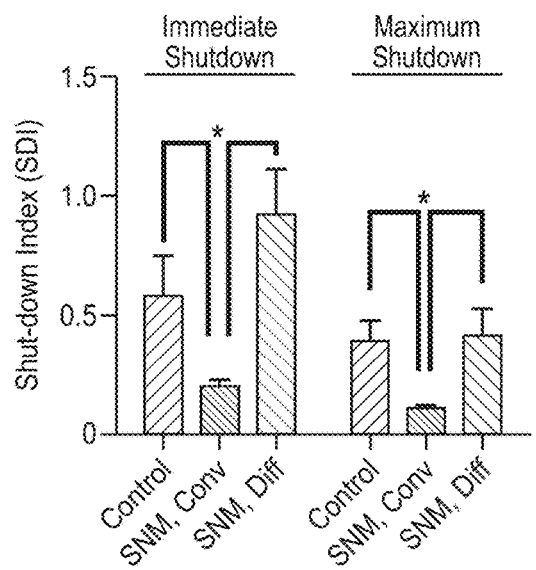

Once the circuit was switched back to low glucose concentration (1.6 mM) from 60 to 90 minutes, the SNM-encapsulated islets under convection exhibited a rapid shut-down in insulin production whereas a gradual decrease in insulin production occurred for the capsule under the diffusive mode. The shut-down index (SDI), calculated as the ratio of the first insulin collection in the subsequent low glucose phase to the last insulin collection in the previous high glucose phase (Immediate Shutdown), showed that the amount of insulin that was secreted significantly decreased for SNM-encapsulated islets under convection (0.20±0.03) compared with the naked islets under static culture (0.59±0.17) and SNM-encapsulated islets under diffusion (0.93±0.19) (FIG. 13C). When the lowest level of insulin secretion from the subsequent glucose phase was used to calculate the magnitude of shut down (Maximum Shutdown), the SDI showed that the amount of secreted insulin significantly decreased for SNM-encapsulated islets under convection (0.11±0.02) compared with the naked islets under static culture (0.40±0.09) and SNM-encapsulated islets under diffusion (0.42±0.11). The SDI of SNM-encapsulated islets under convection showed a 3.86-fold decrease compared to that under diffusion. The slow insulin activation and delayed shut-down response associated with diffusive transport is consistent with previous studies. The SNM-encapsulated islets under convection showed the ability to quickly activate and cease insulin production.

As illustrated in Table 1 of FIG. 18, the rate of change in insulin production was monitored when conditions transitioned from low-high to high-low glucose phases. The rates of change in insulin activation and cessation were on the same scale in the naked islets under static culture as in the SNM-encapsulated islets under diffusion (0.86 and 0.84 for the stimulation and −0.71 and −0.42 for deactivation, respectively; FIG. 18). The SNM-encapsulated islets under convection showed 1.16- and 1.19-fold increase in the rate of glucose-stimulated insulin response and 3.82- and 6.45-fold decrease in the rate of insulin shut-down compared with the naked islets under static culture and SNM-encapsulated islets under diffusion, respectively. In short, the magnitude of glucose-stimulated insulin secretion was higher for SNM-encapsulated islets under convection compared to the naked islets under static culture and SNM-encapsulated islets under diffusion as indicated by the SI (FIG. 13B). The SNM-encapsulated islets under convection showed the fastest rate of insulin production (~1 normalized insulin content min-1 (×10-2)) and cessation (~−2.7 normalized insulin content min-1 (×10-2)) compared to the other two conditions (Table 1).

Further comparison with the silicon micropore membrane (SµM)-encapsulated islets under convection showed that pressure-driven convection yields faster mass transport as the pore size becomes larger (1 µm). The naked islets under static culture, SNM-encapsulated islets under convection, and SµM-encapsulated islets under convection all quickly released more insulin during high glucose exposure from 40 to 60 minutes (FIG. 14A). Whereas the level of insulin plateaued in the naked islets, the amount of secreted insulin increased in the SNM-encapsulated islets under convection from 50 to 60 minutes. However, the SµM-encapsulated islets under convection showed a maximum level of secreted insulin at 50 minutes followed by an immediate concentration drop at 60 minutes. The difference in the glucose-insulin kinetics between SNM- and SµM-encapsulation under convection during high glucose challenge can be explained by: (1) the variation in the ultrafiltration rate produced by two different types of membranes despite efforts to adjust both membranes to obtain the same amount of ultrafiltrate (section 4.2); and (2) possible protein adsorption on the SNM19, 30 that resulted in the lack of negative feedback inhibition of insulin secretion31 due to additional fouling resistance. Furthermore, the SI indicating the magnitude of insulin secretion during pre-stimulation and stimulation (Immediate Stimulation) were higher for SNM- and SµM-encapsulation under convection compared to naked islets under static conditions, which were 6.38±0.44, 6.44±1.41, and 3.92±1.07, respectively (FIG. 14B). When the highest amount of insulin secretion in the high glucose phase was used to calculate SI (Maximum Stimulation), SµM-encapsulation under convection (8.92±1.34) and SµM-encapsulation under convection (11.8±1.64) showed significantly higher SI compared to naked islets under static conditions (5.29±0.69). The SDI calculated from the ratio of insulin secretion from post-stimulation and stimulation (Immediate Shutdown) for SNM- and SµM-encapsulation under convection were 0.20±0.03 and 0.25±0.09, which showed a significant decrease in the magnitude of insulin secreted during low glucose exposure compared to the naked islets (0.59±0.17) (FIG. 14C). This trend was also observed for SNM-encapsulation under convection (0.11±0.02), SµM-encapsulation under convection (0.11±0.01), and the naked islets (0.40±0.09) when the SDI was calculated based on the ratio of lowest insulin secretion from post-stimulation and stimulation (Maximum Shutdown) (FIG. 14C).

In addition, the SµM-encapsulated islets under convection showed the fastest rate of response when switching from low to high glucose condition (3.15 normalized insulin content min-1 (×10$^{-2}$)) to the high to low glucose situation (−3.36 normalized insulin content min-1 (×10$^{-2}$)) (FIG. 18). The SµM-encapsulated islets under convection demonstrated 3.66- and 3.15-fold increase in the rate of glucose-stimulated insulin response, and 4.73- and 1.24-fold decrease in rate of insulin shut-down compared with the naked islets under static culture and SNM-encapsulated islets under convection, respectively (FIG. 18). All rates of change in insulin production and cessation were comparable among the naked islets under static culture, SNM-encapsulated islets under diffusion, and SµM-encapsulated islets under diffusion (FIG. 18). Noticeably, membrane-encapsulation under diffusive scenarios showed a slower insulin response when stimulated with high concentration of glucose (including FIG. 24A-C & FIG. 25A-C). This could be due to the potential formation of boundary layer by adsorption of molecules in the nanoscale pores.19, 30 Depending on the choice of membranes and methods to stimulate the islets (diffusion vs. convection), all experimental conditions had a SI ranging from 2.89 to 6.44 (including FIG. 24A-C & FIG. 25A-C), which is consistent of typical values (2 to 20) for healthy mouse islets.32 Convective conditions with SNM- and SµM-encapsulation outperformed the pure diffusive scenarios during the glucose-insulin activation and shut-down phases. In particular, convective transport with SµM encapsulation demonstrated superior response in insulin activation while the insulin shut-down was observed to be similar for both SNM and SµM encapsulation under convection.

2.2.2 Cytokine Exposure

A highly concentrated solution of pro-inflammatory cytokines consisting of TNF-α, IFN-γ, and IL-1β was used to investigate how the glucose-insulin kinetics of SNM-encapsulated islets are influenced by cytokine exposure. When challenged with high glucose concentration, SNM-encapsulated islets under convection immediately secreted insulin to the maximum level within first 10 minutes followed by a slight decrease in insulin secretion in the next 20 minutes (FIG. 15A). However, SNM-encapsulated islets under diffusion showed an incremental increase in insulin secretion during high glucose exposure. Although an increase in the insulin secretion level for the naked islets under static culture during the high glucose challenge was also observed, the maximum level of insulin secreted was not as amplified as the other two conditions. Furthermore, the magnitude of insulin secretion during pre-stimulation and stimulation (Immediate Stimulation) was significantly different among the naked islets under static conditions, and SNM encapsulation under convection and diffusion as indicated by the SI, which were 2.98±0.06, 6.22±0.69, and 4.29±0.34, respectively (FIG. 15A). When the highest amount of insulin secretion in the high glucose phase was used to calculate SI (Maximum Stimulation), SNM-encapsulation under convection (6.50±0.42) showed an increase in SI compared to SNM-encapsulation under convection (4.99±0.51) and naked islets under static conditions (3.85±1.51) (FIG. 15B). As the circuit was switched back to low glucose concentration, SNM-encapsulated islets under convection showed the most significant drop in insulin secretion compared to the naked islets and SNM encapsulation under diffusion (FIG. 15A). The SDI calculated based on the ratio of insulin secretion from post-stimulation and stimulation (Immediate Shutdown) for naked islets, and SNM encapsulation under convection and diffusion were 1.1±0.36, 0.42±0.19, and 0.8±0.12, respectively (FIG. 15C). The similar trend was observed for SNM-encapsulation under convection (0.26±0.02), SNM-encapsulation under diffusion (0.57±0.15), and the naked islets (0.70±0.12) when the SDI was calculated based on the ratio of lowest insulin secretion from post-stimulation and stimulation (Maximum Shutdown) (FIG. 15C). Further analysis of the rate of change in insulin production from low to high glucose stimulation showed that SNM-encapsulated islets under convection produced 2.89 normalized insulin content min-1 (×10-2), whereas naked islets under static conditions and SNM-encapsulated islets under diffusion produced 0.22 and 0.73 normalized insulin content min-1 (×10$^{-2}$) (Table 2). The rate of change in insulin production from high to low glucose cessation of SNM-encapsulated islets under convection was −1.76 normalized insulin content min-1 (×10$^{-2}$), whereas that of the naked islets under static culture and SNM-encapsulated islets under diffusion were −0.092 and −0.32 normalized insulin content min-1 ($\times 10^{-2}$). The SNM-encapsulated islets under convection exhibited a 13.1- and 3.96-fold increase in the rate of insulin production compared with naked islets and SNM encapsulation under diffusion respectively, when conditions were changed from low to high glucose exposure with cytokines. The SNM-encapsulated islets under convection also demonstrated a 19.1- and 5.5-fold increase in the rate of shutting down insulin secretion from high to low glucose conditions compared with naked islets and SNM encapsulation under diffusion. In summary, the SNM-encapsulated islets under convection exceeded both naked islets and SNM encapsulation under diffusion in terms of the magnitude of insulin produced when stimulated with high level of glucose (FIG. 15B-C) and the rate at which insulin was produced and ceased due to changes in glucose concentration (FIG. 19).

Figure 16A:
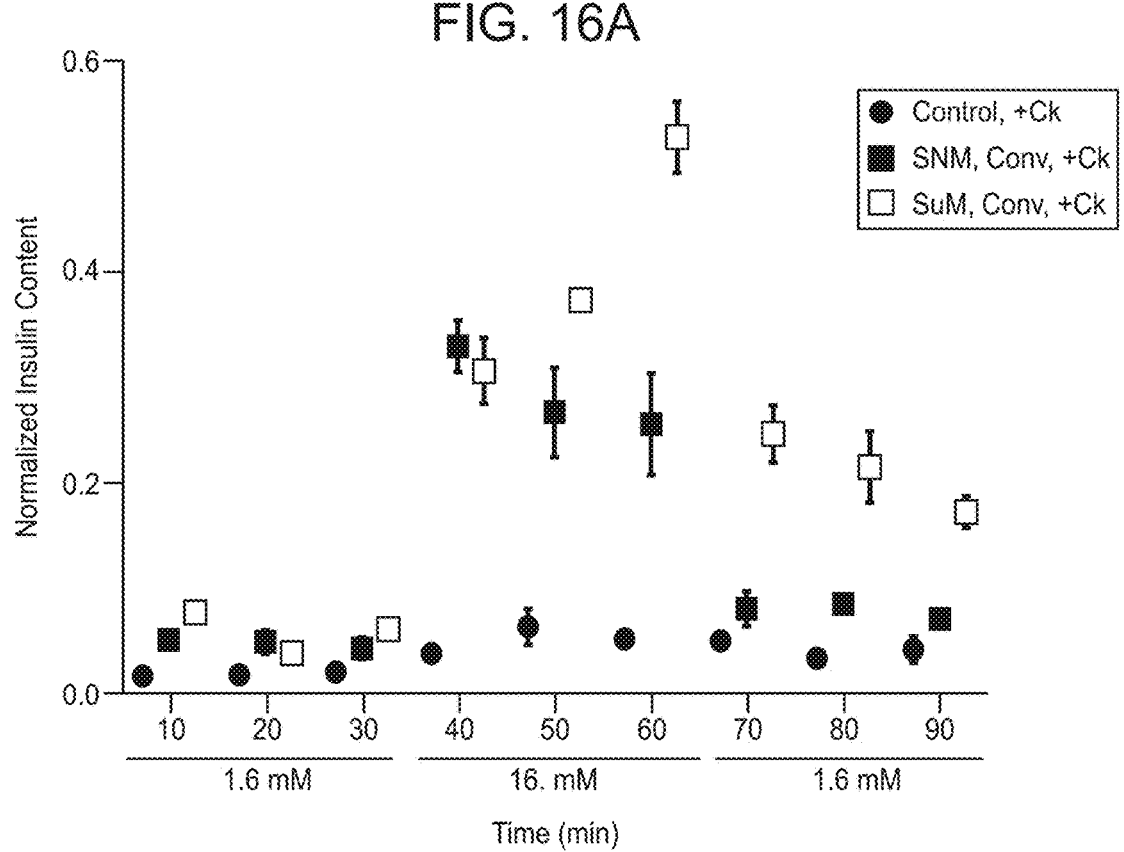
FIGS. 16A-16C show glucose-insulin kinetics of SNM- and SμM-encapsulated islets under convection with cytokine exposure.
Figure 16B:
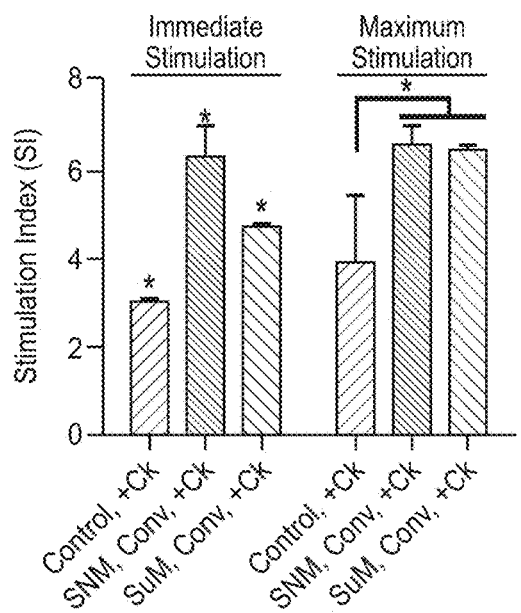
Figure 16C:
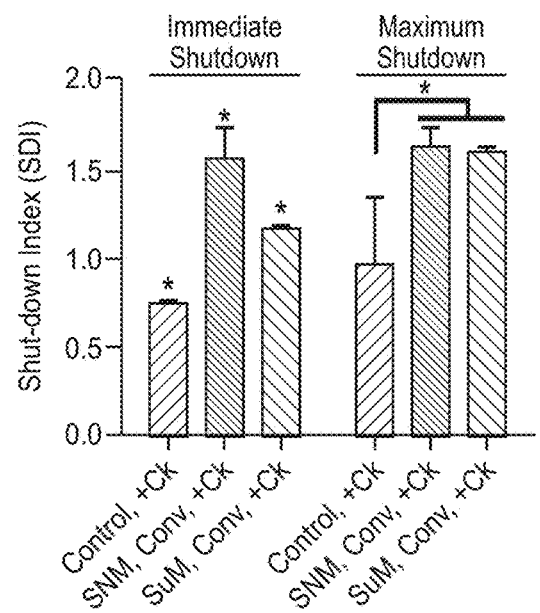

Unlike the SNM-encapsulated islets under convection in which the maximum level of insulin secreted within 10 minutes of high glucose challenge, SμM-encapsulation under convection showed a continuous rise in insulin secretion and reached the highest peak within 30 minutes of high glucose exposure (FIG. 16A). Moreover, SNM-encapsulated islets under convection exhibited the largest magnitude of glucose-stimulated insulin secretion possessing a SI value of 6.22±0.69, which was significantly higher than that for the SμM-encapsulation case with a SI value of 4.66±0.07 (Immediate Stimulation) (FIG. 16B). When the highest amount of insulin secretion in the high glucose phase was used to calculate SI (Maximum Stimulation), SNM- and SμM-encapsulation under convection (6.50±0.42 & 6.37±0.11) showed an increase in SI compared to naked islets under static conditions (3.85±1.51) (FIG. 16B). However, the SDI for immediate shutdown of SNM- and SμM-encapsulated islets under convection were similar in which the SDI were 0.42±0.19 and 0.40±0.04, respectively (FIG. 16C). The same trend was observed when examining the SDI of SNM- and SμM-encapsulation under convection (0.26±0.02 & 0.28±0.04) and the naked islets (0.70±0.12) where the SDI was calculated based on the ratio of lowest insulin secretion from post-stimulation and stimulation (Maximum Shutdown) (FIG. 16C). Further analysis of the rate of changes in insulin production was calculated for SμM-encapsulated islets under convection which showed a 1.46-fold decrease and 1.61-fold increase compared with SNM-encapsulated islets under convection in transitioning from low to high glucose stimulation and from high to low glucose shutdown, respectively (FIG. 19). Noticeably, all diffusive conditions with both SNM- and SμM-encapsulation showed reduction in the magnitude of insulin produced as well as decline in the rate of insulin production compared to all convective scenarios (FIG. 26A-C and FIG. 27A-C, FIG. 29). In summary, convective transport with SNM encapsulation demonstrated better performance than SμM-encapsulation in terms of the magnitude of insulin produced and ceased during high and low glucose phases as indicated by SI and SDI factors under cytokine exposure (FIG. 15A-C and FIG. 16A-C), while the rate of changes in insulin secretion was similar between the two (FIG. 19).

Comparing previous conditions that were not subjected to cytokines, it was observed that conditions with cytokine exposure had a slight decrease in SI values (including FIG. 26A-C and FIG. 27A-C). No significant difference in the magnitude of insulin secreted before and after cytokine exposure for SNM-encapsulation under convection (SI (Immediate Stimulation): 6.38±0.44 and 6.23±0.69, respectively) (FIG. 13B & FIG. 15B) was observed, while the SμM-encapsulation under convection and naked islets under static culture all declined slightly in their SI values (Immediate Stimulation): SμM-encapsulation under convection dropped from 6.44±1.41 to 4.66±0.07 (FIG. 14B & FIG. 16B), and naked islets decreased from 3.92±1.06 to 2.98±0.06 (FIG. 13B & FIG. 15B). The naked islets under static culture showed a higher SDI value (Immediate Shutdown) with cytokine exposure (0.59±0.17) (FIG. 13C) than the no-cytokine condition (1.1±0.36) (FIG. 15C), whereas SNM- and SμM-encapsulation under convection showed consistent SDI values (Immediate Shutdown) before and after cytokines were added (FIG. 13C, FIG. 14C, FIG. 15C; FIG. 16C). When switching from high to low glucose conditions, the naked islets showed a large variation in the SDI value (Immediate Shutdown), indicating partial loss of islet regulatory function with insulin. In contrast, both membrane-encapsulated conditions showed sharp drop in insulin production once they were switched back to low glucose environment (FIG. 15A-C, FIG. 16A-C). Cytokines namely TNF-α, IFN-γ, and IL-1β are known to be synergistically cytotoxic through a cascade of inflammatory events such as production of nitric oxide and chemokines, and trigger of endoplasmic reticulum stress to cause loss of islet viability and functionality. It was speculated that cytokines damaged the naked islets as shown by their changes in SI and SDI values mentioned above, whereas the selectivity of the SNM and SμM membranes hindered cytokine infiltration and preserved islet function.

2.3 Islet Viability

In addition to the glucose-insulin kinetics of SNM- and SμM-encapsulation described above, the islet viability was investigated to understand if cytokines caused excessive islet dysfunction (FIG. 6). The naked islets with cytokine exposure showed significantly more cell death compared to all other groups including SNM- and SμM-encapsulation under convection (FIG. 6,a). All membrane-associated diffusive conditions showed normal health comparable to the untreated naked islets under static culture (Figure S6). Some level of cytokine-induced death damage was observed in the SμM-encapsulation under convection as a result of their inability to completely exclude cytokines likely due to the large membrane pore size (FIG. 17A). However, the islet death in the SμM-encapsulation under convection was not as significant as in the control scenario with naked islets. The SNM-encapsulated islets under convection with cytokine exposure showed similar viability compared to SNM-encapsulating and healthy control conditions without cytokines. These observations confirm that membrane protection afforded by SNM provides sufficient immunoisolation to support viability and functional performance of the encapsulated islets.

Conclusions

In this study, the glucose-insulin kinetics of an improved silicon nanopore membrane was characterized, SNM, for the encapsulation of pancreatic islets under convective flow. The glucose-insulin responsiveness of membrane-encapsulated islets was analyzed under a series of low, high, and low glucose challenge by: (1) SI and SDI values, which show the magnitude of insulin secreted when transitioning from low to high glucose condition or vice versa; and (2) rate of change in insulin secretion, which indicates how quickly the system responds from low to high glucose condition or vice versa. Based on these parameters, it was found that convective mode performed better than diffusive mode in both SNM and SμM encapsulations. In addition, once exposed under cytokines, convective transport with SNM encapsulation demonstrated superior performance over 5μM encapsulation in terms of the magnitude of insulin produced and ceased during high and low glucose phases with healthy islet viability, while the rate of changes in insulin secretion was on the same scale as that for the 5μM encapsulation. In summary, SNM encapsulation under convective transport enables rapid glucose-insulin sensing to activate and cease insulin production based on the surrounding glucose concentration while retaining healthy islet viability even under cytokine exposure. Our data demonstrates the importance of using convective transport to obtain faster insulin activation and shut-down, which is a critical issue to address in many islet-encapsulating devices 5, 35 with undesired delay in glucose-insulin response. Successful islet encapsulation with selective SNM under convective transport could potentially lower the immunosuppressive drugs and their side effects resulted from current therapies, lead to the possibility of using xenogeneic or stem-cell derived cell sources to overcome donor shortage, and reduce dangerous episodes of hypoglycemia for T1D patients in the future.

Figure 1B:
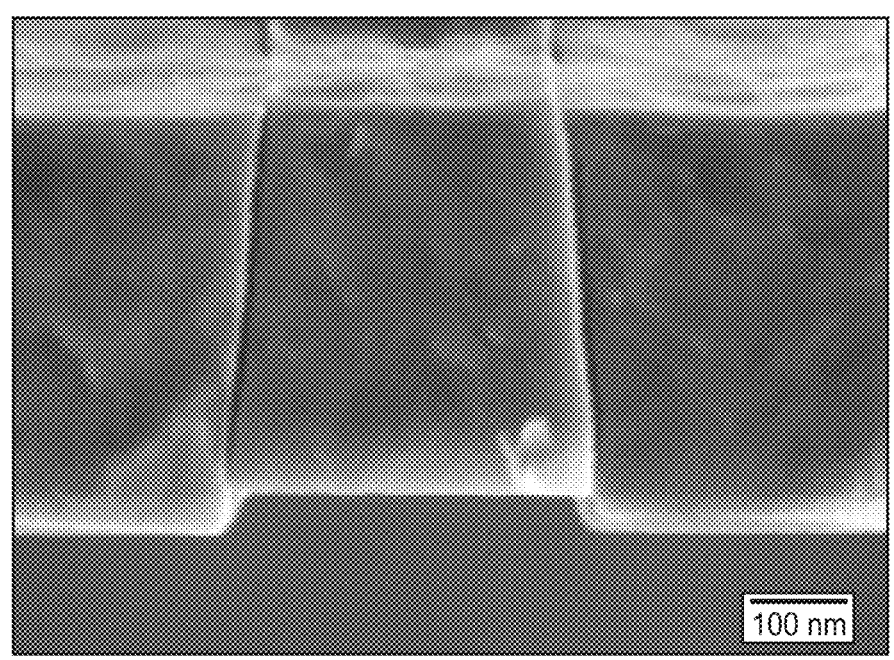

FIG. 1A-B show silicon nanoporous membranes (SNM). FIG. 1A shows an optical image of the SNM chip. FIG. 1B shows an SEM image of the surface of the membrane which illustrates nanopores with 2 um in length. FIG. 1C shows an SEM image of the cross-section of the membrane which illustrates one nanopore with 7 nm in width and 300 nm in depth.

Figure 2F:
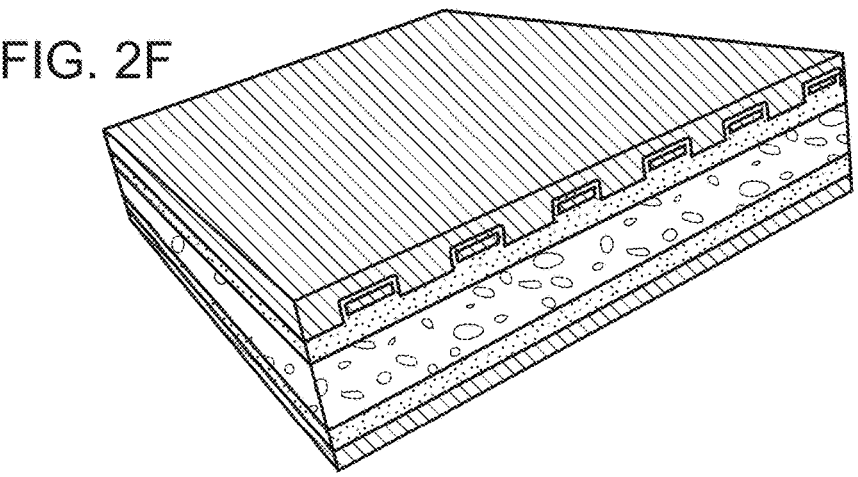

FIG. 2A-G show a schematic for fabrication of silicon nanopore membranes. FIG. 2A shows piranha cleans of double side polished Si wafer. FIG. 2B shows thermal oxidation growth of SiO2 and low pressure chemical vapor deposition (LPCVD) of polysilicon. FIG. 2C shows dry-etch patterning of polysilicon. FIG. 2D shows thermal oxidation growth of SiO2 for use as sacrificial layer defining nanopores. FIG. 2E shows patterning of anchor layer by wet etch. FIG. 2F shows LPCVD of polysilicon. FIG. 2G shows blanket-etch of polysilicon until exposure of vertical $SiO_2$ nanopores. FIG. 2H shows the deposition of low temperature oxide (LTO) for membrane protection and backside etch of membrane with deep reactive ion etching. FIG. 2I shows dry etch removal of LTO and wet etch release of $SiO_2$.

FIG. 3A-D show in vitro viability of mouse islets under cytokine exposure. FIG. 3A shows viability of SNM-encapsulated mouse islets was measured following the 6 hour experiment in which islets were subjected to culture solution circulating the mock-loop circuit at 5 ml/min with a pressure difference of 2 psi. FIG. 3B shows viable (green) and dead (red) cells were stained for control static culture (FIG. 3A-B) and SNM-encapsulated mouse islets (FIG. 3C-D). Experiments with cytokine exposure (indicated by +Ck) consisted of media containing TNF-α, IFN-γ, and IL-1β. The viability of islets was calculated based on the ratio of dead cells (in red) over the islet area. Viabilities of islets in static cultures were evaluated as control for comparison. SNM protected encapsulated mouse islets from pro-inflammatory cytokines (SNM, +Ck), which showed similar viability to SNM-encapsulated mouse islets without cytokine exposure (SNM, −Ck) and control static culture without cytokine exposure (Control, −Ck). Control static culture with cytokine exposure (Control, +Ck) showed significantly more cell death compared with other groups. (n>3, *p<0.05).

FIG. 4 shows glucose-stimulated insulin release of mouse islets in the SNM-encapsulation chamber and in static culture. Islets were subjected to media containing low-glucose, high-glucose, and low-glucose for 15 min each. Experiments with cytokine exposure (indicated by +Ck) consisted of culture solution containing TNF-α, IFN-γ, and IL-1β. The static culture without cytokines (Control, −Ck), mock-loop device without cytokines (SNM, −Ck), and mock-loop flow cell device exposed with cytokines (SNM, +Ck) had a 3.0-fold, 2.6-fold, and 4.1-fold increase in the amount of insulin secreted during high glucose challenge over those secreted during low glucose phase, respectively. However, the control static culture with cytokine exposure (Control, +Ck) secreted limited amount of insulin upon high glucose challenge due to the dead cells damaged by cytokine infiltration. (n>3, *p<0.05).

FIG. 5 shows a transport of various molecules through slit-pore of SNM under a pressure difference of ~2 psi. Sieving coefficients (S) were expressed as the ratio of the concentration of the filtrate over the concentration of the feed (means±SE). BSA was used as a negative control. Results showed that the sieving coefficients of TNF-α, IFN-γ, and IL-1β were 0.16, 0.27, and 0.27 after 6 hours, respectively. The sieving coefficients of glucose and insulin quickly reached 1. These data indicated that small molecules such as glucose and insulin completely passed the SNM whereas the entry of cytokines was greatly hindered under convective transport.

FIG. 6 shows a conceptual illustration of the implantable intravascular bioartificial pancreas device in the arm of a T1D patient. Transplanted islets will be encapsulated between two SNM sheets mounted on as an arterio-venous (AV) graft. The arterio-venous pressure differential will generate ultrafiltrate that continuously support the islets, which will, in turn, sense glucose levels and produce insulin that will be swept into the venous blood. The small pore size of the SNM ensures appropriate immunoisolation between the transplanted islets and host.

FIG. 7 shows a schematic diagram of the mock-loop circuit for in vitro assessment of SNM-encapsulated islets under convective conditions. A peristaltic pump circulated liquid through the top compartment of the flow cell, a pressure transducer, a 3-way valve, the bottom compartment of the flow cell, and finally back to the original reservoir. The flow cell was composed of two membranes dividing the flow cell into three compartments, where islets were placed inside the middle chamber. Ultrafiltrate flow occurred within the middle chamber between two semipermeable membranes as the top membrane was adjacent to a highpressure "arterial" blood channel and the second membrane was adjacent to a low-pressure "vein" blood channel. The 3-way valve was used to create a pressure difference of ~2 psi between the top and the bottom compartment mimicking the physiological condition.

FIG. 8 shows a schematic diagram of the pressure-driven cytokine filtration testing system. A peristaltic pump circulated liquid through a flow cell that connected to a 3-way valve to establish transmembrane pressure. The permeated ultrafiltrate through the membrane was collected at various time for up to 6 hrs.

Figure 9:
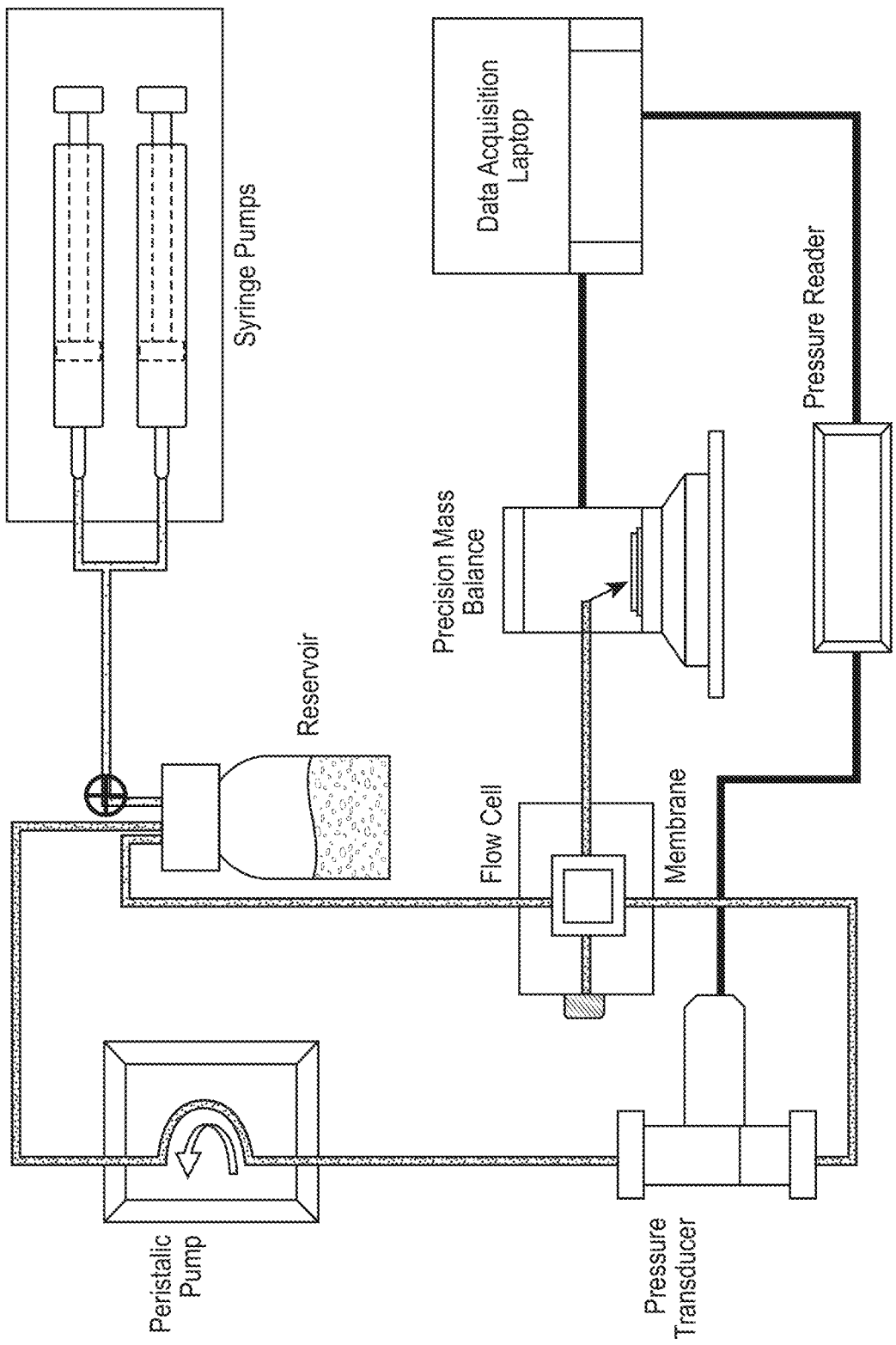
FIG. 9 shows a schematic diagram of the hydraulic permeability testing system. Air was applied through a pressure regulator into the liquid reservoir.

FIG. 9 shows a schematic diagram of the hydraulic permeability testing system. Air was applied through a pressure regulator into the liquid reservoir. A peristaltic pump circulated this liquid through the flow cell with enclosed membrane. The flow cell connected to a differential pressure transducer that was automatically controlled by a data acquisition laptop to adjust the transmembrane pressure. The permeated ultrafiltrate was collected into a liquid container on top of a precision mass balance. Data from the differential pressure transducer and the mass balance were automatically collected and stored in a data acquisition laptop.

FIG. 10 shows a. comparison of relative solute size (λ). Experimental relative solute size (mean} SE) is calculated based on the sieving coefficients for cytokines at 6 hrs. Theoretical values were determined using the Stokes-Einstein's equation 14.

FIG. 11 shows an assessment of solute distribution in the mock-loop system. The mock-loop circuit was composed of two membranes dividing the flow cell into the top, middle, and the bottom compartments. Concentration of solutes from each chamber was assessed at the end of the 6 hr experiment and was expressed as a percentage (mean} SE) relative to that of the feed solution. Silicon micropore membrane (SHM) consisted of 1000 nm diameter slit pores were used as control. The data showed that the amount of TNF-α, IFN-γ, and IL-1β were significantly reduced to 30%, 35%, and 34% in the middle chamber, whereas small molecules insulin and glucose passed completely (~100%) through SNM under convective flow. However, all molecules including cytokines passed into the middle chamber that were sandwiched between SHM. (n>3, *p<0.05).

Figure 12B:
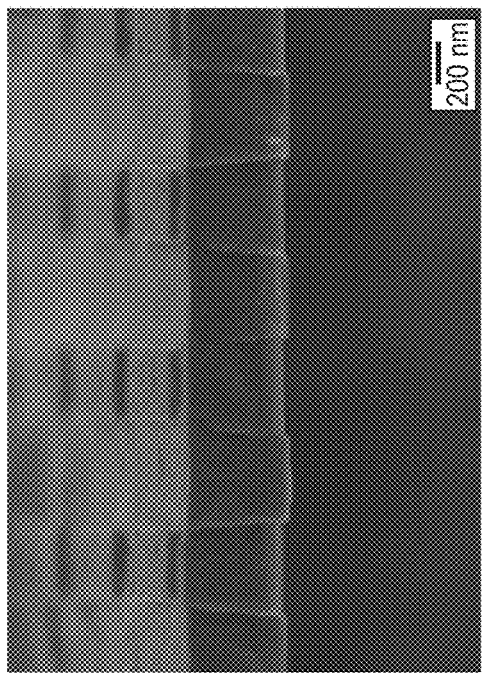
FIG. 12B shows an SEM image of the cross-section of the membrane which depicts nanopores with 7 nm in width and 300 nm in depth.
Figure 12D:
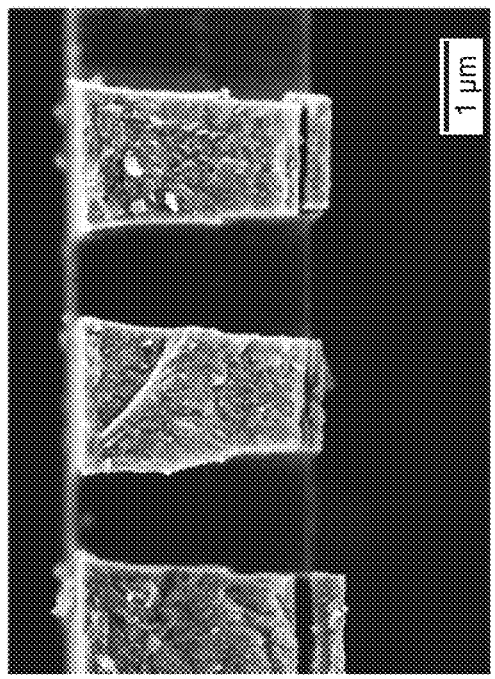
FIG. 12D shows an SEM image of the cross-section of the membrane which depicts micropores with 1 μm in width.
Figure 12A:
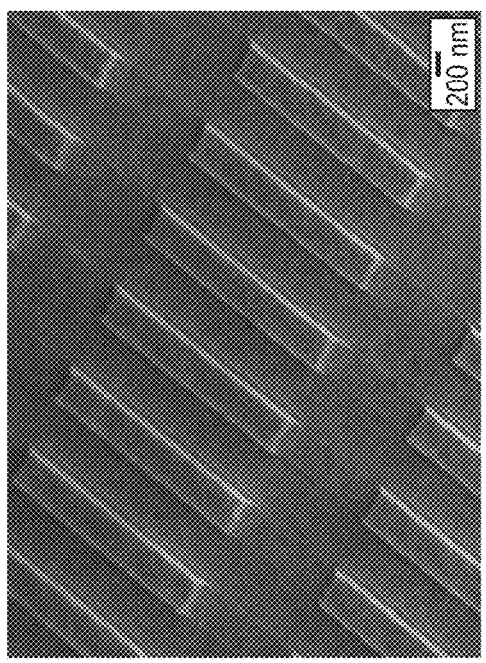
FIG. 12A shows an SEM image of the tilted membrane surface which depicts nanopores with 2 μm in length.
Figure 12C:
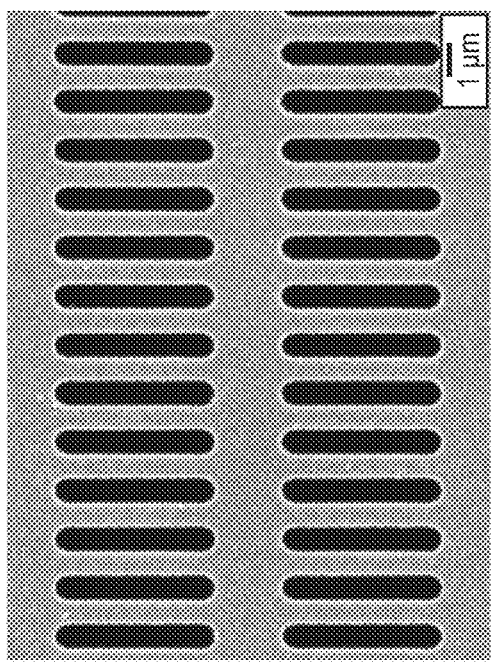
FIG. 12C shows an SEM image of the membrane surface which depicts micropores with 4 μm in length.

FIG. 12A shows an SEM image of the tilted membrane surface which depicts nanopores with 2 μm in length. FIG. 12B shows an SEM image of the cross-section of the membrane which depicts nanopores with 7 nm in width and 300 nm in depth. FIG. 12C shows an SEM image of the membrane surface which depicts micropores with 4 μm in length. FIG. 12D shows an SEM image of the cross-section of the membrane which depicts micropores with 1 μm in width.

FIG. 13A-C shows Glucose-insulin kinetics of SNM-encapsulated islets under convection and diffusion without cytokine exposure. FIG. 13A shows insulin release kinetics of SNM-encapsulated mouse islets during 90-minute low-high-low (1.6 mM, 16.6 mM, 1.6 mM) glucose stimulation under convective (2 psi) (Conv) and diffusive transport (Diff) without subjection to cytokines. The naked islets cultured under static conditions were served as controls (Control). The SNM-encapsulated islets under convective transport (SNM, Conv) exhibited higher insulin secretion following stimulation at high glucose concentration and faster insulin release kinetics in response compared to those under diffusive transport (SNM, Diff). (Mean±SEM, n≥3). FIG. 13B shows the stimulation index (SI) was calculated as the ratio of (1) the first insulin collection in the high glucose phase at 40 minutes to the last insulin collection point of the previous low glucose phase at 30 minutes (Immediate Stimulation), and (2) the highest insulin secretion in the high glucose phase to the last insulin collection point of the previous low glucose phase at 30 minutes (Maximum Stimulation). The SI indicates the magnitude of insulin released as stimulated by a higher concentration of glucose. Without cytokine exposure, SNM-encapsulated islets under convection (SNM, Conv) and diffusion (SNM, Diff) in addition to the naked islets cultured under static conditions (Control) all exhibited similar magnitude of glucose-induced insulin secretion when transitioning from low glucose to high glucose (Immediate Stimulation). However, the SI of SNM-encapsulated islets under convection (SNM, Conv) was the highest compared to that under diffusion (SNM, Diff) and the naked islets cultured under static conditions (Control) when the highest insulin secretion in the high glucose phase was used (Maximum Stimulation). (Mean±SEM, n≥3). FIG. 13C shows that the shut-down index (SDI) was the ratio of (1) the first insulin collection point in the subsequent low glucose phase at 70 minutes to the last insulin collection point in the high glucose phase at 60 minutes (Immediate Shutdown), and (2) the lowest insulin secretion in the subsequent low glucose phase to the last insulin collection point in the high glucose phase at 60 minutes (Maximum Shutdown). The SDI reflects the magnitude of cessation in insulin production once glucose concentration returns to normal. Without cytokine exposure, SNM-encapsulated islets under convection (SNM, Conv) exhibited the highest magnitude of insulin reduction compared to the diffusive condition (SNM, Diff) and the naked islet culture (Control) as glucose dropped low (Immediate Shutdown & Maximum Shutdown). (Mean±SEM, n≥3, *p<0.05).

FIG. 14A-C shows glucose-insulin kinetics of SNM- and SμM-encapsulated islets under convection without cytokine exposure. FIG. 14A shows insulin release kinetics of SNM- and SμM-encapsulated mouse islets during 90-minute low-high-low (1.6 mM, 16.6 mM, 1.6 mM) glucose stimulation under convective (2 psi) (Conv) without subjection to cytokines. The naked islets cultured under static conditions were served as controls (Control). Without cytokine exposure, the SμM-encapsulated islets under convective transport (SμM, Conv) exhibited higher insulin secretion following stimulation at high glucose concentration and faster insulin release kinetics in response to glucose compared to the SNM-encapsulated islets under convective transport (SNM, Conv). (Mean±SEM, n≥3). FIG. 14B shows that the stimulation index (SI) was calculated as the ratio of (1) the first insulin collection in the high glucose phase at 40 minutes to the last insulin collection point of the previous low glucose phase at 30 minutes (Immediate Stimulation), and (2) the highest insulin secretion in the high glucose phase to the last insulin collection point of the previous low glucose phase at 30 minutes (Maximum Stimulation). The SI indicates the magnitude of insulin released as stimulated by a higher concentration of glucose. Without cytokine exposure, the SNM- and SμM-encapsulated islets under convection (SNM, Conv & SμM, Conv) all showed a higher magnitude of secreted insulin compared to the naked islets cultured under static conditions (Control). Furthermore, the SI of SμM-encapsulated islets under convection (SμM, Conv) was the greatest compared to that for the SNM (SNM, Conv) and naked islets cultured under static conditions (Control) when the highest insulin secretion in the high glucose phase was used (Maximum Stimulation). (Mean±SEM, n≥3). FIG. 14C shows that the shut-down index (SDI) was the ratio of (1) the first insulin collection point in the subsequent low glucose phase at 70 minutes to the last insulin collection point in the high glucose phase at 60 minutes (Immediate Shutdown), and (2) the lowest insulin secretion in the subsequent low glucose phase to the last insulin collection point in the high glucose phase at 60 minutes (Maximum Shutdown). The SDI reflects the magnitude of cessation in insulin production once glucose concentration returns to normal. Without cytokine exposure, both SNM- and SμM-encapsulated islets under convection (SNM, Conv & SμM, Conv) exhibited significant magnitude of insulin reduction compared to the islets cultured under static conditions (Control) once glucose dropped back low (Immediate Shutdown & Maximum Shutdown). (Mean±SEM, n≥3, *p<0.05).

FIG. 15A-C shows glucose-insulin kinetics of SNM-encapsulated islets under convection and diffusion with cytokine exposure. FIG. 15A shows insulin release kinetics of SNM-encapsulated mouse islets during 90-minute low-high-low (1.6 mM, 16.6 mM, 1.6 mM) glucose stimulation under convective (2 psi) (Conv) and diffusive transport (Diff) with subjection to cytokines (+Ck). Experiments with cytokine exposure (+Ck) consisted of media containing TNF-α (2,000 U/mL), IFN-γ (1,000 U/mL), and IL-1β (10,000 U/mL). The naked islets cultured under static conditions served as controls (Control, +Ck). The SNM-encapsulated islets under convective transport (SNM, Conv, +Ck) exhibited higher insulin secretion following stimulation at high glucose concentration and faster insulin release kinetics in response compared to those under diffusive transport (SNM, Diff, +Ck) and naked islets cultured under static conditions (Control, +Ck). (Mean±SEM, n≥3). FIG. 15B shows the stimulation index (SI) was calculated as the ratio of (1) the first insulin collection in the high glucose phase at 40 minutes to the last insulin collection point of the previous low glucose phase at 30 minutes (Immediate Stimulation), and (2) the highest insulin secretion in the high glucose phase to the last insulin collection point of the previous low glucose phase at 30 minutes (Maximum Stimulation). The SI indicates the magnitude of insulin released as stimulated by a higher concentration of glucose. With cytokine exposure (+Ck), all conditions including SNM-encapsulated islets under convection (SNM, Conv) and diffusion (SNM, Diff), and the naked islets cultured under static conditions (Control) exhibited varying level of magnitude in glucose-induced insulin secretion (Immediate Stimulation). However, when using the highest insulin secretion in the high glucose phase (Maximum Stimulation), the calculated SI was the highest for SNM-encapsulated islets under convection (SNM, Conv) compared to that under diffusion (SNM, Diff) and naked islets cultured under static conditions (Control). (Mean±SEM, n≥3, *p<0.05). FIG. 15C shows the shut-down index (SDI) that was calculated as the ratio of (1) the first insulin collection point in the subsequent low glucose phase at 70 minutes to the last insulin collection point in the high glucose phase at 60 minutes (Immediate Shutdown), and (2) the lowest insulin secretion in the subsequent low glucose phase to the last insulin collection point in the high glucose phase at 60 minutes (Maximum Shutdown). The SDI reflects the magnitude of cessation in insulin production once glucose concentration returns to normal. With cytokine exposure (+Ck), the SNM-encapsulated islets under convection (SNM, Conv) exhibited the highest magnitude of insulin reduction compared to the diffusive condition (SNM, Diff) and the naked islet culture (Control) as glucose dropped low (Immediate Shutdown & Maximum Shutdown). (Mean±SEM, n≥3, *p<0.05).

FIG. 16A-C show glucose-insulin kinetics of SNM- and SµM-encapsulated islets under convection with cytokine exposure. FIG. 16A shows Insulin release kinetics of SNM- and SµM-encapsulated mouse islets during 90-minute low-high-low (1.6 mM, 16.6 mM, 1.6 mM) glucose stimulation under convective (2 psi) (Conv) with subjection to cytokines (+Ck). The naked islets cultured under static conditions served as controls (Control, +Ck). Experiments with cytokine exposure (+Ck) consisted of media containing TNF-α (2,000 U/mL), IFN-γ (1,000 U/mL), and IL-1β (10,000 U/mL). With cytokine exposure (+Ck), the SµM-encapsulated islets under convective transport (SµM, Conv) exhibited a continuous insulin secretion following stimulation at high glucose concentration from 40 minutes to 60 minutes, while the SNM-encapsulated islets under convection (SNM, Conv) showed a plateau in insulin production during this period of challenge. (Mean±SEM, n≥3). FIG. 16B shows the stimulation index (SI) was calculated as the ratio of (1) the first insulin collection in the high glucose phase at 40 minutes to the last insulin collection point of the previous low glucose phase at 30 minutes (Immediate Stimulation), and (2) the highest insulin secretion in the high glucose phase to the last insulin collection point of the previous low glucose phase at 30 minutes (Maximum Stimulation). The SI indicates the magnitude of insulin released as stimulated by a higher concentration of glucose. With cytokine exposure (+Ck), the SNM- and SµM-encapsulated islets under convection (SNM, Conv & SµM, Conv) and the naked islet culture under static conditions (Control) all showed a significant difference in the magnitude of insulin secreted upon high glucose challenge (Immediate Stimulation). However, the SNM- and SµM-encapsulated islets under convection (SNM, Conv & SµM, Conv) showed greater difference in the magnitude of insulin secreted upon high glucose challenge when the highest insulin secretion was used (Maximum Stimulation). (Mean±SEM, n≥3, *p<0.05). FIG. 16C shows that the shut-down index (SDI) was the ratio of (1) the first insulin collection point in the subsequent low glucose phase at 70 minutes to the last insulin collection point in the high glucose phase at 60 minutes (Immediate Shutdown), and (2) the lowest insulin secretion in the subsequent low glucose phase to the last insulin collection point in the high glucose phase at 60 minutes (Maximum Shutdown). The SDI reflects the magnitude of cessation in insulin production once glucose concentration returns to normal. With cytokine exposure (+Ck), the SNM- and SµM-encapsulated islets under convection (SNM, Conv & SµM, Conv) exhibited the highest magnitude of insulin reduction compared to the naked islet culture (Control) as glucose dropped low (Immediate Shutdown & Maximum Shutdown). (Mean±SEM, n≥3, *p<0.05).

FIG. 17A-B show in-vitro viability of mouse islets. FIG. 17A shows viability of mouse islets was measured following the 90-minute low-high-low (1.6 mM, 16.6 mM, 1.6 mM) glucose stimulation in which islets were subjected to the mock-loop circuit with (+Ck) or without cytokine exposure for SNM- and SµM-encapsulation under convection (SNM, C & SµM, C). The naked islet culture under static culture with cytokine exposure (Control, +Ck) showed significantly less viability compared to all other conditions. (Mean±SEM, n≥3, *p<0.05). FIG. 17B shows viable (green) and dead (red) cells were stained for control static culture without cytokines (A: Control), control static culture with cytokines (B: Control, +Ck), SNM-encapsulated mouse islets under convection without cytokines (C: SNM, C), SNM-encapsulated mouse islets under convection with cytokines (D: SNM, C, +Ck), SµM-encapsulated mouse islets under convection without cytokines (E: SµM, C), and SµM-encapsulated mouse islets under convection with cytokines (F: SµM, C, +Ck). Experiments with cytokine exposure (indicated by +Ck) consisted of media containing TNF-α, IFN-γ, and IL-1β. Both control static culture with cytokines (B: Control, +Ck) and SµM-encapsulated mouse islets under convection with cytokines (F: SµM, C, +Ck) showed a higher level of islet damage compared to other groups, however, the viability of SµM-encapsulated mouse islets under convection with cytokines (F: SµM, C, +Ck) was not statistically significant (n.s.) (FIG. 17A).

FIG. 18 shows the rate of change in insulin secretion without cytokine exposure in Table 1. The rate of change in insulin production was calculated based on the slopes of curves that were fitted on glucose-insulin kinetics graphs to describe the quickness of insulin being secreted as glucose concentration changes. Without subjection to cytokines, SµM-encapsulated mouse islets under convection (SµM, Conv) showed the fastest response following high glucose exposure while SNM- and SµM-encapsulated mouse islets under convection (SNM, Conv & SµM, Conv) exhibited similar rate of insulin cessation when glucose concentration returned to normal.

FIG. 19 shows the rate of change in insulin secretion with cytokine exposure in Table 2. The rate of change in insulin production was calculated based on the slopes of curves that were fitted on glucose-insulin kinetics graphs to describe the quickness of insulin being secreted as glucose concentration changes. With subjection to cytokines (+Ck), SNM-encapsulated mouse islets under convection (SNM, Conv) showed the fastest response following high glucose exposure while SNM- and SµM-encapsulated mouse islets under convection (SNM, Conv & SµM, Conv) exhibited similar rate of insulin cessation when glucose concentration returned to normal.

FIG. 20A-D shows an illustration of the process and fixtures for Cell Scaffold construction. FIG. 20A presents the laser cut acrylic sheet on top of the silicone wire holder. FIG. 20B shows red wires in place to create the ultrafiltrate channels. FIG. 20C presents the purple islet agarose gel poured into the laser cut void of the acrylic sheet. FIG. 20D illustrates the completed Cell Scaffold after removal of red wires and silicone wire holders.

FIG. 21 shows a zoomed-in view of the components of the bioartificial device.

FIG. 22 shows the inlet and outlet components of the bioartificial device. The assembled iBAP is used for both in vitro and in vivo experiments.

Figure 23A:
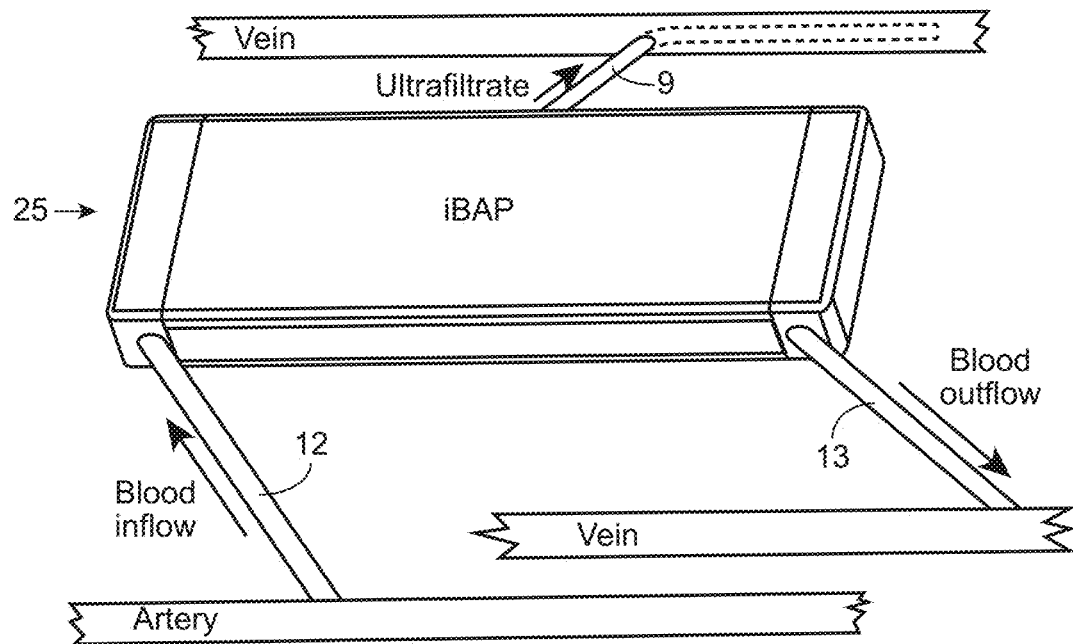
FIGS. 23A-23B show an illustration of the bioartificial device connected inline to an arterial-venous graft and an ultrafiltrate catheter delivering insulin rich ultrafiltrate to a vein.
Figure 23B:
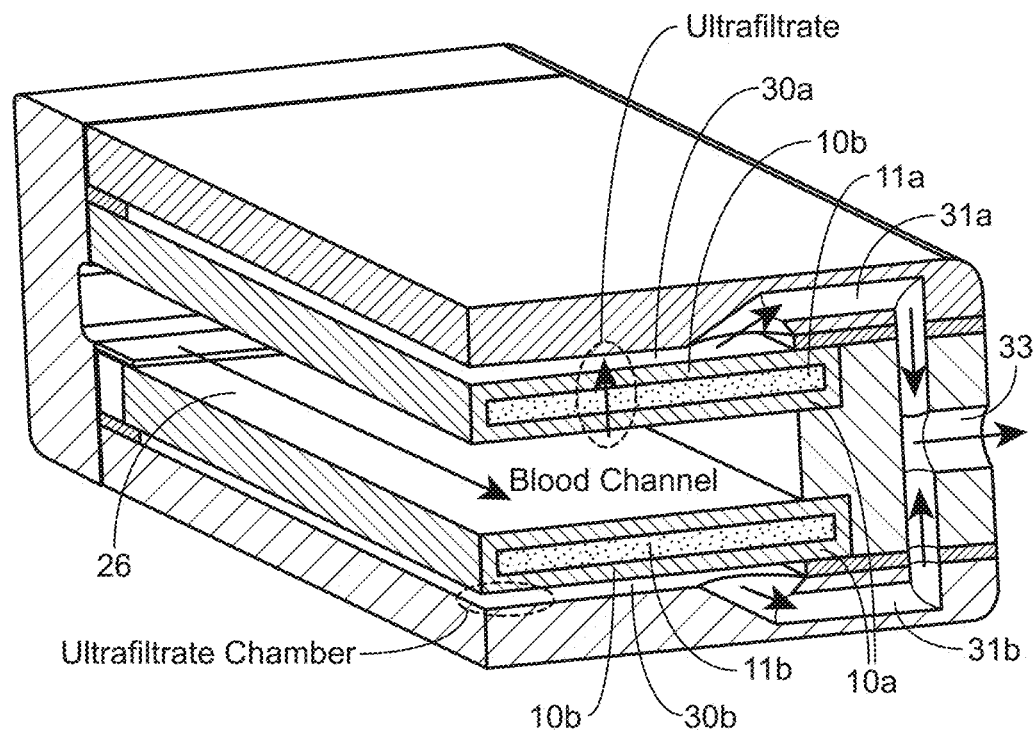

FIG. 23A-B shows an illustration of the bioartificial device connected inline to an arterial-venous graft and an ultrafiltrate catheter delivering insulin rich ultrafiltrate to a vein. FIG. 23B shows a cross-sectional view along the axial and perpendicular directions of flood flow illustrating a single blood channel surrounded by the SNM (green) encapsulated IC (blue) on both sides. Ultrafiltrate crosses the SNM encapsulated inlet chamber into the ultrafiltrate chamber and then flows along the ultrafiltrate flow path to the ultrafiltrate outlet.

FIG. 24A-C show glucose-insulin kinetics of SµM-encapsulated islets under convection and diffusion without cytokine exposure. FIG. 24A shows insulin release kinetics of SµM-encapsulated mouse islets during 90-minute low-high-low (1.6 mM, 16.6 mM, 1.6 mM) glucose stimulation under convective (2 psi) (Conv) and diffusive transport (Diff) without subjection to cytokines. The naked islets cultured under static conditions served as controls (Control). The SµM-encapsulated islets under convective transport (SµM, Conv) exhibited higher insulin secretion following stimulation at high glucose concentration and faster insulin release kinetics in response compared to those under diffusive transport (SµM, Diff). (Mean±SEM, n≥3). FIG. 24B shows the stimulation index (SI) was calculated as the ratio of (1) the first insulin collection in the high glucose phase at 40 minutes to the last insulin collection point of the previous low glucose phase at 30 minutes (Immediate Stimulation), and (2) the highest insulin secretion in the high glucose phase to the last insulin collection point of the previous low glucose phase at 30 minutes (Maximum Stimulation). The SI indicates the magnitude of insulin released as stimulated by a higher concentration of glucose. Without cytokine exposure, SµM-encapsulated islets under convection (SµM, Conv) and diffusion (SµM, Diff) in addition to the naked islets cultured under static conditions (Control) all exhibited similar magnitude of glucose-induced insulin secretion (Immediate Stimulation). However, the SµM-encapsulated islets under convection (SµM, Conv) showed the highest magnitude of insulin secreted when the highest insulin secretion in the high glucose phase was used (Maximum Stimulation). (Mean±SEM, n≥3). FIG. 24C shows the shut-down index (SDI) was the ratio of (1) the first insulin collection point in the subsequent low glucose phase at 70 minutes to the last insulin collection point in the high glucose phase at 60 minutes (Immediate Shutdown), and (2) the lowest insulin secretion in the subsequent low glucose phase to the last insulin collection point in the high glucose phase at 60 minutes (Maximum Shutdown). The SDI reflects the magnitude of cessation in insulin production once glucose concentration returns to normal. Without cytokine exposure, SµM-encapsulated islets under convection (SµM, Conv) exhibited the highest magnitude of insulin reduction compared to the diffusive condition (SµM, Diff) and the naked islet culture (Control) as glucose dropped low (Immediate Shutdown). When the lowest insulin secretion in the low glucose phase was used, SµM-encapsulated islets under convection (SµM, Conv) also showed the largest magnitude of insulin reduction (Maximum Shutdown). (Mean±SEM, n≥3, *p<0.05).

Figure 25A:
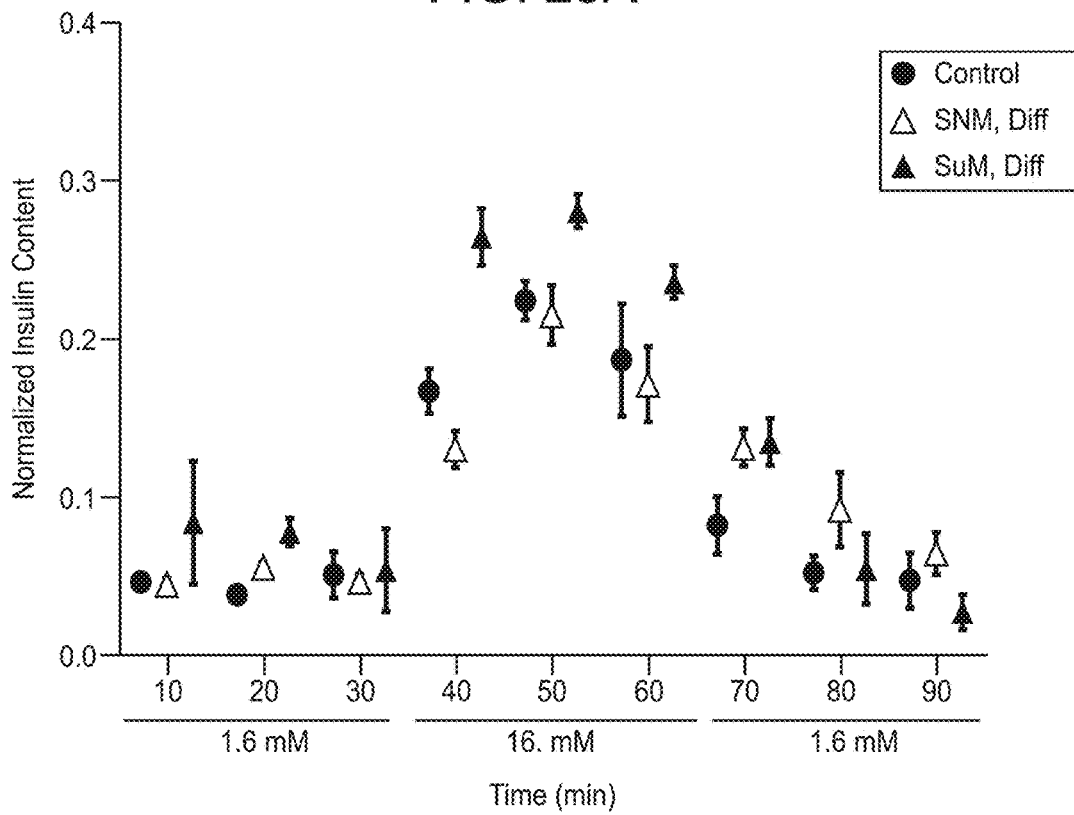
FIGS. 25A-25C show glucose-insulin kinetics of SNM- and SμM-encapsulated under diffusion without cytokine exposure.
Figure 25B:
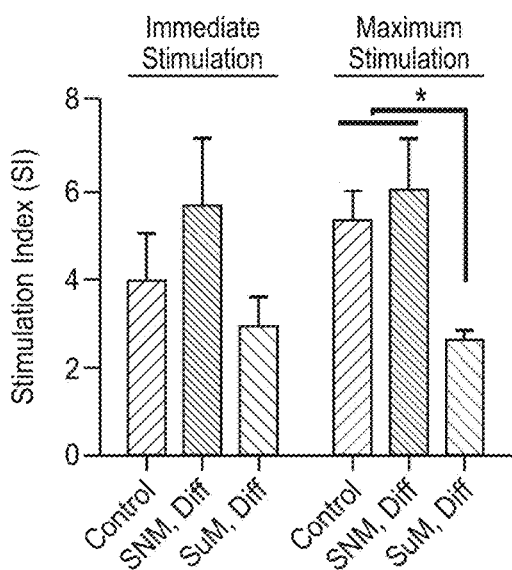
Figure 25C:
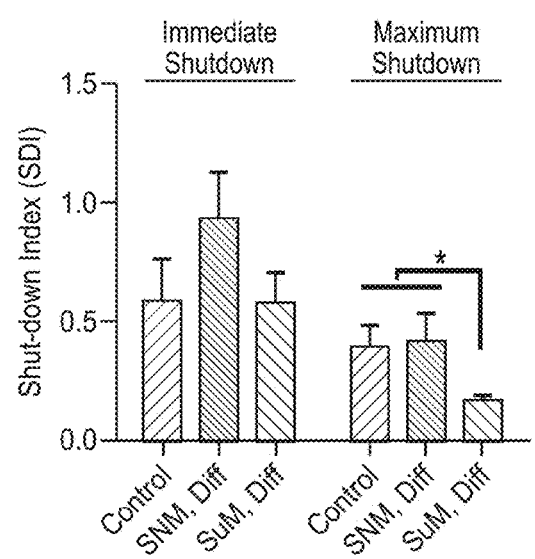

FIG. 25A-C show glucose-insulin kinetics of SNM- and SµM-encapsulated under diffusion without cytokine exposure. FIG. 25A shows insulin release kinetics of SNM- and SµM-encapsulated mouse islets during 90-minute low-high-low (1.6 mM, 16.6 mM, 1.6 mM) glucose stimulation under diffusion (2 psi) (Diff) without subjection to cytokines. The naked islets cultured under static conditions served as controls (Control). Without cytokine exposure, SµM-encapsulated islets under diffusive transport (SµM, Diff) exhibited higher insulin secretion that slowly plateaued following stimulation at high glucose concentration compared to the SNM-encapsulated islets under diffusive transport (SNM, Diff). (Mean±SEM, n≥3). FIG. 25B shows the stimulation index (SI) was calculated as the ratio of (1) the first insulin collection in the high glucose phase at 40 minutes to the last insulin collection point of the previous low glucose phase at 30 minutes (Immediate Stimulation), and (2) the highest insulin secretion in the high glucose phase to the last insulin collection point of the previous low glucose phase at 30 minutes (Maximum Stimulation). The SI indicates the magnitude of insulin released as stimulated by a higher concentration of glucose. Without cytokine exposure, the SNM- and SµM-encapsulated islets under diffusion (SNM, Diff & SµM, Diff) all showed a similar magnitude of insulin secretion compared with the naked islets cultured under static conditions (Control) (Immediate Stimulation). Moreover, the SNM-encapsulated islets under diffusion (SNM, Diff) and naked islets cultured under static conditions showed an increase in SI compared to the SµM-encapsulated islets under diffusion (SµM, Diff) when the highest insulin secretion in the high glucose phase was used (Maximum Stimulation). (Mean±SEM, n≥3). FIG. 25C shows the shut-down index (SDI) was the ratio of (1) the first insulin collection point in the subsequent low glucose phase at 70 minutes to the last insulin collection point in the high glucose phase at 60 minutes (Immediate Shutdown), and (2) the lowest insulin secretion in the subsequent low glucose phase to the last insulin collection point in the high glucose phase at 60 minutes (Maximum Shutdown). The SDI reflects the magnitude of cessation in insulin production once glucose concentration returns to normal. Without cytokine exposure, SNM- and SµM-encapsulated islets under diffusion (SNM, Diff & SµM, Diff) exhibited similar magnitude of insulin reduction compared to the islets cultured under static conditions (Control) once glucose dropped back low (Immediate Shutdown). However, the level of shut down was more significant in SµM-encapsulated islets under diffusion (SµM, Diff) than in the other two conditions (SNM, Diff & Control) when the lowest insulin secretion was used (Maximum Shutdown). (Mean±SEM, n≥3, *p<0.05).

Figure 26A:
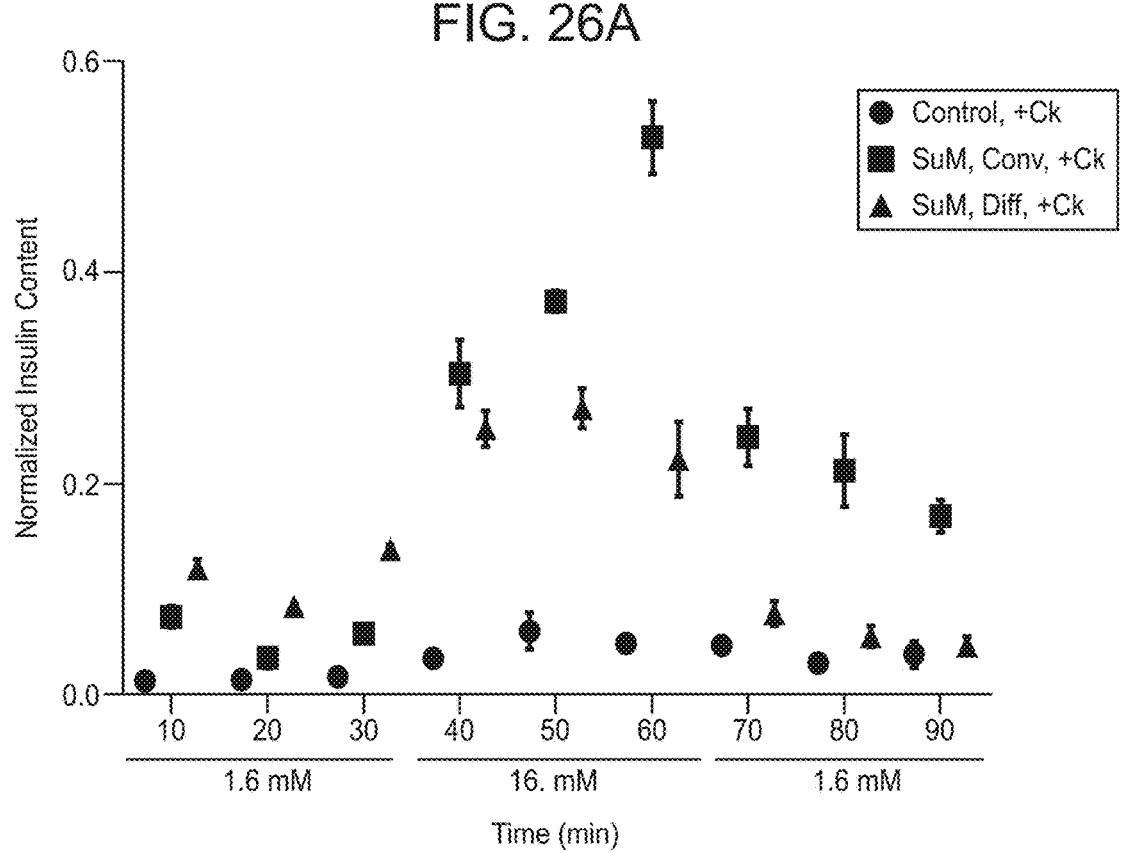
FIGS. 26A-26C show glucose-insulin kinetics of SμM-encapsulated islets under convection and diffusion with cytokine exposure.
Figure 26B:
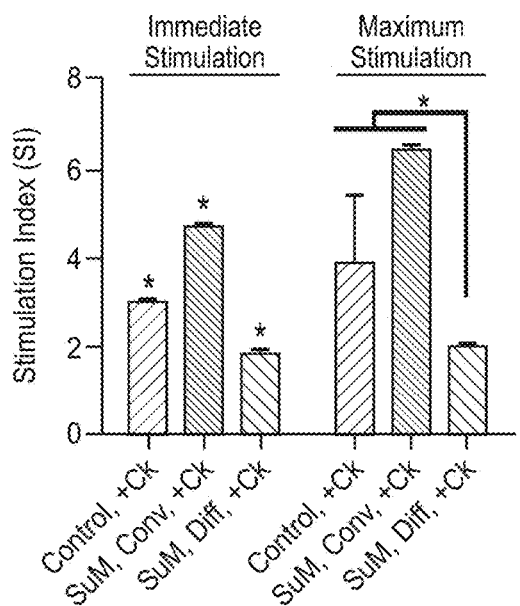
Figure 26C:
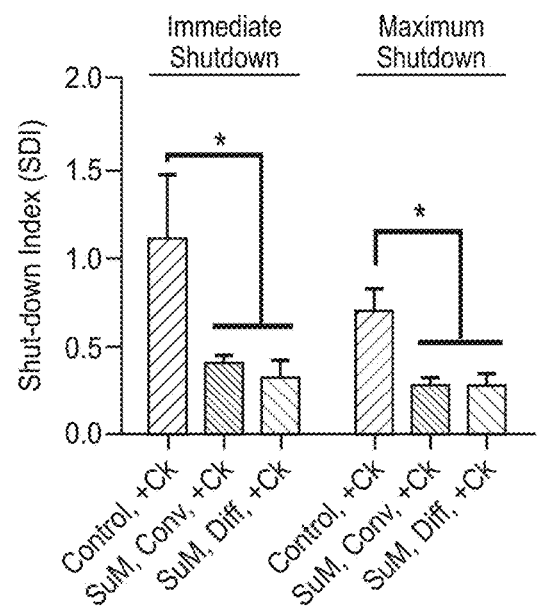

FIG. 26A-C show glucose-insulin kinetics of SµM-encapsulated islets under convection and diffusion with cytokine exposure. FIG. 26A shows insulin release kinetics of SµM- encapsulated mouse islets during 90-minute low-high-low (1.6 mM, 16.6 mM, 1.6 mM) glucose stimulation under convective (2 psi) (Conv) and diffusive transport (Diff) with subjection to cytokines (+Ck). Experiments with cytokine exposure (+Ck) consisted of media containing TNF-α (2,000 U/mL), IFN-γ (1,000 U/mL), and IL-1β (10,000 U/mL). The naked islets cultured under static conditions served as controls (Control, +Ck). The SµM-encapsulated islets under convective transport (SµM, Conv, +Ck) exhibited higher insulin secretion and faster insulin release kinetics in response to stimulation at high glucose concentration compared to those under diffusive transport (SµM, Diff, +Ck) and naked islets cultured under static conditions (Control, +Ck). (Mean±SEM, n≥3). FIG. 26B shows the stimulation index (SI) was calculated as the ratio of (1) the first insulin collection in the high glucose phase at 40 minutes to the last insulin collection point of the previous low glucose phase at 30 minutes (Immediate Stimulation), and (2) the highest insulin secretion in the high glucose phase to the last insulin collection point of the previous low glucose phase at 30 minutes (Maximum Stimulation). The SI indicates the magnitude of insulin released as stimulated by a higher concentration of glucose. With cytokine exposure (+Ck), all conditions including SµM-encapsulated islets under convection (SµM, Conv) and diffusion (SµM, Diff), and the naked islets cultured under static conditions (Control) exhibited varying level of magnitude in glucose-induced insulin secretion (Immediate Stimulation). The SµM-encapsulated islets under convection (SµM, Conv) and naked islets cultured under static conditions (Control) showed an increase in the magnitude of insulin secretion when the highest insulin secretion in the high glucose phase was used (Maximum Stimulation). (Mean±SEM, n≥3, *p<0.05). FIG. 26C shows the shut-down index (SDI) was the ratio of (1) the first insulin collection point in the subsequent low glucose phase at 70 minutes to the last insulin collection point in the high glucose phase at 60 minutes (Immediate Shutdown), and (2) the lowest insulin secretion in the subsequent low glucose phase to the last insulin collection point in the high glucose phase at 60 minutes (Maximum Shutdown). The SDI reflects the magnitude of cessation in insulin production once glucose concentration returns to normal. With cytokine exposure (+Ck), the SµM-encapsulated islets under convection (SµM, Conv) and under diffusion (SµM, Diff) both exhibited the highest magnitude of insulin reduction compared to the naked islet culture (Control) as glucose dropped low (Immediate Shutdown & Maximum Shutdown). (Mean±SEM, n≥3, *p<0.05).

FIG. 27A-C show glucose-insulin kinetics of SNM- and SµM-encapsulated islets under diffusion with cytokine exposure. FIG. 27A shows insulin release kinetics of SNM- and SµM-encapsulated mouse islets during 90-minute low-high-low (1.6 mM, 16.6 mM, 1.6 mM) glucose stimulation under diffusion (Diff) with subjection to cytokines (+Ck). The naked islets cultured under static conditions served as controls (Control, +Ck). Experiments with cytokine exposure (+Ck) consisted of media containing TNF-α (2,000 U/mL), IFN-γ (1,000 U/mL), and IL-1β (10,000 U/mL). With cytokine exposure (+Ck), the SµM-encapsulated islets under diffusive transport (SµM, Diff) exhibited the fastest insulin secretion at high glucose concentration from 40 minutes to 60 minutes followed by the SNM-encapsulated islets under diffusion (SNM, Diff). The level of glucose-induced insulin secretion from the naked islets cultured under static conditions (Control) was not as significant as the other two groups. (Mean±SEM, n≥3). FIG. 27B shows the stimulation index (SI) was calculated as the ratio of (1) the first insulin collection in the high glucose phase at 40 minutes to the last insulin collection point of the previous low glucose phase at 30 minutes (Immediate Stimulation), and (2) the highest insulin secretion in the high glucose phase to the last insulin collection point of the previous low glucose phase at 30 minutes (Maximum Stimulation). The SI indicates the magnitude of insulin released as stimulated by a higher concentration of glucose. With cytokine exposure (+Ck), the SNM- and SµM-encapsulated islets under diffusion (SNM, Diff & SµM, Diff) and the naked islet culture under static conditions (Control) all showed a significant difference in the magnitude of insulin secreted upon high glucose challenge (Immediate Stimulation). The SNM-encapsulated islets under diffusion (SNM, Diff) and naked islets cultured under static conditions (Control) showed an increase in the magnitude of insulin secretion when the highest insulin secretion in the high glucose phase was used (Maximum Stimulation). (Mean±SEM, n≥3, *p<0.05). FIG. 27C shows the shut-down index (SDI) was the ratio of (1) the first insulin collection point in the subsequent low glucose phase at 70 minutes to the last insulin collection point in the high glucose phase at 60 minutes (Immediate Shutdown), and (2) the lowest insulin secretion in the subsequent low glucose phase to the last insulin collection point in the high glucose phase at 60 minutes (Maximum Shutdown). The SDI reflects the magnitude of cessation in insulin production once glucose concentration returns to normal. With cytokine exposure (+Ck), the SµM-encapsulated islets under diffusion (SµM, Diff) exhibited the highest magnitude of insulin reduction compared to the SNM-encapsulated islets under diffusion (SNM, Diff) and naked islet culture (Control) as glucose dropped low (Immediate Shutdown & Maximum Shutdown). (Mean±SEM, n≥3, *p<0.05).

FIG. 28A-B show in-vitro viability of mouse islets. FIG. 28A shows viability of mouse islets was measured following the 90-minute low-high-low (1.6 mM, 16.6 mM, 1.6 mM) glucose stimulation in which islets were subjected to the mock-loop circuit with (+Ck) or without cytokine exposure for SNM- and SµM-encapsulation under diffusion (SNM, D & SµM, D). The naked islet culture under static culture with cytokine exposure (Control, +Ck) showed significantly less viability compared to all other conditions. (Mean±SEM, n≥3, *p<0.05). FIG. 28B shows viable (green) and dead (red) cells were stained for control static culture without cytokines (A: Control), control static culture with cytokines (B: Control, +Ck), SNM-encapsulated mouse islets under diffusion without cytokines (C: SNM, D), SNM-encapsulated mouse islets under diffusion with cytokines (D: SNM, D, +Ck), SµM-encapsulated mouse islets under diffusion without cytokines (E: SµM, D), and SµM-encapsulated mouse islets under diffusion with cytokines (F: SµM, D, +Ck). Experiments with cytokine exposure (indicated by +Ck) consisted of media containing TNF-α, IFN-γ, and IL-1β. The control static culture with cytokines (B: Control, +Ck) showed significant level of islet damage compared to all other conditions.

FIG. 29 shows the rate of change in insulin secretion as depicted in the table. The rate of change in insulin production was calculated based on the slopes of curves that were fitted on glucose-insulin kinetics graphs to describe the quickness of insulin being secreted as glucose concentration changes. The SµM-encapsulated mouse islets under diffusion without cytokine exposure (SµM, Diff) showed similar rate of insulin secretion in glucose-induced stimulation and a slightly faster insulin cessation compared with the SµM-encapsulated mouse islets under diffusion with cytokine exposure (SµM, Diff, +Ck).

FIG. 30A-B shows SEM images of the pore-containing regions surrounded by solid silicon regions. FIG. 30A shows a top view SEM image illustrating the rectangular pore-containing regions surrounded by solid silicon regions, which provide mechanical support. FIG. 30B shows a further magnified top view SEM image of the pore region showing individual 10 nm-wide pores.

Example 3

Diffusion-based bioartificial pancreas (BAP) devices are limited by poor islet viability and functionality due to inadequate mass transfer resulting in islet hypoxia and delayed glucose-insulin kinetics. While intravascular ultrafiltration-based BAP devices possess enhanced glucose-insulin kinetics, the polymer membranes used in these devices provide inadequate ultrafiltrate flow rates and result in excessive thrombosis. Here, the silicon nanopore membrane (SNM) exhibits a greater hydraulic permeability and a superior pore size selectivity compared to polymer membranes for use in BAP applications. Specifically, the SNM-based intravascular BAP with ~10 and ~40 nm pore sized membranes support high islet viability (>60%) and functionality (<15 minute insulin response to glucose stimulation) at clinically relevant islet densities (5,700 and 11,400 IE/cm$^2$) under convection in vitro. In vivo studies with ~10 nm pore sized SNM in a porcine model showed high islet viability (>85%) at clinically relevant islet density (5,700 IE/cm$^2$), c-peptide concentration of 144 pM in the outflow ultrafiltrate, and hemocompatibility under convection.

Materials and Methods

Silicon Nanopore Membranes (SNM) Architecture and Fabrication

Silicon nanopore membranes (SNM) have been prototyped from silicon substrates by MEMS technology as previously reported[26]. Briefly, the process used the growth of a thin SiO$_2$ (oxide) layer on 400 µm-thick double side polished (DSP) silicon wafers followed by a low pressure chemical vapor deposition (LPCVD) of polysilicon (~500 nm). The wafers were then specifically patterned, dry oxidized, wet etched, deposited with a second polysilicon layer, and finally blanket-etched until 400 nm of polysilicon remained and the underlying vertical oxide layer was exposed. The vertical sacrificial oxide layer defined the critical nanoscale pore size of the membranes. The low temperature oxide (LTO) (~1 µm) was deposited onto polysilicon of the wafers to serve as the hard mask for membrane protection. Deep reactive ion etching (DRIE) removed the backside of each window until membranes were disclosed. Eventually, the sacrificial oxide was etched away in 49% hydrofluoric acid (HF) during the final step of the fabrication process to leave behind open nanoscale slit pores. The wafers were subsequently cut into 1×1 cm chips with an effective area of 6×6 mm$^2$ containing 1500 windows each, with a total of 10$^6$ pores per membrane. Each rectangular pore was 300 nm in depth and 2 µm in length. The SNM with an average pore size width of ~10 nm and ~40 nm were used in this study. All membranes were cleaned using a conventional "piranha" clean procedure, which involved a 20 min-immersion in 3:1 sulfuric acid (H$_2$SO$_4$)/hydrogen peroxide (H$_2$O$_2$) mixture, followed by thorough rinses in deionized (DI) water. Images of SNM were obtained using scanning electron microscope (SEM) (Leo 1550) (FIGS. 1A, 30A, and 30B).

Surface Modification of SNM with Poly(ethylene glycol) (PEG)

SNM were covalently modified with PEG using a previously reported protocol to prevent protein fouling on the membrane surface[26]. The technique used for PEG attachment involved a single reaction step which covalently couples silicon surface silanol group (Si—OH) to a chain of PEG polymer through a trimethoxysilane group forming a Si—O—Si-PEG sequence. Briefly, SNM were immersed in a solution of 3 mM 2-[methoxy(polyethyleneoxy)propyl] trimethoxysilane (PEG-silane) (Gelest: SIM6492.7) in toluene for 2 hr at 70° C. A series of extensive washing steps involving toluene, ethanol, and DI water was used to remove unbounded PEG residue.

Hydraulic Permeability for SNM Pore Size Characterization

An automated mass and pressure measurement system was utilized for characterizing liquid flow through the SNM under a tangential-flow filtration operation. The pore size of the SNM can be related to filtration flow parameters using $$h = \sqrt[3]{\frac{12\mu l Q}{nw\Delta P}}, \qquad (\text{Eq. 1})$$

where h is pore width, µ is the viscosity, l is the membrane thickness, Q is the volumetric flow rate, n is the number of pores per membrane, w is the pore length, and ΔP is the transmembrane pressure. To assemble the overall system for SNM pore size characterization, air was applied through a syringe pump (Sigma: Z675709) into a water reservoir. Water was circulated by a peristaltic pump (Masterflex: 07551-00) through a differential pressure transducer (Omega: PX429 015GI), a flow cell with enclosed membrane, and returned to the original water reservoir. The flow cell was assembled with the SNM submerged under water to remove air bubbles from all compartments. Specifically, a membrane was positioned with the polysilicon interface facing down with a customized silicone gasket positioned on top of the membrane, followed by the final placement of a filtrate chamber on top of the gasket. All sections were fastened together and secured to the base with hand-tightened hex bolts until the gasket was visibly compressed. The ultrafiltrate permeated through the membrane and was routed to a liquid collection container that rested on a precision mass balance (Mettler Toledo: XS205). Measurements from the differential pressure transducer and the mass balance were automatically collected with a data acquisition laptop. A typical membrane hydraulic permeability test consisted of 5 ml/min flow rate and 4 pressure cycles (5, 1, 5, and 1 psi) for durations of 150 s each. Using the specifications for pore length, membrane thickness, and total number of pores provided based on individual wafer designs, the average pore size of SNM was calculated using Equation 1. All SNM membranes in this study were surface-modified with PEG and exhibited an average pore size of ~10 nm and ~40 nm.

Development of the Islet Chamber (IC)

Figure 31:
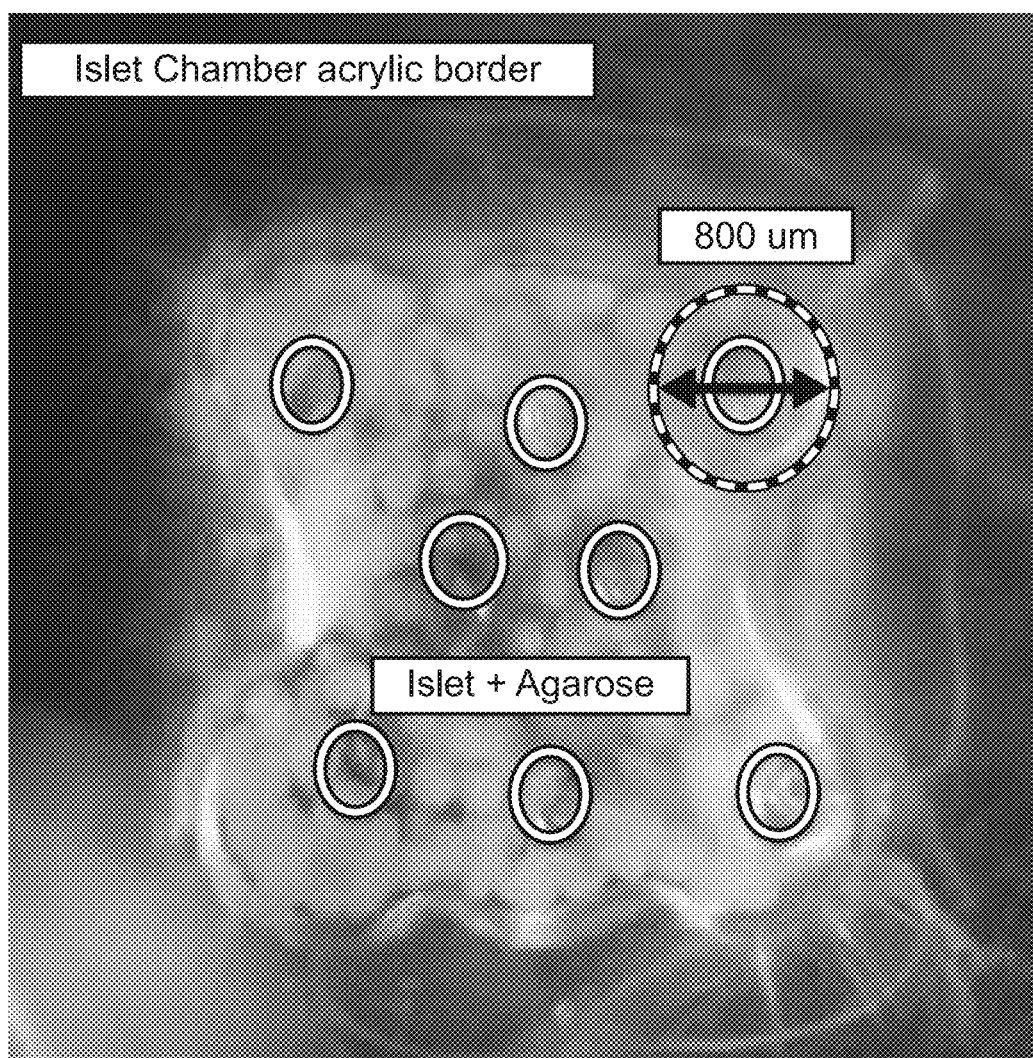
FIG. 31 shows a gross image of islets and agarose mixture inside the IC in which the maximum diameter surrounding each ultrafiltrate channel is 800 μm.

In this study, IC possessed a thickness of 1000 µm and high islet densities of 10% (5,700 IE/cm$^2$) and 20% (11,400 IE/cm$^2$). Islet density by percentage was calculated as the ratio of total islet volume expressed in islet equivalents and the IC volume. Islet density by surface area was calculated by dividing the total number of islet equivalents (IE) by the device membrane surface area. A biocompatible acrylic sheet (McMaster: 8589K11) was first laser-cut to create ~2.4 mm×~2.4 mm×~1 mm thick void region which was inserted with eight 100 μm diameter polytetrafluoroethylene (PTFE) coated wires (McMaster: 1749T11). A 2% agarose-islet mixture was then poured into this void region of acrylic sheets. After the agarose-islet mixture was cured, all wires were removed (FIG. 20D). Using this process, a hexagonal arrangement of eight 800-μm cylindrical agarose-islet regions (dotted red circle) with a central 100 μm cylindrical channel (solid red circles) was obtained for the IC (FIG. 31). This configuration created a diffusion distance ≤400 μm between the islets and ultrafiltrate. After IC construction, it was assembled in the iBAP as described in FIGS. 21-22A with gaskets between the various iBAP components.

Assembly of an Intravascular Bioartificial Pancreas Device (iBAP) for Islet Encapsulation The intravascular bioartificial pancreas device (iBAP) is shown in an exploded view in FIG. 21-22A: the polycarbonate flow path component containing the blood flow path, two SNM sandwiching the islet chamber (IC) containing the agarose (Sigma: A2576)-seeded mouse islets, the polycarbonate backside (PC Backside), and the ultrafiltrate port (Ultrafiltrate Outlet). The parallel-plate blood flow path was modeled with SolidWorks and computational fluid dynamics (CFD) to create ideal flow characteristics to minimize thrombosis. The iBAP was symmetrical on both sides and could be assembled with one IC on each side. The iBAP can possess up to 0.72 cm$^2$ of SNM area. In operation, fluid flows through the Flow Path component at an elevated pressure creating a transmembrane pressure (TMP) of ~80 mmHg between the blood flow path and the Ultrafiltrate Outlet resulting in ultrafiltrate flow through the SNM, IC, PC Backside, and Ultrafiltrate Outlet, which was collected in a tube in vitro or drained into interstitial tissue space in vivo. Under the diffusive condition, the PC Backside was capped-off resulting in no ultrafiltrate flow through the system. All device components were individually sterilized either by autoclave or Nolvasan for both in vitro and in vivo experiments.

Testing of the Intravascular Bioartificial Pancreas Device (iBAP) In Vitro

All procedures involving isolation of mouse islets were performed in accordance with protocols approved by the Institutional Animal Care and Use Committee (IACUC) at the University of California, San Francisco (UCSF). Mouse islets were isolated from 8 to 10-week-old male B6 mice (Jackson Laboratories) based on previously described protocols. Harvested islets were maintained in suspension culture with RPMI 1640 with L-glutamine and 11.1 mM glucose (Gibco: 11875-093), 10% fetal bovine serum (FBS) (Gibco: 16000), and 1% penicillin-streptomycin (P/S) (UCSF Cell Culture Facility: CCFGK003). A 2% agarose gel mixed with appropriate amount of mouse islets was dispensed into the previously described IC to create high islet densities of 10% or 20% by volume, respectively. The SNM with ~10 nm and ~40 nm pore sizes were chosen to encapsulate the IC with 10% and 20% islet density. For in vitro viability tests, a mock-loop circuit was set up with a peristaltic pump flowing culture medium through the iBAP at TMP of ~80 mmHg to generate ultrafiltrate for convective condition (FIG. 22A), whereas no ultrafiltrate was produced for the diffusive condition. The viability experiments studied both ~10 nm and ~40 nm SNM encapsulating both 10% and 20% islet densities. After 3 days of culture, the devices were disassembled and the islets were assessed for viability. Using this same mock-loop circuit, glucose-insulin kinetics was explored in iBAPs containing either 10% or 20% islet density and either ~10 nm or ~40 nm pore sized SNM. SNM-encapsulated mouse islets in the iBAP were exposed to a low, high, and low glucose (Gibco: 11879) challenge on day 0. Ultrafiltrate directly produced from the IC under convection was collected for insulin measurements. Insulin content was analyzed with mouse insulin enzyme-linked immunosorbent assay (ELISA) kits (Mercodia: 10-1247-01) with accounted dilutions.

Implantation of the Intravascular Bioartificial Pancreas Device (iBAP) in Pigs

A preliminary proof-of-concept study was designed with a swine model because of the comparably sized vasculature and hematologic similarities with humans. The study was approved by the IACUC review committee at PMI Preclinical CRO, San Carlos, Calif.

For pig #1, the device was assembled as previously described with each chamber containing a 5% islet equivalents (IE) density by volume of mouse islets suspended in agarose gel. Oral aspirin (81 mg) and clopidogrel (75 mg) were given to a 75 kg female Yorkshire pig for 3 days preoperatively and then daily thereafter. After general anesthesia was induced, a vertical incision was made to the left of midline to expose the left external jugular vein. A 15 Fr double-lumen tunneled catheter (NextStep®, Teleflex, Morrisville, N.C.) was placed in the left external jugular vein for blood sampling. The right carotid artery and right external jugular vein were then exposed via a similar vertical incision on the right side of the neck. Once the vessels were exposed a subcutaneous pocket was created caudally for eventual device placement. Heparin was given intraoperatively targeting an activated clotting time (ACT) of greater than 200 seconds. The 6 mm externally-supported polytetrafluoroethylene (PTFE) grafts were then anastomosed end-to-side to the internal carotid artery for inflow and the external jugular vein for outflow. The device was then placed in the subcutaneous pocket and anchored to surrounding soft tissue. The inflow and outflow grafts were then connected to the device and clamps were removed to allow blood flow through the device, which was visually confirmed (FIG. 34A-D). The overlying soft tissue and skin were then closed in layers and then animal was extubated and allowed to recover. Meloxicam and buprenorphine were administered as needed for post-operative pain.

Figure 35A:
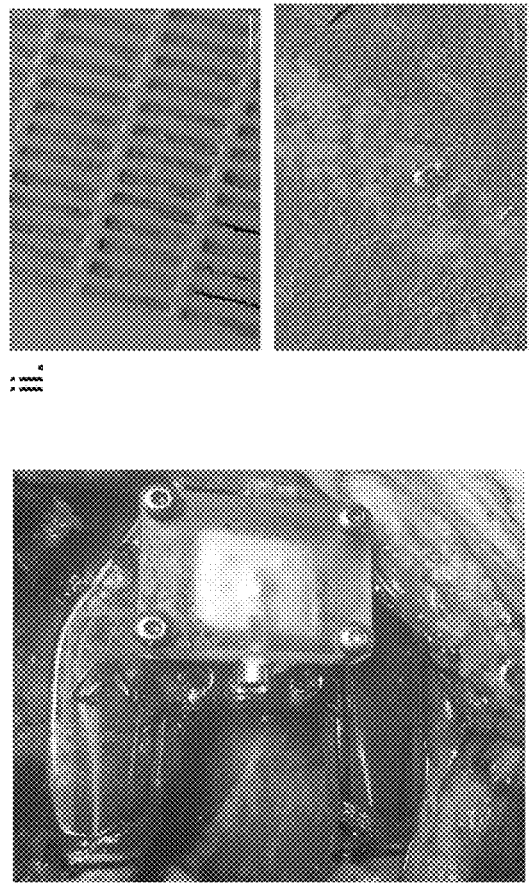
FIGS. 35A-35D shows in vivo testing of the intravascular bioartificial pancreas device (iBAP) with 10% islet density encapsulated with 10 nm-pore size SNM under either diffusion or convection for 3 days.

For pig #2, the device was assembled as previously described with 10% density by volume for each chamber. One chamber had a channel in communication with the islets that was open to atmosphere, allowing for ultrafiltrate flow through the chamber (FIG. 22A). The ultrafiltrate then passed through the channel and was freely deposited into the surrounding tissue and subcutaneous pocket (FIG. 35A). The other chamber's ultrafiltrate outlet was capped resulting in a diffusive chamber. The technical aspects of the implant procedure were identical to Pig #1. Blood flow through the device and ultrafiltrate deposition into the surrounding tissue was visually confirmed prior to closure of the incision.

Assessment of Islet Function In Vivo

Islet function was assessed using standard intravenous glucose tolerance tests (IVGTT) with administration of glucose (0.5 g/kg in 40% solution) via the tunneled venous catheter. Blood was drawn to measure serum glucose using a standard glucometer (Accu-Chek Compact Plus: 1002-5021) at time 0, 5, 10, 15, 30, 60 and 90 minutes. The IVGTT was administered on post-operative day (POD) 1 and 2 prior to the animals eating their morning meals. On POD 3 the test was performed intra-operatively prior to planned explant of the device and islet retrieval. For pig #1, blood sampling for the intra-operative IVGTT was performed via direct cannulation of the external jugular venous outflow tract immediately distal to the anastomosis. All samples from systematic circulation and directly collected from ultrafiltration port were stored on ice prior to testing for mouse insulin enzyme-linked immunosorbent assay (ELISA) (Mercodia: 10-1247-01) and c-peptide ELISA kits (EMD Millipore: EZRMCP2-21K).

Patency Assessment and Device Explant with Islet Retrieval

Figure 34A:
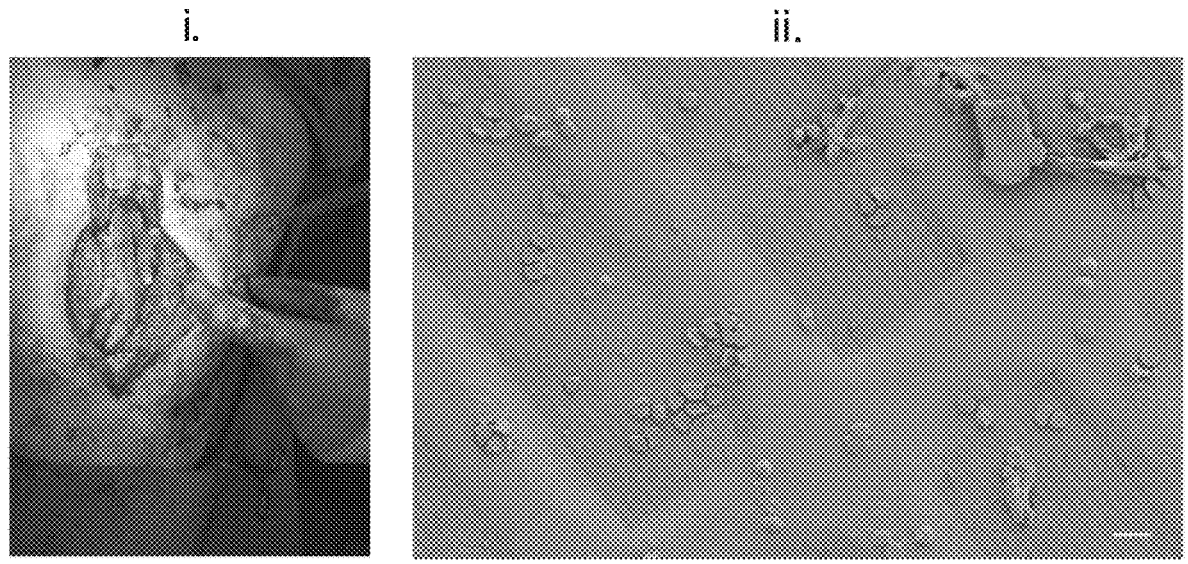

On POD 3 both animals were taken back to the operating room for assessment of patency and device retrieval. Once the animal was intubated and sedated the incision was re-opened and the device was delivered into the superficial tissue for visual assessment and confirmation of maintained patency. A final IVGTT was administered. As mentioned, for pig #1, blood was sampled directly from the outflow vein via direct cannulation of the external jugular vein distal to the anastomosis. For pig #2, blood was sampled from the tunneled catheter. Once the IVGTT was completed, the carotid was cannulated proximal to the anastomosis with a 5 Fr catheter. Radiopaque contrast media was then injected (Visipaque™, GE Healthcare, Little Chalfont, United Kingdom) to fluoroscopically confirm flow through the device (FIGS. 34A & 35A). The inflow and outflow grafts were then clamped and the device was then explanted and subsequently flushed with culture media prior to disassembly and retrieval of the islets from the chamber.

Islet Viability

Islet viability was assessed by double staining with the Live/Dead Cell Imaging Kit (488/570) (Life Technology: R37601). Live cells are distinguished by the presence of intensely fluorescent calcein (green) which is well-retained within live cells, whereas dead cells are stained with red. Briefly, agarose-encapsulated mouse islets were incubated in the mixture of live (green) and dead (red) kit components for 15 min and extensively washed in phosphate buffered saline (PBS) to remove excess staining. Images of mouse islets were obtained using laser scanning Nikon Spectral C1si confocal microscope (Nikon Instruments). The percentage of viability was calculated based on the ratio of non-dead or the green area over the entire area of that islet.

Explanted Membrane Analysis

For observation, SNM were fixed in a solution containing 3% glutaraldehyde (Sigma: G7651), 1 M sodium cacodylate (Polysciences) and 0.1 M sucrose (Sigma). After 2 days, the substrates were washed with distilled water. Dehydration was achieved by placing these scaffolds in an increasing concentration of ethanol (50-100%). Dehydrated samples were then mounted on aluminum stubs, sputter-coated with gold-palladium, and examined with scanning electron microscopy (SEM) (Ultra 55, Carl Zeiss).

Blood Platelet Adhesion and Activation

The SNM were fixed with 4% paraformaldehyde followed by PBS washes and incubated in blocking solution (PBS, 1% bovine serum albumin (BSA)) for 30 min. Samples were then incubated with CD41 antibody (Biorbyt: orb181793) for platelet adhesion (green) and CD62p antibody (Bioss: bs-0561R-Cy3) for platelet activation (red) at a dilution of 1:300 for 4 h and repeatedly washed with PBS to remove residues. Images were obtained using 6D High Throughput Perfect Focus System (Nikon Instruments).

Statistical Analysis

Sample pairs were analyzed using Student's t-test. Multiple samples were evaluated with one-way or two-way analysis of variance (ANOVA) followed by Bonferroni and multiple comparison using Graphpad Prism software (San Diego, Calif.). A p value of <0.05 was accepted as statistically significant for all analyses.

Results iBAP Testing In Vitro

The iBAP comprising a ~10 nm pore sized SNM with 10% (5,700 IE/cm$^2$) or 20% (11,400 IE/cm$^2$) mouse islet densities was investigated for glucose-stimulated insulin response and viability of the encapsulated islets after three days. Under convection, the iBAP with 10% mouse islet density and ~10 nm pore sized SNM showed an increase in insulin secretion within 10 minutes of high glucose exposure (FIG. 32A (i)), which was consistent with normal islet function of biphasic insulin release (i.e. the first insulin phase appeared within 5-10 minutes followed by a second sustained phase that is slower and delayed as times goes longer). Furthermore, during the period of 63 to 78 minutes in which the glucose concentration decreased, the corresponding stimulated-insulin secretion also dropped. However, when the cell density increased from 10% to 20% in the iBAP with ~10 nm pore sized SNM under convection, no significant change in glucose-stimulated insulin level was observed within the first few minutes of high glucose exposure (FIG. 32A (ii)). The stimulation index (SI), the ratio of stimulated to basal insulin secretion normalized by the insulin content, was calculated as 4.4±0.6 and 1.1±0.1 for the iBAP of ~10 nm pore sized SNM with 10% and 20% mouse islet densities, respectively. It is well-recognized that delay of insulin secretion in response to glucose (>15 min) has been a common problem encountered in the early extravascular hollow-fiber systems. Our iBAP with ~10 nm pore size under convection supported the normal insulin function at 10% islet density with no significant delay in glucose-stimulated insulin response. However, the glucose stimulated-insulin response at 20% islet density under convection with ~10 nm pore sized SNM showed abnormal insulin-functioning behavior, indicating that encased cells were likely not in optimal health in that environment.

Figure 32B:
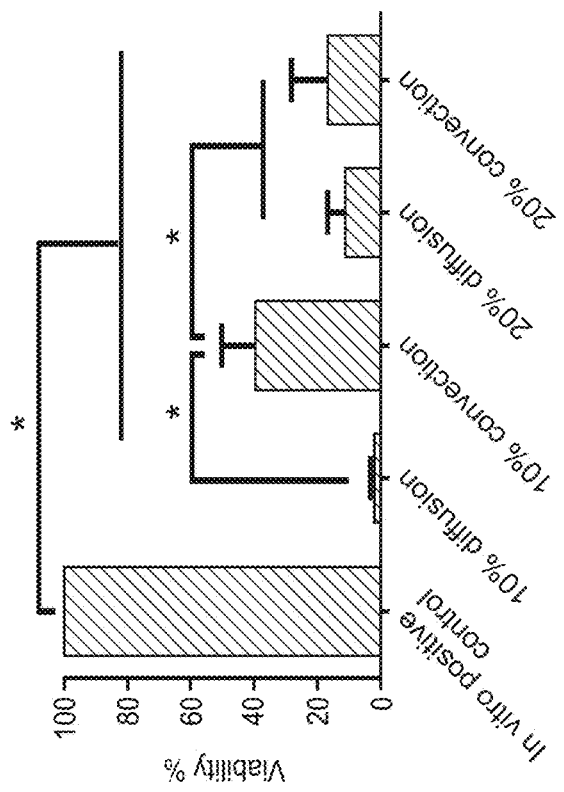
Figure 32C:
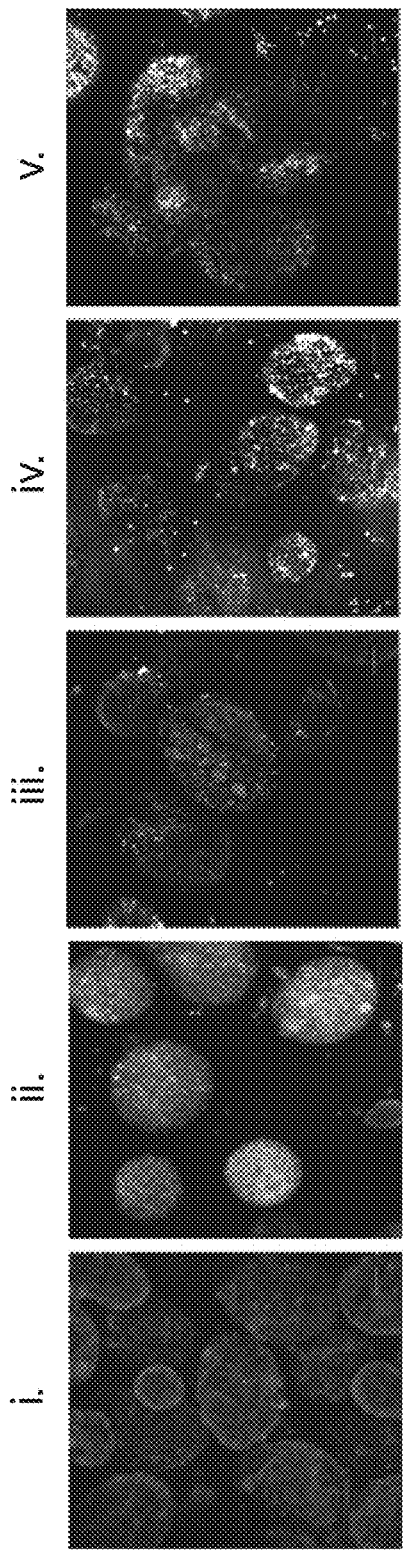

The viability study of ~10 nm pore sized SNM in the iBAP demonstrated that 10% mouse islet density under convection (40±11%) showed a higher viability compared to that under diffusion (4.0±1.3%) (FIG. 32B-C). Furthermore, as the islet density increased to 20% within the islet chamber, the viability significantly decreased under diffusion (11±5.8%) and convection (17±11%) (FIG. 32B-C). In summary, the ~10 nm pore sized SNM under convection is sufficient to support the viability and glucose-insulin response of 10% (but not 20%) mouse islet density.

Figure 33B:
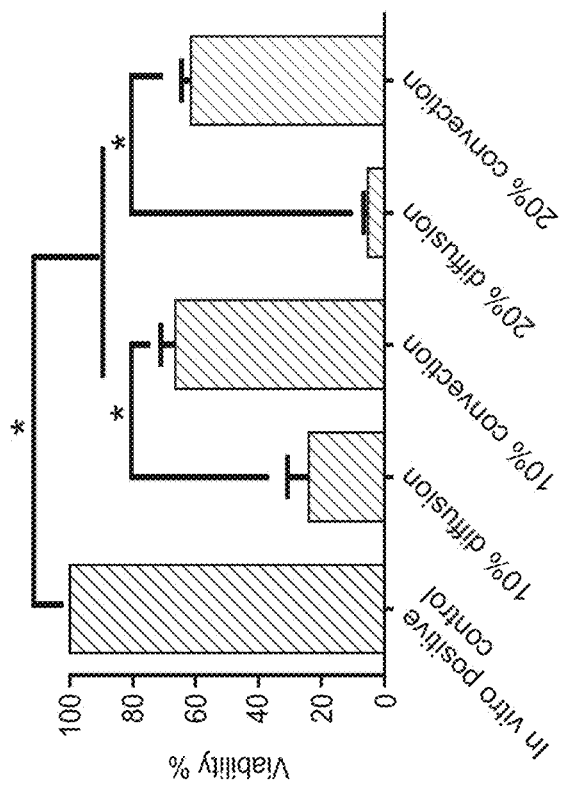
Figure 33C:
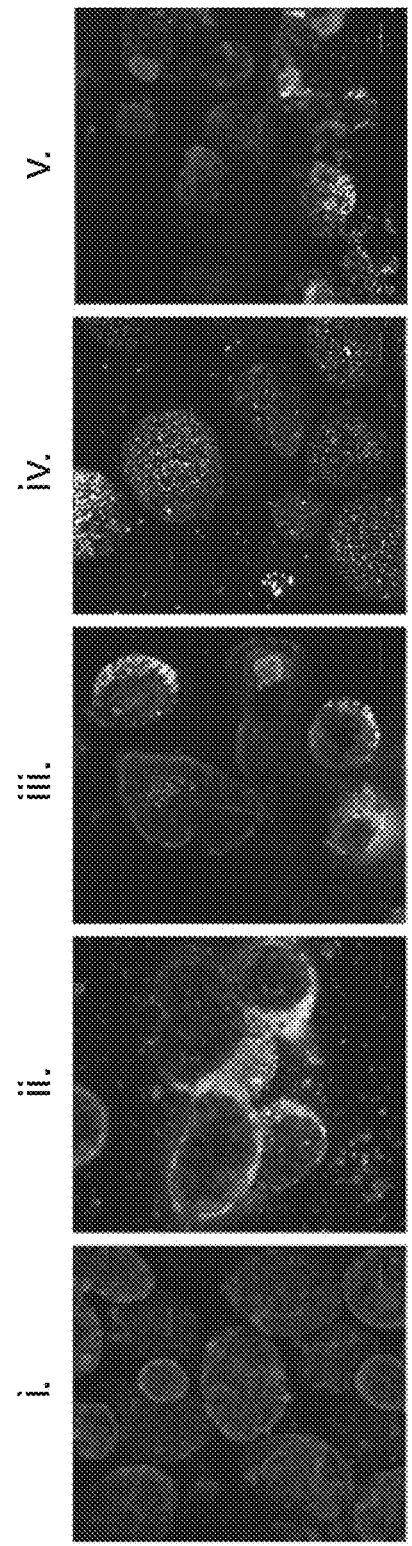

To verify whether the pore size was the limiting factor in causing cell death at the higher density, the ~40 nm pore sized SNM with 10% or 20% mouse islet densities was studied in the iBAP under diffusion and convection. The glucose-stimulated insulin study showed that both 10% (FIG. 33A (i)) and 20% (FIG. 33A (ii)) demonstrated the characteristic insulin biphasic release curves. The iBAP at 10% and 20% mouse islet densities with ~40 nm pore sized SNM indicated that the first spike in glucose-stimulated insulin production occurred within 10 minutes of high glucose exposure. Both conditions showed insulin shut down as glucose concentration decreased. The SI at 10% and 20% mouse islet densities with ~40 nm pore sized SNM were 3.2±1.3 and 9.1±1.2, respectively. Although the absolute amount of insulin secreted did not double when cell density increased from 10% to 20%, the latter showed a 1.9-fold increase in SI factor, indicating the magnitude of insulin stimulated from basal to high glucose level almost doubled. The viability study demonstrated that 10% mouse islet density under convection (66±4.8%) showed a higher viability compared to that under diffusion (24±6.8%) (FIG. 33B-C). Furthermore, as the islet density increased to 20% within the islet chamber, the viability of islets under convection (61±3.0%) exhibited a significant increase in viability compared with that under diffusion (5.2±1.3%) (FIG. 33B-C). Overall, the iBAP using ~40 nm pore sized SNM under convection supported the viability and glucose-insulin response at both 10% and 20% mouse islet densities.

Compared to the previous in vitro experiments using ~10 nm pore sized SNM, the ~40 nm pore sized SNM enhanced the viability at 10% and 20% mouse islet densities to 66±4.8% and 61±3.0% as compared to 40±11% and 17±11% for the ~10 nm pore sized SNM under convection, respectively (FIGS. 32D and 33B). Islet viability correlates positively with an increase in pore size dimension under convection. The greater amount of ultrafiltrate produced by ~40 nm pore size under convection enhanced the viability and functionality of encapsulated islets. In contrast, diffusion provides inadequate mass transfer to support a greater islet density. Although an increase in pore size improved islet viability at a lower cell density (10%) under diffusion from ~10 nm (4.0±1.3%) to ~40 nm pore size (24±6.8%), the islet viability at a higher cell density (20%) showed no significant difference under diffusion ((11±5.8%) vs. (5.2±1.3%)). These data show that nutrients and oxygen remained severely depleted under diffusion even when the pore size was increased to ~40 nm. Diffusive mass transport has been widely reported for porous materials with nanometer-sized pores, as one study showed that the diffusion of 45 nm nanoparticles was slowed down by a factor of 2 in 300 nm cylindrical pores due to hydrodynamic friction. Therefore, given the greater cell density, the large diffusion distance, and the restriction of nanoscaled pores under diffusion, insufficient transfer of nutrients and oxygen would likely result in cell necrosis and hypoxia. In summary, our in vitro testing of the iBAP demonstrated that convection is the key to supporting 10% or 20% mouse islet density with either ~10 nm or ~40 nm pore sized SNM with higher islet viability and providing appropriate glucose-stimulated insulin response.

iBAP Implantation in Pigs

Figure 34B:
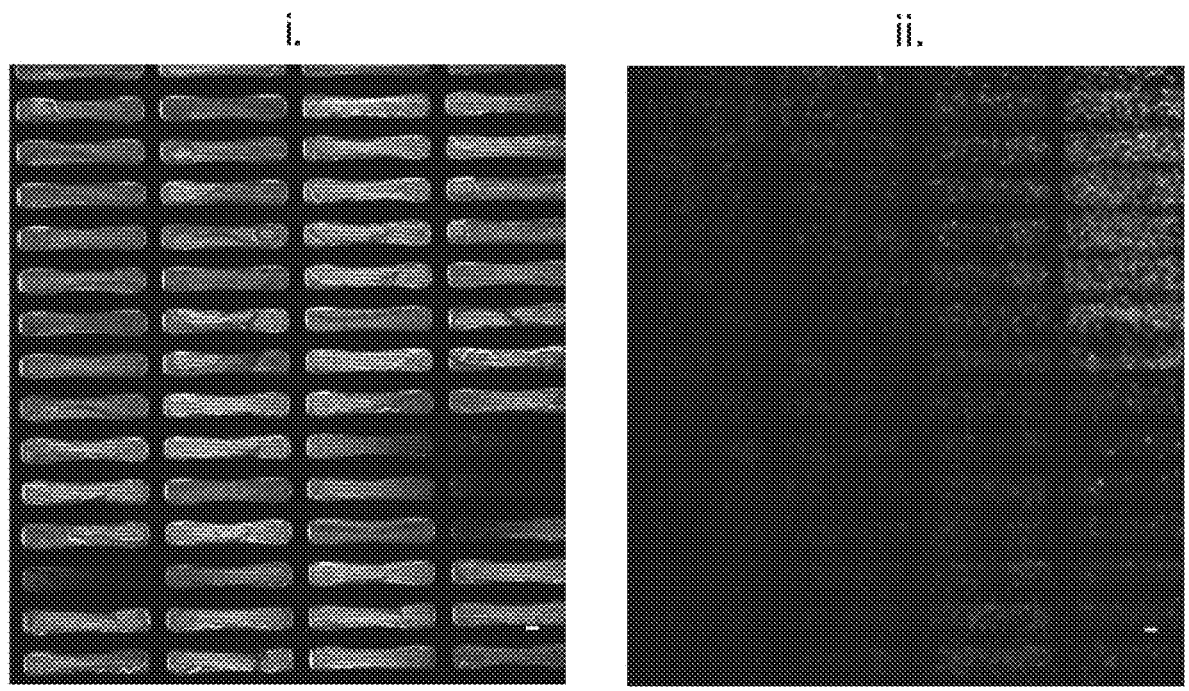
Figure 37:
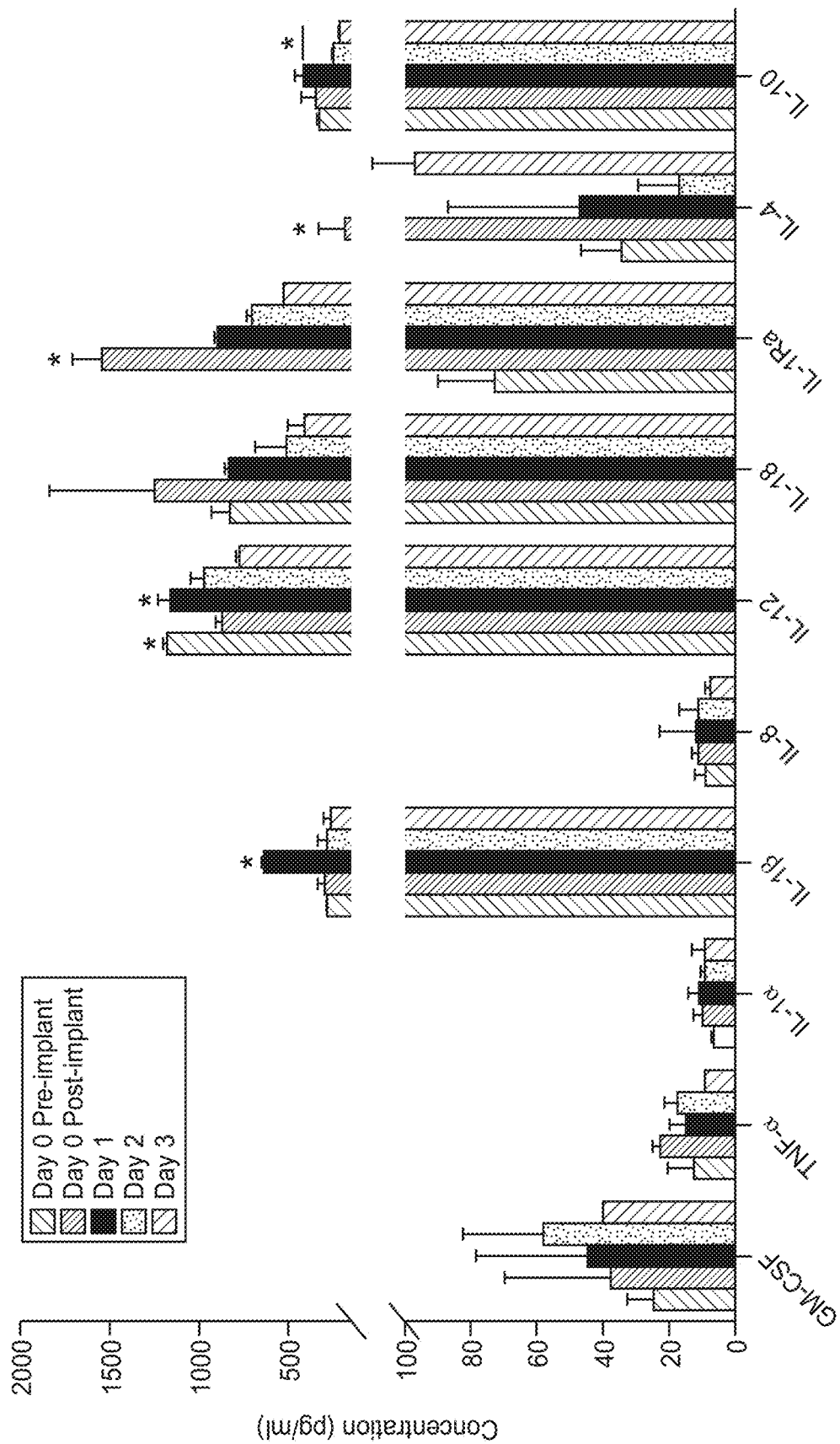
FIG. 37 shows daily measurement of the systematic cytokine concentration in the pig.

As a first step to study the device and membrane patency, the diffusion-based iBAP with ~10 nm pore sized SNM and a 5% mouse islet density (2,850 IE/cm$^2$) was intravascularly grafted in the porcine model for three days. The angiogram showed no thrombosis formation and obstruction in the blood flow path of the device during explant (FIG. 34A (i)). This data matched with previous studies in which the iBAP device was intravascularly implanted into Class A dogs where the device was patent throughout the experiment, possessed no thrombus formation, and generated 27.5 ml of ultrafiltrate based on a SNM pore size of 5.6 nm after explanted at 8 days. A cytokine panel indicated an expected increase in the pro-inflammatory response from pig immediately after the surgery (FIG. 37). SEM images of blood-contacting SNM displayed some non-catastrophic attachment and aggregations of cells and adhesive proteins (FIG. 34A (ii)). In particular, red blood cells, white blood cells, and platelets were deposited on the membrane surface. Subsequent immunohistochemical analysis showed that while platelet adhesion mostly in the porous regions of SNM (which contain the nanopores) as indicated by the green CD41 marker, there was minimal platelet activation observed as stained by the red CD62p marker (FIG. 34B). The viability study demonstrated that the diffusion-based iBAP in the pig supported the viability at 5% mouse islet density with ~10 nm pore size (88±4.9%) which was comparable with the in vitro conditions (89±2.1%) (FIG. 34C). To avoid hypoxia and necrosis of cells located at the center of diffusion-based devices, islet density of the macrocapsules has been suggested to be 5-10% of the volume fraction in order to ensure the proper exchange of nutrients and waste of islets. Our iBAP with ~10 nm pore sized SNM demonstrated sufficient mass transfer to support the viability of 5% islet density under diffusion (FIG. 34D). Unfortunately, the concentration of mouse insulin and c-peptide in porcine systemic circulation was below the detection limit.

Figure 35B:
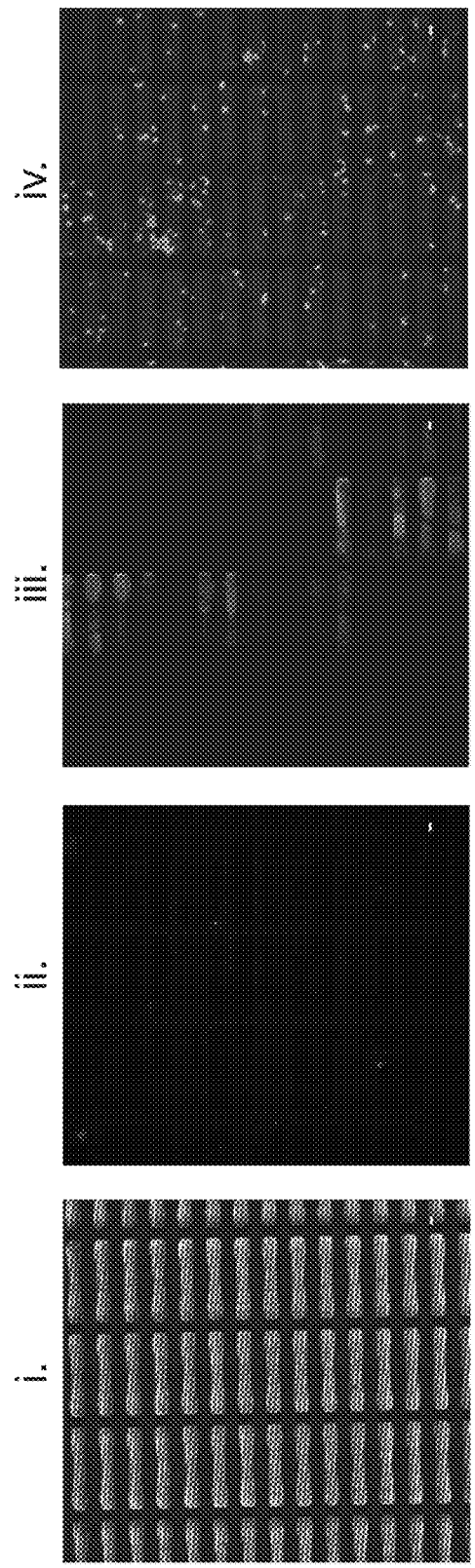
Figure 35C:
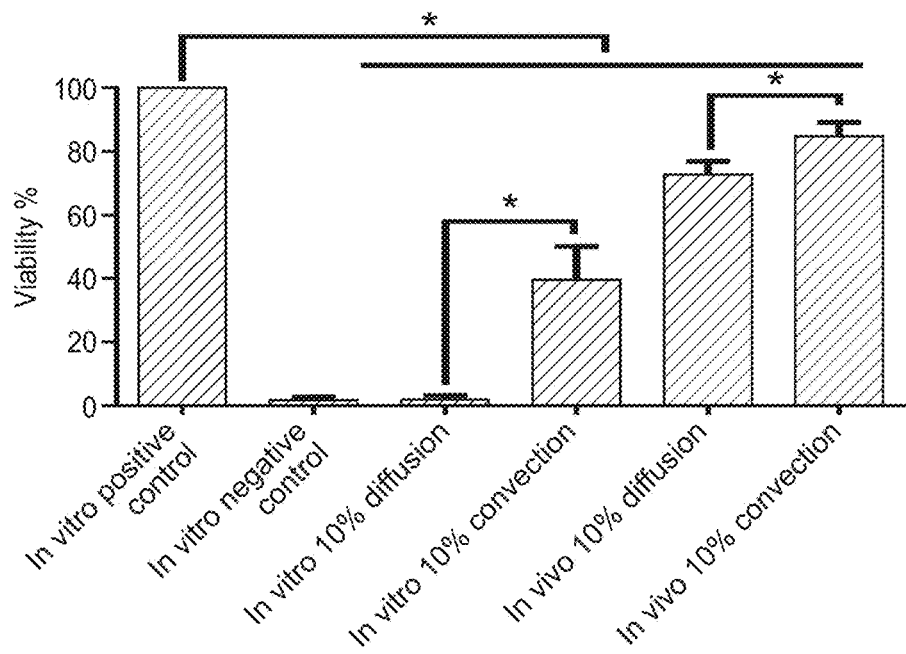
Figure 35D:
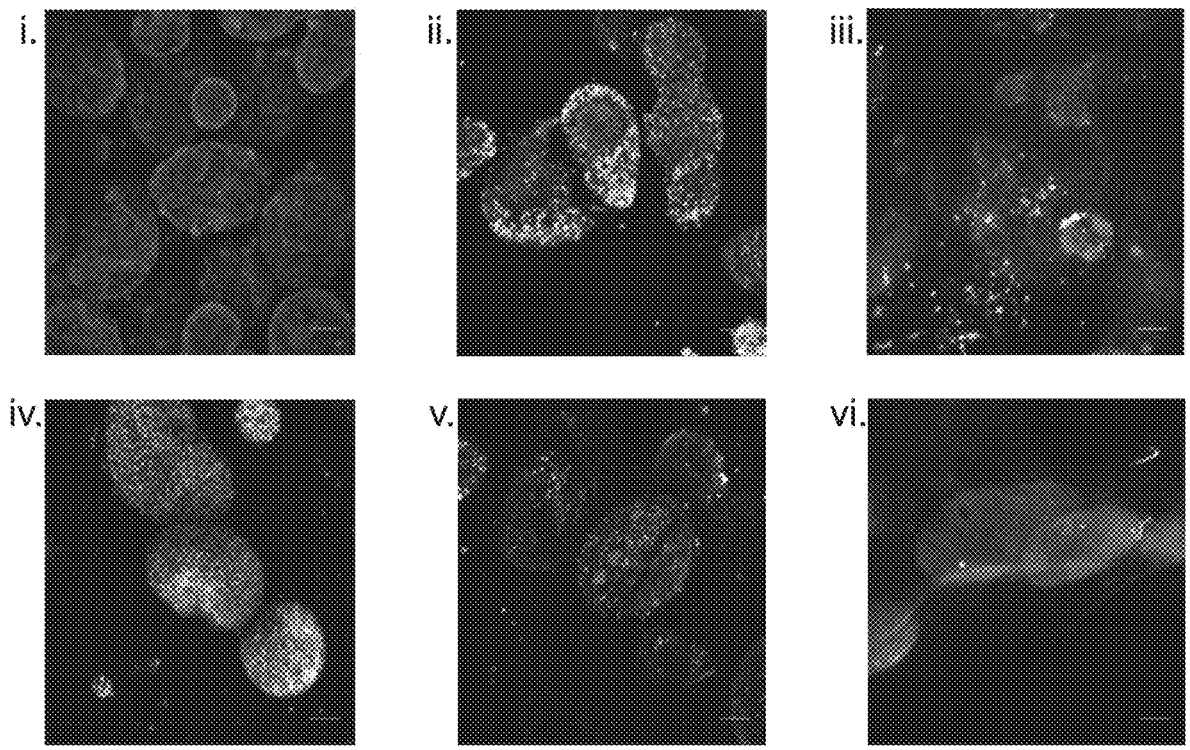
Figure 38:
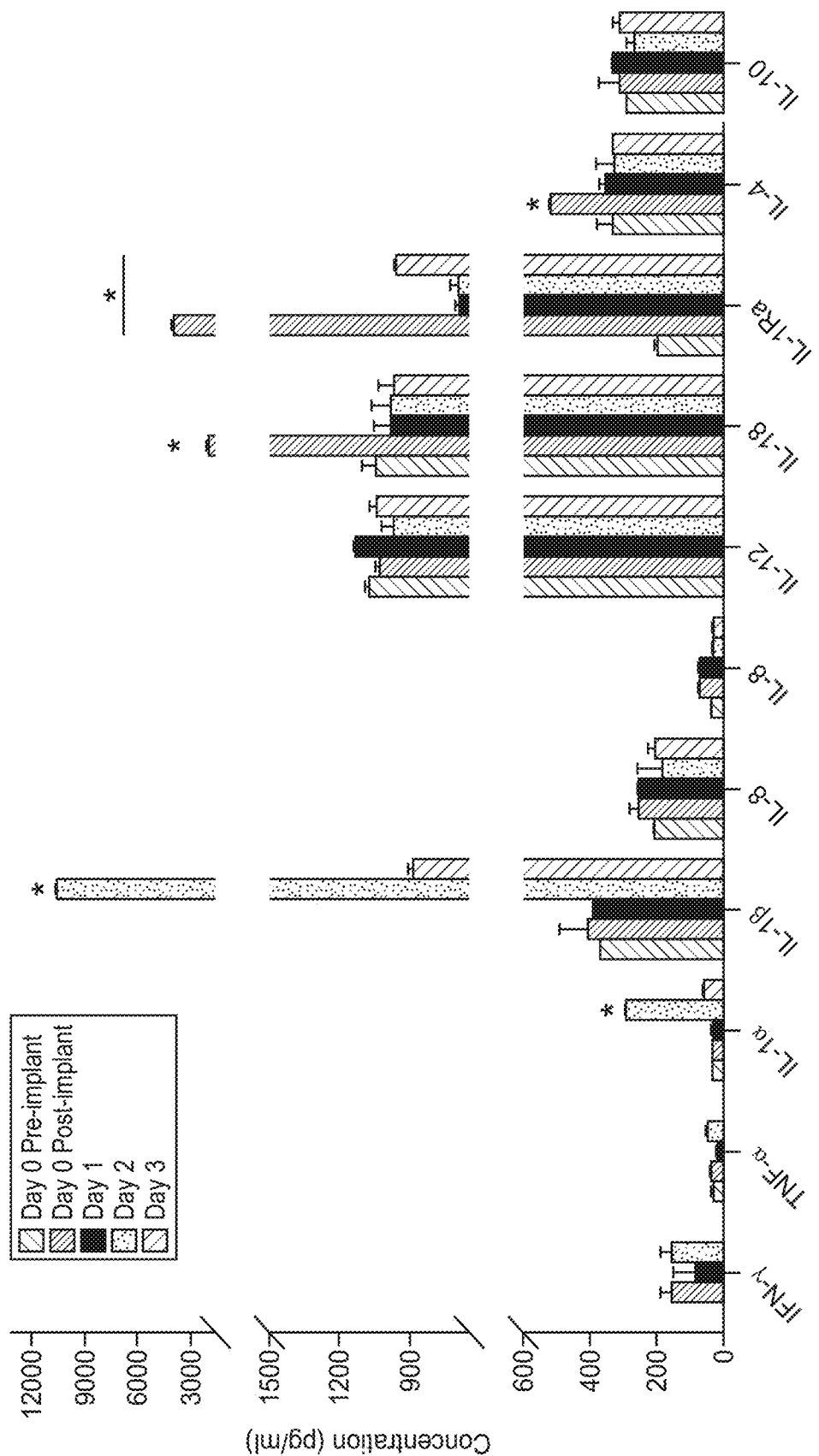
FIG. 38 shows daily measurement of the systematic cytokine concentration in the pig.

Next, the performance of the iBAP with SNM-encapsulated mouse islets under diffusion and convection at a higher islet density was evaluated to demonstrate the effectiveness of convective mass transfer for supporting islet viability and functionality. Specifically, the iBAP with ~10 nm pore size SNM and a 10% mouse islet density (5,700 IE/cm$^2$) with convective and diffusive mechanism was grafted to the carotid artery and vein of a pig for three days. A pro-inflammatory response was also observed for this pig immediately after the surgery (FIG. 38). No ultrafiltration was generated for the diffusive side, whereas ultrafiltrate production was observed on the convective side. The ultrafiltrate was directly drained into the interstitial space of the animal After three days, no significant change in device blood flow rate and the ultrafiltrate appeared to be clear, indicating the membranes were intact during the in vivo experiment (FIG. 35A (i)). The angiogram also showed no thrombus formation and obstruction in the blood flow path of the device during explant. Gross inspection of the blood-contacting membrane surfaces showed minimal cellular adhesion for both diffusive and convective conditions; however, the back side of the SNM under convection exhibited a white layer of proteinaceous materials (FIG. 35B (iii)). Our previous study showed that a pore size of ~7 nm SNM can prevent the passage of large molecules such as bovine serum albumin (66.5 kDa). SEM images of blood-contacting SNM displayed minimal cellular attachment for the diffusive case, whereas there appeared to be more cellular deposition were present for the convective condition (FIG. 35A (ii)). Subsequent immunohistochemical analysis showed that the convection resulted in more platelet adhesion and activation on the blood-exposed SNM surface compared with diffusion (FIG. 35B). More importantly, the viability of 10% mouse islet density with ~10 nm pore size was higher in the convective condition (85±4.4%) compared to the diffusive scenario (73±4.1%). Interestingly, the in vivo viability at 10% mouse islet density with ~10 nm pore size under diffusion (73±4.1%) was greater than the in vitro viability of those under diffusion (2.0±1.3%) and convection (40±11%). The ultrafiltrate generated directly from the islet chamber on the convective side indicated a mouse c-peptide concentration of 144 pM (or 12 pg/min/IE (islet equivalent) insulin production rate), exhibiting the functionality of the encapsulated islets. These data demonstrate that SNM encapsulation under convection preserved islet viability and functionality of the encapsulated cells at a cell density for macroencapsulation. To summarize, the in vitro testing of the iBAP demonstrated that SNM with ~10 nm pore size showed an improved viability at 10% mouse islet density (5,700 IE/cm$^2$) under convection, and SNM with ~40 nm pore size demonstrated an increase in viability at 10% (5,700 IE/cm$^2$) and 20% (11,400 IE/cm$^2$) mouse islet densities compared to those tested under diffusion. Furthermore, the glucose-insulin kinetics experiments showed physiological glucose-insulin response and a clinically relevant absolute insulin production rate. Furthermore, porcine studies demonstrated both device and membrane patency under convection and diffusion, a higher islet viability at 10% mouse islet density with convection, and a clinically relevant mouse insulin production rate on a per IE basis. Overall, these studies show the feasibility of designing a full-scale SNM-based iBAP to achieve long-term blood flow patency, improved islet viability with convection in comparison to diffusion at clinically relevant densities, and sustained clinically relevant insulin secretion on a per IE basis.

Example 4

The silicon nanopore membrane possesses ultra-high-hydraulic permeability. A range of different pore-size SNM (5-500 nm) has been tested to generate the appropriate ultrafiltrate rates to deliver the necessary convective mass transfer of nutrients and insulin, while still maintaining immunoisolation. FIG. 39 presents hydraulic permeability data for various pore-size SNM and FIG. 30A-B present scanning electron microscopy (SEM) images of 10 nm-wide SNM.

The silicon nanopore membrane possesses ultra-selective precise slit-shaped nanopores to achieve immunoisolation.

SNM with highly precise pore were fabricated using an innovative process and demonstrated excellent hydraulic permeability. Microelectromechanical systems (MEMS) fabrication technology produced the SNM. A thin sacrificial $SiO_2$ layer is grown defining the submicron pore size of the membrane. Thermal oxidation of silicon substrates provides oxides down to 3 nm in thickness with <1% variation. The oxide is etched leaving behind open parallel-plate nanochannel pores. 0.25-1.00 μm-thick polycrystalline silicon membranes with pore sizes between 5-500 nm supported by a 400 μm-thick support structure were fabricated. The SNM hydraulic permeability was tested in a custom flow cell with cross-flow and a transmembrane (TMP) pressure. Hydraulic permeability experiments demonstrated greater hydraulic permeability of SNM than conventional polymer membranes.

Polymer coated SNM reduced protein adsorption and provided a hemocompatible surface. Polymer coatings were evaluated on silicon substrates to retard protein fouling. Polyethylene glycol (PEG), polysulfobetaine methylacrylate (pSBMA), and poly(N-vinyldextran aldonamide-co-N-vinylhexanamide) (PVAm-Dex/Hex) were chosen to reduce nonspecific protein adsorption. A Rapid In Vivo IntraVascular Evaluation (RIVIVE) protocol inserted PEG-coated and uncoated (bare) silicon darts in femoral veins of Wistar rats. After 30 days of implantation, the darts and vessels were explanted and evaluated by gross examination, histology, and scanning electron microscopy (SEM) (FIG. 40). All uncoated silicon darts had adherent platelet-fibrin clots, while the PEG-coated darts showed no adherent clot.

Figure 41:
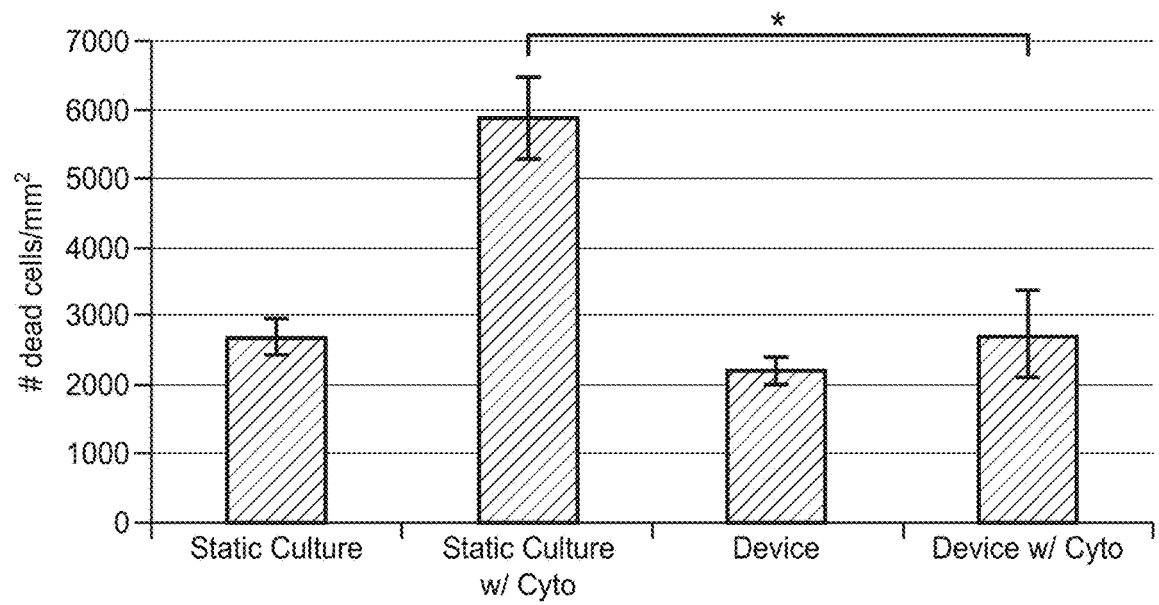
FIG. 41 shows SNM encapsulation of islets provides immunoisolation from cytokines and retains islet viability. IL-1β, TNF-α, and IFN-γ were tested at 50 U/ml, 1000 U/ml and 1000 U/ml respectively.

SNM demonstrated successful immunoisolation. Islet immunoisolation was also studied in vitro using cell culture medium with or without cytokines (IL-1β, TNF-α, and IFN-γ). Islets were encapsulated in between two 7 nm pore SNM. After six hours, the islets were removed and stained for viability. Control static culture experiments were performed to determine the effect of SNM. FIG. 41 indicates the ability of the 7 nm pore SNM to achieve islet immunoisolation. The large size of complement proteins (such as C4, 210 kDa, and C1q, 410 kDa) suggests limited transport through SNM. Complement permeation through SNM was evaluated by a functional hemolytic assay measuring total complement activity as the capacity of serum to lyse sheep red blood cells coated with anti-sheep erythrocyte antibodies. 100% of the total complement activity was detected in the receiving chamber when commercially available membranes (100-400 nm pores) separated the two chambers. In contrast, less than 1% of total complement activity was detected with SNM and track-etch membranes. These results demonstrate SNM block large complement molecules.

A small-scale cell scaffold has been developed and enables testing of enriched insulin producing cells under convection. In order to test ultrafiltrate formation under convective mass transport, a small-scale Cell Scaffold has been developed and tested with islets. The Cell Scaffold consists of a hexagonal arrangement of eight 100 μm diameter cylindrical ultrafiltrate channels (solid circles in FIG. 31) molded into a 2% agarose gel by eight 100 μm diameter PTFE coated wires to minimize the diffusion distance between the cells and ultrafiltrate. Biocompatible acrylic sheets were laser cut to create ~2.4 mm×~2.4 mm×~1 mm thick void region holding the cells, agarose, and ultrafiltrate channels in between SNM. FIGS. 20A-D illustrate the processes and fixtures for creating the Cell Scaffold, and FIG. 31 demonstrates the assembled Cell Scaffold: Cell Scaffold's acrylic sheet containing islets (white spheres), agarose, and cylindrical ultrafiltrate channels (solid red circles). The hexagonal arrangement of cylindrical channels creates eight 800-μm cylindrical cell agarose tissue regions (dotted red circle) with a central 100 μm cylindrical channel. This configuration creates a diffusion distance ≤400 μm between the cells and ultrafiltrate.

A small-scale iBAP prototype has been developed for vitro and in vivo Cell Scaffold testing and in vivo hemocompatibility testing. FIGS. 21 and 22A describe the small-scale iBAP, which possesses up to 2 $cm^2$ of SNM area. FIG. 21 is an exploded view of the iBAP components: the polycarbonate Flow Path component containing the blood flow path, two SNM, the Cell Scaffold containing the agarose seeded cells, the Polycarbonate Backside (PC Backside), and the Ultrafiltrate Outlet, Cell culture medium or blood flows through the Flow Path component at ~80 mmHg generating a TMP pressure between blood or cell culture medium and the Ultrafiltrate Outlet resulting in ultrafiltrate flow through the SNM, Cell Scaffold, PC Backside, and Ultrafiltrate Outlet, which is collected in a vein in the clinical setting or a collection tube in vitro. FIG. 22A is a picture of the assembled small-scale iBAP used for in vitro and in vivo testing.

Figure 42:
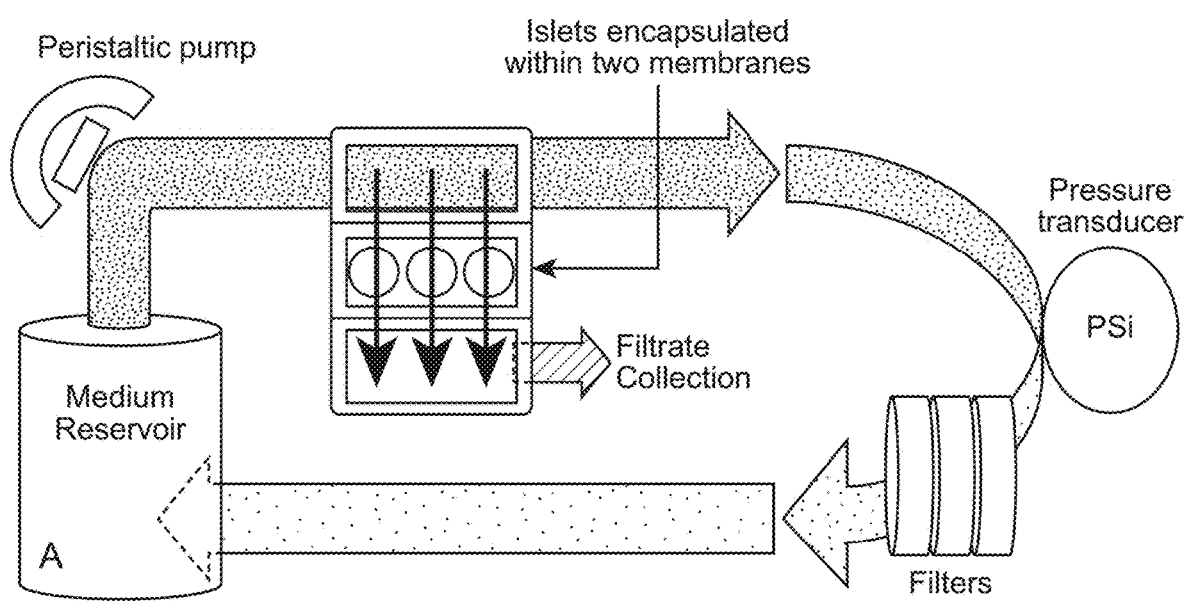
FIG. 42 shows a schematic of the mock circuit loop for in vitro assessment of SNM encapsulated islets under convection.
Figure 48:
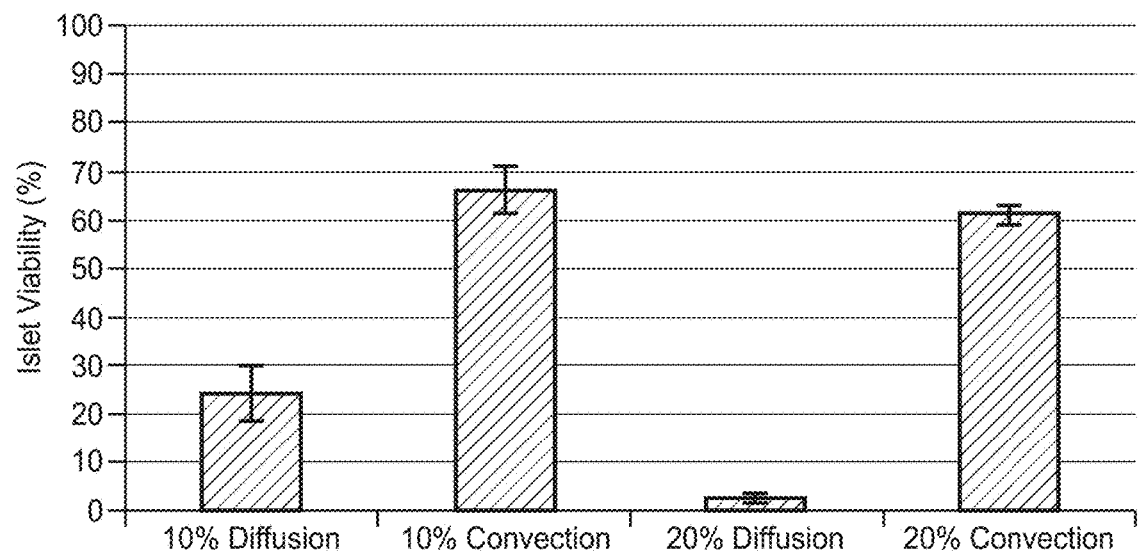
FIG. 48 shows Islet viability data from the in vitro experiments.
Figure 49:
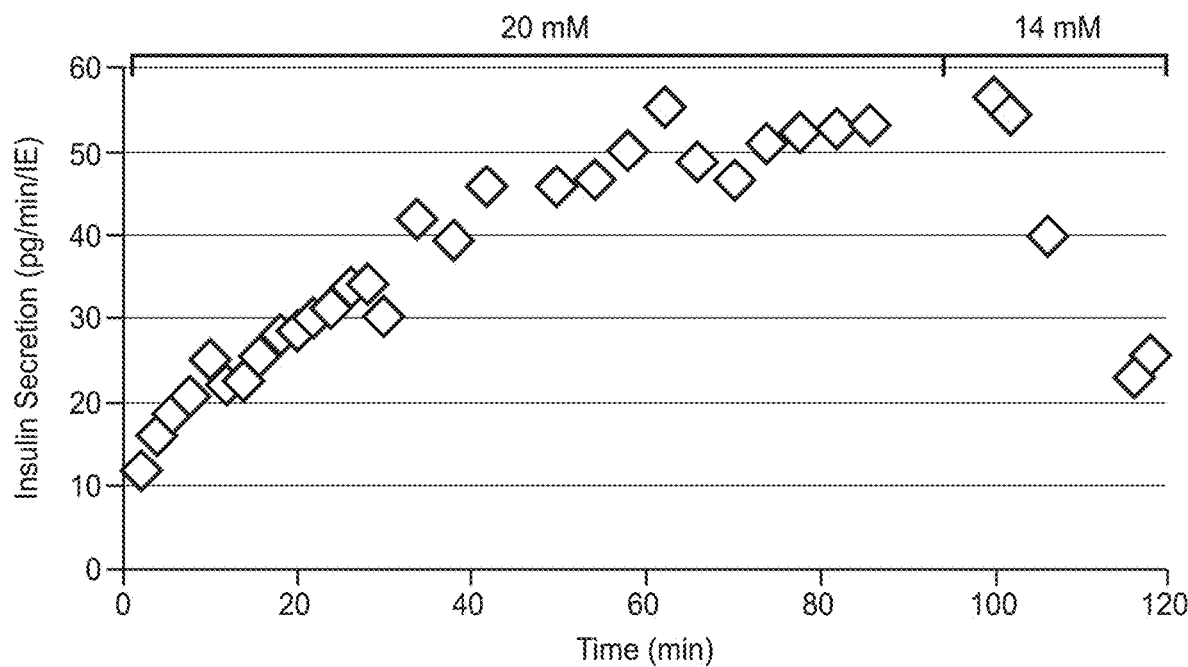
FIG. 49 shows Islet in vitro glucose-insulin kinetics data.
Figure 52:
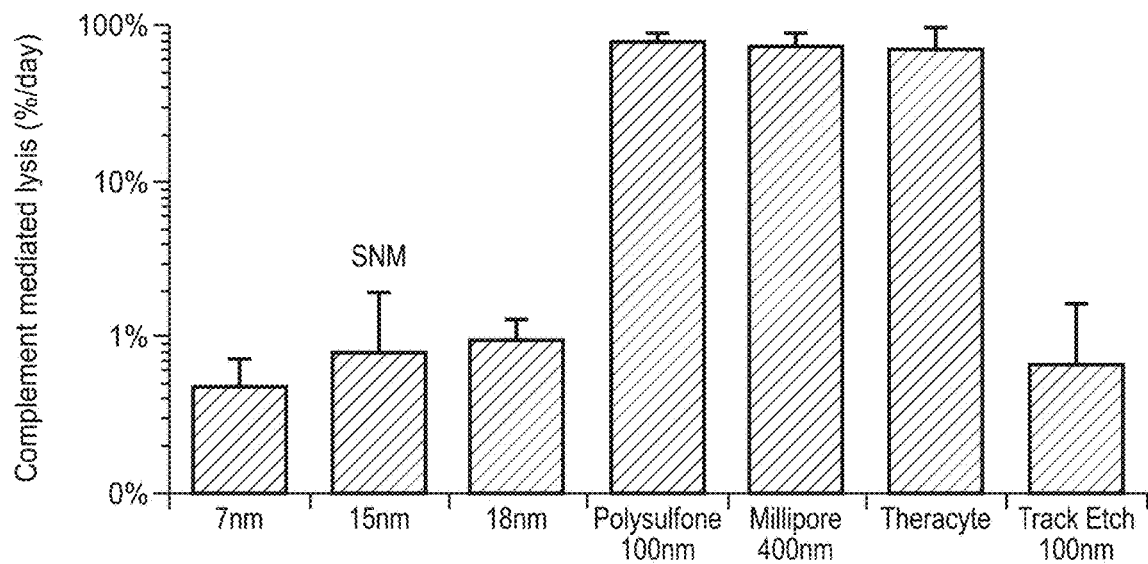
FIG. 52 shows complement mediated lysis of ovine erythrocytes for various membranes. SNM clearly outperform conventional polymer membranes.
Figure 53:
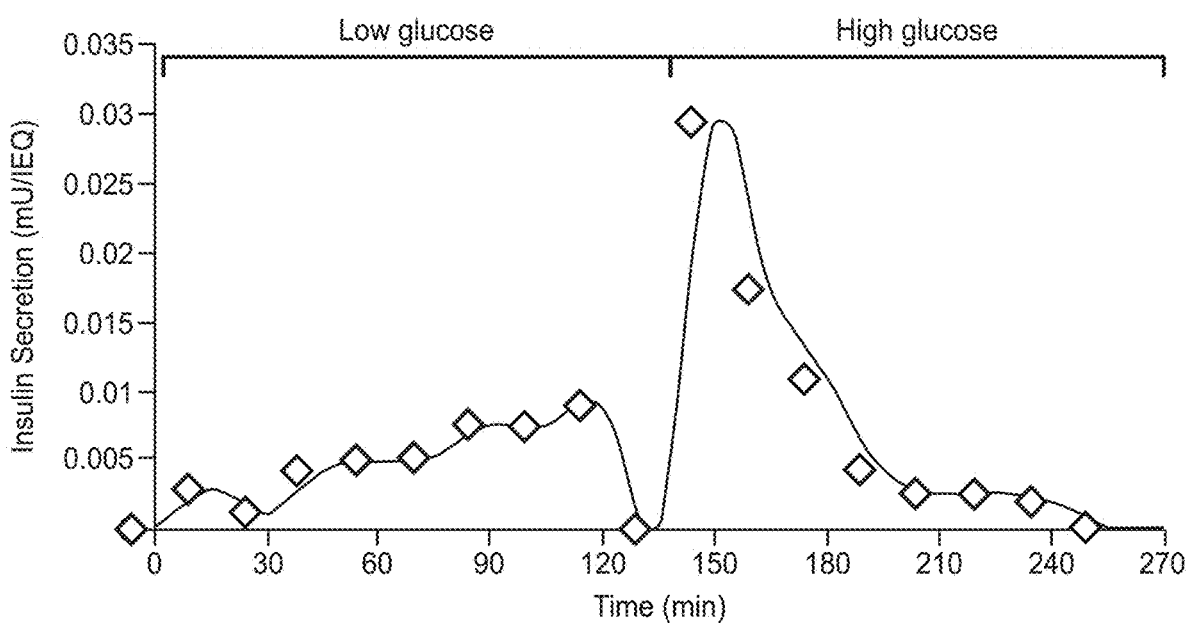
FIG. 53 shows rapid glucose-stimulated insulin response of SNM encapsulated islets.
Figure 54:
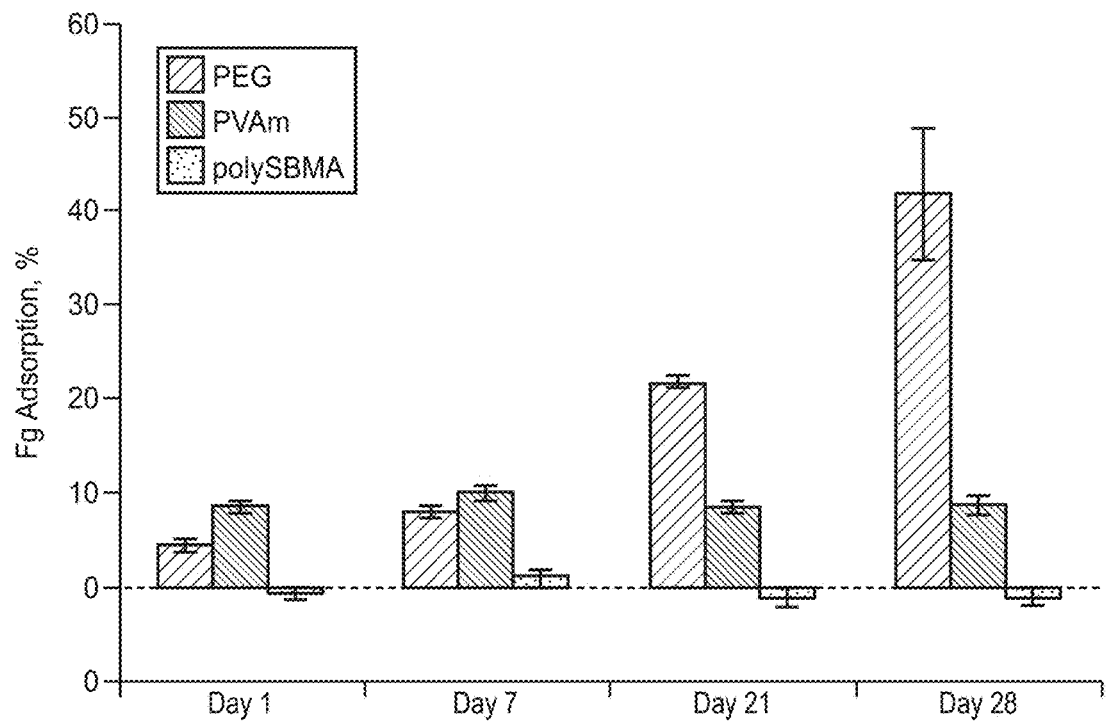
FIG. 54 shows fibrinogen deposition over a 1-month period on silicon coated substrates with various molecular coatings. PVAm and polySBMA appear suitable for long-term implantation.

In vitro small-scale Cell Scaffold testing demonstrated increased islet viability with convection versus diffusion and promising glucose-insulin kinetics. Freshly isolated mouse islets at either 10% or 20% islet density by volume (or 5,700 $IEQ/cm^2$ or 11,400 $IEQ/cm^2$ respectively) within the small-scale Cell Scaffold were loaded into an iBAP containing 40 nm SNM. The iBAP devices were connected to a mock circuit loop (FIG. 42) in an incubator. For each islet density, three Cell Scaffolds were tested in diffusion or convection. After 3 days, the islets were stained by FDA+PI to determine cell viability, FIG. 33C (iv and v) is a representative image from the 20% islet density experiments. For both islet densities, Cell Scaffolds exposed to convection possessed greater islet viability than Cell Scaffolds exposed to diffusion (FIG. 48). The 40 nm SNM supported islet viability at clinically relevant islet densities.

Figure 43:
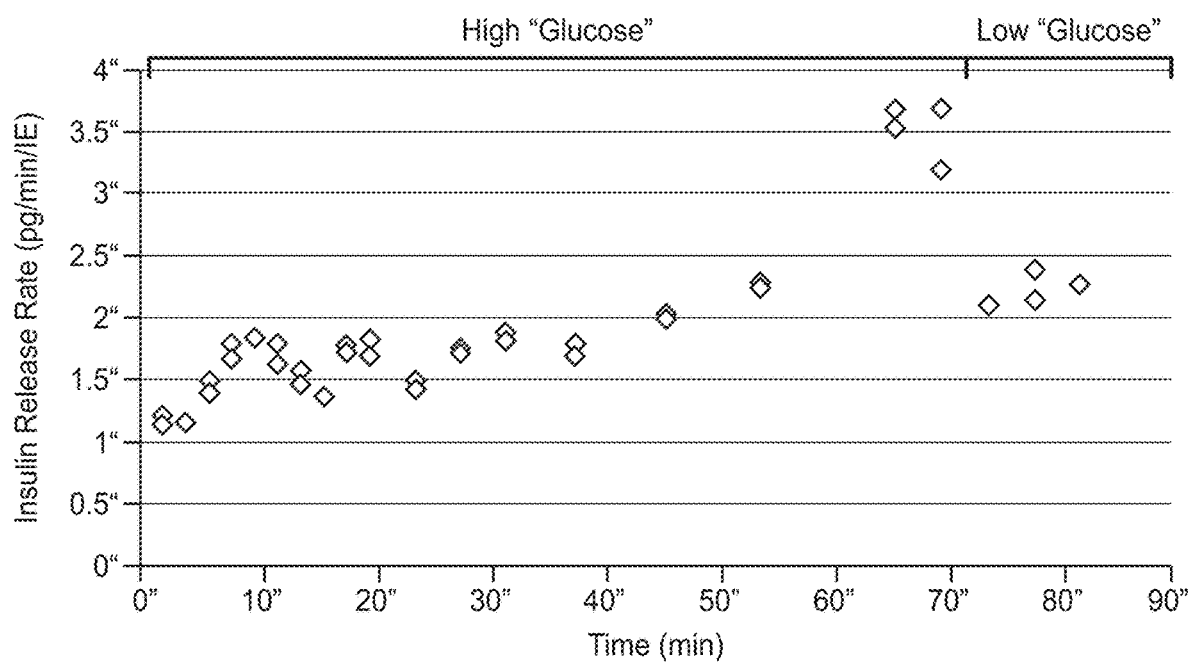
FIG. 43 shows islet in vitro glucose-insulin kinetics data.

Human islet function was assessed in a 90-minute glucose-insulin kinetics study. Freshly isolated human islets at 10% islet density in the small-scale Cell Scaffold were loaded into an iBAP with a 40 nm SNM and then stabilized in low glucose cell culture medium for 1 hour in the mock circuit loop. At time zero, the glucose concentration was increased for 70 minutes and ultrafiltrate samples were collected from the Ultrafiltrate Outlet. FIG. 43 demonstrates the first insulin peak at ~8 minutes followed by sustained and heightened insulin secretion until the glucose concentration was reduced at 70 minutes, where a decrease in insulin production was then observed. A clinically functioning iBAP must possess an insulin response in <15 minutes to achieve effective glycemic control.

Figure 44:
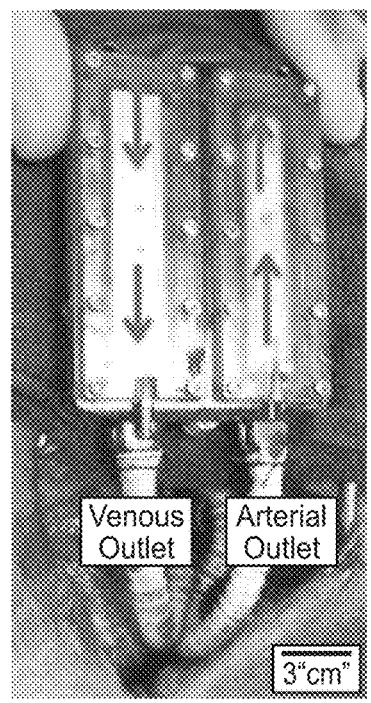
FIG. 44 shows an image of the prototype full-scale iBAP connected to the porcine vasculature on the day of implant.

A prototype full-scale iBAP was designed, CFD modeled, and demonstrated blood flow path patency in an in vivo 7-day hemocompatibility study. Full-scale iBAP blood flow path designs were generated in SolidWorks and analyzed in ANSYS Fluent to determine the feasibility of extending the blood flow path from the small-scale iBAP prototype. This first generation full-scale iBAP was manufactured from medical grade polycarbonate and loaded with SNM. The full-scale iBAP was intravascularly implanted into a healthy pig (FIG. 44) and heparin was administered at 100 units/kg perioperatively and then a twice-daily regime of 1.5 mg/kg of acetylsalicylic acid (aspirin). The device was explanted at 7 days and was patent throughout the experiment.

Example 5

Figure 36A:
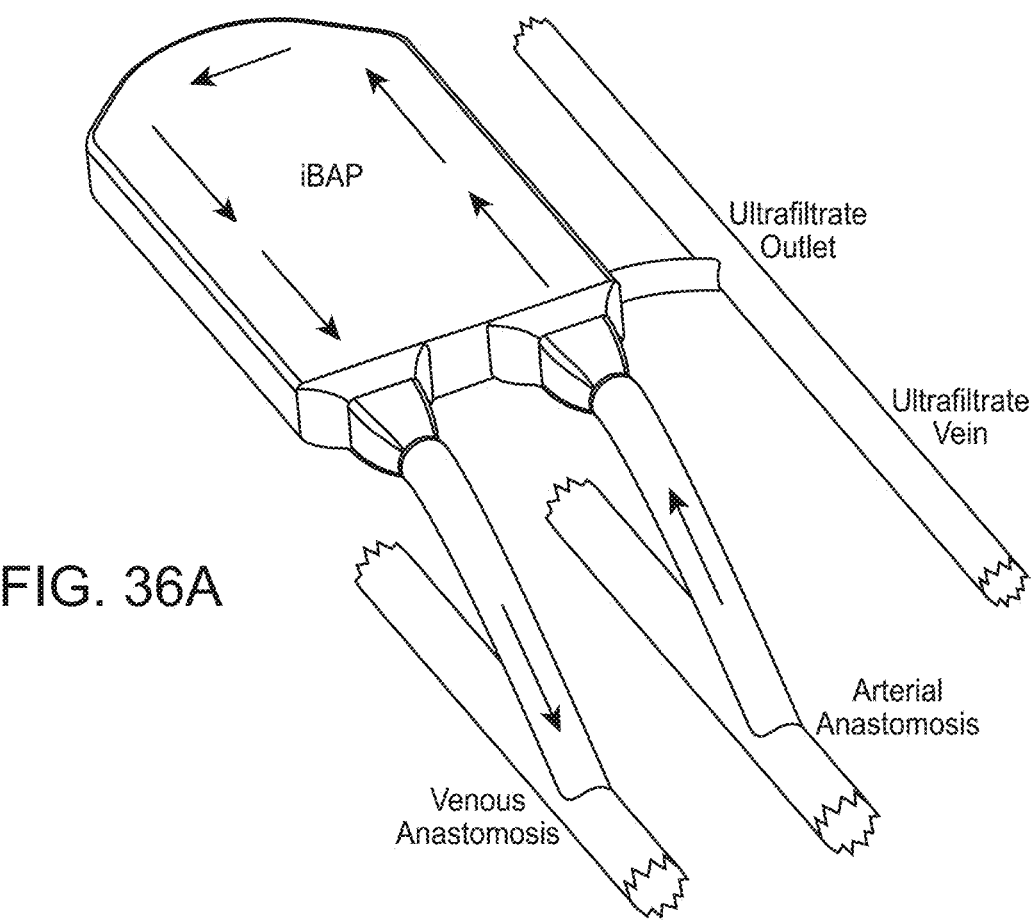
FIGS. 36A-36B shows blood flow in the iBAP.
Figure 36B:
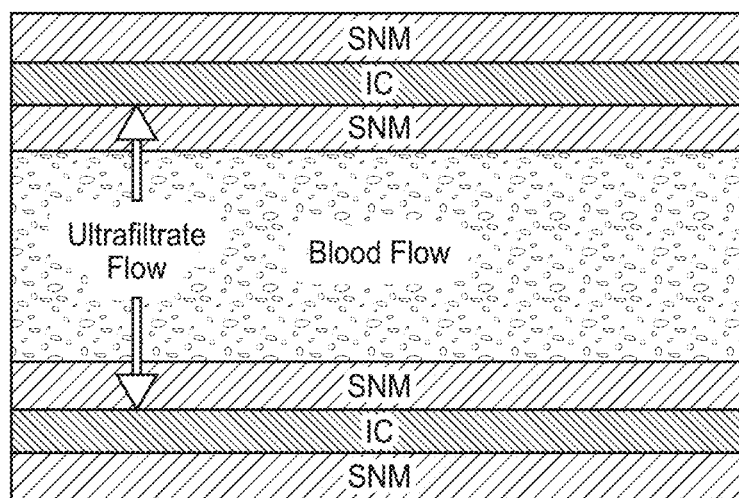

The iBAP will be connected to arterio-venous grafts and a pressure drop between the artery and vein will produce ultrafiltrate flow through the SNM encapsulated Cell Scaffold seeded with insulin producing cells, carrying nutrients to the cells and insulin to the ultrafiltrate vein (FIG. 36A-B). The SNM is a biocompatible and high hydraulic permeability membrane that produces high levels of ultrafiltrate enabling physiologic nutrient delivery to, and insulin secretion from, the Cell Scaffold, while the cells are human embryonic stem cell (hESC) derived mature beta cells arranged in ~100 μm diameter spheres possessing glucose stimulated insulin secretion both in vitro and in vivo.

FIG. 31 shows a gross image of islets and agarose mixture inside the IC in which the maximum diameter surrounding each ultrafiltrate channel is 800 μm. The figure shows a microscopic image of the Cell Scaffold containing agarose gel, islets, and cylindrical ultrafiltrate channels.

FIG. 32A-C shows in vitro testing of the intravascular bioartificial pancreas device (iBAP) with 10% or 20% islet density encapsulated with 10 nm-pore size SNM. FIG. 32A shows glucose-insulin kinetics of the SNM-encapsulated iBAP with 10% (i) or 20% (ii) islet densities under convection was measured from exposing them to a series of low, high, and low glucose conditions. FIG. 32B shows the SNM-encapsulated iBAP with 10% islet density under convection (10% convection) showed significantly higher viability compared to that of 10% islet density under diffusion (10% diffusion), and 20% islet density under both diffusion (20% diffusion) and convection (20% convection) after 3 days. (n>3, *p<0.05). Viabilities of islets that were immediately encapsulated in agarose and dispensed into the islet chamber (IC) without further testing were evaluated as the in vitro positive control. FIG. 32C shows viable (green) and dead (red) cells were stained for in vitro positive control (i), 10% islet density under diffusion (ii), 10% islet density under convection (iii), 20% islet density under diffusion (iv), and 20% islet density under convection (v) (scale bar=50 μm). The SNM-encapsulated iBAP with 10% islet density under convection (iii) showed higher viability than that of 10% islet density under diffusion (ii), and 20% islet density under both diffusion (iv) and convection (v). The 10% islet density under diffusion (ii), and 20% islet density under both diffusion (iv) and convection (v) showed similar viability with significant amount of cell death.

FIG. 33A-C shows in vitro testing of the intravascular bioartificial pancreas device (iBAP) with 10% or 20% islet density encapsulated with 40 nm-pore size SNM. FIG. 33A shows glucose-insulin kinetics of the SNM-encapsulated iBAP with 10% (i) or 20% (ii) islet densities under convection was measured from exposing them to a series of low, high, and low glucose conditions. FIG. 33B shows the SNM-encapsulated iBAP with 10% and 20% islet density under convection (10% & 20% convection) showed significantly higher viability compared to that of 10% and 20% islet density under diffusion (10% & 20% diffusion) after 3 days (n>3, *p<0.05). Viabilities of islets that were immediately encapsulated in agarose and dispensed into the islet chamber (IC) without further testing were evaluated as the in vitro positive control. FIG. 33C shows viable (green) and dead (red) cells were stained for in vitro positive control (i), 10% islet density under diffusion (ii), 10% islet density under convection (iii), 20% islet density under diffusion (iv), and 20% islet density under convection (v) (scale bar=50 μm). The SNM-encapsulated iBAP with 10% and 20% islet density under convection (iii & v) showed higher viability than those under diffusion (ii & iv). In particular, the 20% islet density under diffusion (iv) showed significant amount of cell death.

FIG. 34A-D shows in vivo testing of the intravascular bioartificial pancreas device (iBAP) with 5% islet density encapsulated with 10 nm-pore size SNM for 3 days. FIG. 34A shows an image of the explanted diffusion-based iBAP (i). An SEM image of the implanted membrane showing attachment of red blood cells and platelets (ii) (scale bar=10 μm). FIG. 34B shows immunofluorescence staining of platelet adhesion CD41 marker (green) and platelet activation CD62p marker (red). The rectangular pore-containing regions surrounded by solid silicon regions were shown in the bright field image (i). The platelet adhesion (green) mostly occurred in the window regions where pores reside, whereas minimal platelet activation (red) was detected (ii) (scale bar=20 μm). FIG. 34C shows the SNM-encapsulated iBAP with 5% islet density under diffusion both in vitro (in vitro 5% diffusion) and in vivo (in vivo 5% diffusion) showed significantly higher viability compared to the in vitro negative control (n>3, *p<0.05). The in vitro negative control was those islets that were assembled in the iBAP with no medium circulation for 3 days. Viabilities of islets that were immediately encapsulated in agarose and dispensed into the islet chamber (IC) without further testing were evaluated as the in vitro positive control. FIG. 34D shows viable (green) and dead (red) cells were stained for in vitro positive control (i), in vitro negative control (ii), in vitro 5% diffusion (iii), in vivo 5% islet density under diffusion (iv) (scale bar=50 μm). The SNM-encapsulated iBAP with 5% islet density under convection (iii & v) showed similar viability to the in vitro positive control.

FIG. 35 A-D shows in vivo testing of the intravascular bioartificial pancreas device (iBAP) with 10% islet density encapsulated with 10 nm-pore size SNM under either diffusion or convection for 3 days. FIG. 35A shows an image of the explanted iBAP with diffusion (back) and convection (front) of the device (i). An SEM image of the diffusion-side implanted membrane showed a patent surface (ii, top) (scale bar=100 μm) and an SEM image of the convection-side membrane presented coverage of proteins and cells on the surface (ii) (scale bar=10 μm). FIG. 35B shows immunofluorescence staining of platelet adhesion CD41 marker (green) and platelet activation CD62p marker (red). The rectangular pore-containing regions surrounded by solid silicon regions were shown in the bright field image for diffusion-side membrane (i) and convection-side membrane (iii). The platelet adhesion (green) was minimal on the diffusion-side membrane (ii), whereas more platelet adhesion (green) and activation (red) was detected on the convection-side membrane (iv) (scale bar=20 μm). FIG. 35C shows the SNM-encapsulated iBAP with 10% islet density under convection both in vitro (in vitro 10% convection) and in vivo (in vivo 10% convection) showed higher cell viability compared to that under diffusion in vitro (in vitro 10% diffusion) and in vivo (in vivo 10% diffusion). (n>3, *p<0.05). The in vitro negative control was those islets that were assembled in the iBAP with no medium circulation for 3 days. Viabilities of islets that were immediately encapsulated in agarose and dispensed into the islet chamber (IC) without further testing were evaluated as the in vitro positive control. FIG. 35D shows viable (green) and dead (red) cells were stained for in vitro positive control (i), in vitro negative control (ii), in vitro 10% islet density under diffusion (iii), in vitro 10% islet density under convection (iv), in vivo 10% islet density under diffusion (v), in vivo 10% islet density under convection (vi) (scale bar=50 μm). The SNM-encapsulated iBAP with 10% islet density under convection in vivo (vi) showed similar viability to the in vitro positive control.

FIG. 36A-B shows blood flow in the iBAP. FIG. 36A shows an illustration of the full-scale iBAP connected to arterial-venous grafts and an Ultrafiltrate Outlet catheter delivering insulin rich ultrafiltrate to the ultrafiltrate vein. Blood flows into the iBAP and a looped blood channel transports blood to a vein. The SNM encapsulated IC is placed directly above and below the blood channel. FIG. 36B shows a cross-sectional view perpendicular to blood flow illustrating the blood channel surrounded by the SNM (green) encapsulated IC (blue). Ultrafiltrate (black arrows) crosses the SNM encapsulated IC into ultrafiltrate channels (side) and exits the Ultrafiltrate Outlet catheter into the ultrafiltrate vein.

FIG. 37 shows daily measurement of the systematic cytokine concentration in the pig. The intravascular bioartificial pancreas (iBAP) with 5% islet density encapsulated with 10 nm-pore size SNM. Cytokines namely granulocyte-macrophage colony-stimulating factor (GM-CSF), tumor necrosis factor-alpha (TNF-α), interleukin 1-alpha (IL-1α), interleukin 1-beta (IL-1β), interleukin 8 (IL-8), interleukin 12 (IL-12), interleukin 18 (IL-18), interleukin-1 receptor antagonist (IL-1Ra), interleukin 4 (IL-4), and interleukin 10 (IL-10) were analyzed. Interferon gamma (IFN-ϒ) was not detected. About 35.89 pg/ml of interleukin 2 (IL-2) was detected post-implantation on Day 0 only.

FIG. 38 shows daily measurement of the systematic cytokine concentration in the pig. The intravascular bioartificial pancreas (iBAP) with 10% islet density encapsulated with 10 nm-pore size SNM. Cytokines namely Interferon gamma (IFN-ϒ), tumor necrosis factor-alpha (TNF-α), interleukin 1-alpha (IL-1α), interleukin 1-beta (IL-1β), interleukin 2 (IL-2), interleukin 6 (IL-6), interleukin 12 (IL-12), interleukin 18 (IL-18), interleukin-1 receptor antagonist (IL-1Ra), interleukin 4 (IL-4), and interleukin 10 (IL-10) were analyzed. Granulocyte-macrophage colony-stimulating factor (GM-CSF) was not detected. About 25.44 pg/ml of interleukin 8 (IL-8) was detected on Day 2 only.

FIG. 39 shows silicon nanopore membrane (SNM) hydraulic permeability as a function of pore size.

FIG. 40 shows SEM images of uncoated (left) and PEG-coated (right) silicon surfaces at low (top) and high (bottom) magnification after 30 days of blood exposure in vivo in femoral vessels of anticoagulant free rodents. The uncoated samples displayed adherent platelet-fibrin clots, while the coated surfaces were generally free of thrombus.

The invention claimed is:
1. A bioartificial ultrafiltration device comprising:
a first planar scaffold and a second planar scaffold each comprising a matrix comprising a population of cells and a plurality of channels adjacent the population of cells, wherein the channels extend from a first surface to a second surface of each of the planar scaffolds;
a first semipermeable ultrafiltration membrane disposed on the first surface of the first and second planar scaffolds;
a first compartment adjacent to and sandwiched between the first surface of the first and second planar scaffolds and comprising an inlet and an outlet, wherein the first semipermeable ultrafiltration membrane allows transport of ultrafiltrate from the first compartment to the scaffolds;
a second compartment adjacent to the second surface of the first planar scaffold and comprising an outlet;
a third compartment adjacent to the second surface of the second planar scaffold and comprising an outlet,
wherein the first semipermeable ultrafiltration membrane comprises a plurality of pores having a width in the range of 5 nm-5 micron, and
wherein the ultrafiltrate traverses from the plurality of channels in the scaffolds into the second compartment and the third compartment.

2. The device of claim 1, further comprising a second semipermeable ultrafiltration membrane comprising a plurality of pores having a width in the range of 5 nm-5 micron and wherein the second semipermeable ultrafiltration membrane is disposed on the second surface of the first and second planar scaffolds and wherein the ultrafiltrate traverses from the plurality of channels in the scaffolds into the second compartment and the third compartment via the second semipermeable ultrafiltration membrane.

3. The device of claim 2, wherein the second semipermeable ultrafiltration membrane comprises a plurality of pores having a width larger than the width of the plurality of pores in the first semipermeable ultrafiltration membrane.

4. The device of claim 1, wherein the inlet of the first compartment is connectable to a tubing for connection to an artery of a subject.

5. The device of claim 1, wherein the outlet of the first compartment is connectable to a tubing for connection to an artery or a vein of a subject.

6. The device of claim 1, wherein the outlet of the second compartment is connectable to a tubing for connection to at least one blood vessel of a subject and/or to an analyte analysis device.

7. The device of claim 1, wherein the outlet of the third compartment is connectable to a tubing for connection to at least a blood vessel of a subject and/or to an analyte analysis device.

8. The device of claim 1, wherein the outlet of the second compartment and the outlet of the third compartment are connected to a single tubing for connection to at least a blood vessel of a subject and/or to an analyte analysis device.

9. The device of claim 1, wherein the surface area of the first semipermeable ultrafiltration membrane is in the range of 1 $cm^2$-100 $cm^2$.

10. The device of claim 1, wherein the surface area of the first semipermeable ultrafiltration membrane is in the range of 15 $cm^2$-30 $cm^2$.

11. The device of claim 2, wherein the surface area of the second semipermeable ultrafiltration membrane is in the range of 1 cm$^2$-100 cm$^2$.

12. The device of claim 2, wherein the surface area of the second semipermeable ultrafiltration membrane is in the range of 15 cm$^2$-30 cm$^2$.

13. The device of claim 1, wherein the cells are insulin producing cells.

14. The device of claim 13, wherein the insulin producing cells are derived from differentiation of stem cells.

15. The device of claim 13, wherein the insulin producing cells are pancreatic cells isolated from pancreatic islets.

16. The device of claim 1, wherein the cells are autologous to the subject comprising the device.

17. The device of claim 1, wherein the cells are xenogenic to a subject comprising the device.

18. The device of claim 1, wherein the cells are allogenic to a subject comprising the device.

19. The device of claim 1, wherein the pores of the first semipermeable ultrafiltration membrane are rectangular pores having a depth of 100-1000 nm, a width of 3 nm-50 nm and a length of 1 micron-5 micron.

20. The device of claim 2, wherein the pores of the second semipermeable ultrafiltration membrane are rectangular pores having a depth of 100-1000 nm, a width of 3 nm-50 nm and a length of 1 micron-5 micron.

* * * * *

UNITED STATES PATENT AND TRADEMARK OFFICE
CERTIFICATE OF CORRECTION

PATENT NO. : 11,666,691 B2
APPLICATION NO. : 17/343361
DATED : June 6, 2023
INVENTOR(S) : Shuvo Roy et al.

Page 1 of 1

It is certified that error appears in the above-identified patent and that said Letters Patent is hereby corrected as shown below:

In the Specification

In Column 7, Line 41, delete "a." and insert -- a --.
In Column 12, Line 18, delete "polyoxamers," and insert -- poloxamers, --.
In Column 12, Line 65, delete "polytetrafluorethylene" and insert -- polytetrafluoroethylene --.
In Column 13, Line 11, delete "polylactic-co-glycolic" and insert -- poly(lactic-co-glycolic --.
In Column 13, Line 17, delete "polyoxamer," and insert -- poloxamer, --.
In Column 18, Line 28, delete "carbond" and insert -- carbon --.
In Column 18, Line 31-32, delete "polytetrafluorethylene," and insert -- polytetrafluoroethylene, --.
In Column 24, Line 53, after "mmHg" insert -- . --.
In Column 32, Line 62, delete "1" and insert -- l --.
In Column 35, Line 46, delete "that that" and insert -- that --.
In Column 37, Line 29, delete "secretion3l" and insert -- secretion31 --.
In Column 43, Line 1, delete "a." and insert -- a --.

Signed and Sealed this
Twenty-second Day of July, 2025

Coke Morgan Stewart
*Acting Director of the United States Patent and Trademark Office*